US012653714B1

(12) United States Patent
Reynard

(10) Patent No.: US 12,653,714 B1
(45) Date of Patent: Jun. 16, 2026

(54) SYSTEMS AND METHODS FOR ENDOTHELIAL REGENERATION OF SCHLEMM'S CANAL

(71) Applicant: Michael Reynard, Santa Monica, CA (US)

(72) Inventor: Michael Reynard, Santa Monica, CA (US)

( * ) Notice: Subject to any disclaimer, the term of this patent is extended or adjusted under 35 U.S.C. 154(b) by 0 days.

(21) Appl. No.: 19/533,080

(22) Filed: Feb. 6, 2026

Related U.S. Application Data

(62) Division of application No. 19/348,908, filed on Oct. 3, 2025, now Pat. No. 12,569,367.

(51) Int. Cl.
*A61F 9/00* (2006.01)
*A61F 9/007* (2006.01)
*A61M 25/00* (2006.01)

(52) U.S. Cl.
CPC ............ *A61F 9/0017* (2013.01); *A61F 9/007* (2013.01); *A61M 25/0045* (2013.01);
(Continued)

(58) Field of Classification Search
CPC ... A61F 9/0017; A61F 9/007; A61M 25/0045; A61M 2025/0057; A61M 2202/0007;
(Continued)

(56) References Cited

U.S. PATENT DOCUMENTS

| | | |
|---|---|---|
| 4,655,771 A | 4/1987 | Wallsten |
| 5,478,338 A | 12/1995 | Reynard |

(Continued)

FOREIGN PATENT DOCUMENTS

| | | | | |
|---|---|---|---|---|
| CN | 102971030 | * | 3/2013 | .............. A61P 27/06 |
| WO | WO-9211896 A1 | * | 7/1992 | .............. A61K 38/49 |

(Continued)

OTHER PUBLICATIONS

Charters, L. (Jun. 1, 2023). A closer look at how cell therapy for corneal endothelial disease is gaining traction | ophthalmology times europe. Ophthalmology Times Europe. (Year: 2023).*

(Continued)

*Primary Examiner* — Ariana Zimbouski
*Assistant Examiner* — Matthew Wrubleski
(74) *Attorney, Agent, or Firm* — Richard A Baker, Jr.

(57) ABSTRACT

The present disclosure provides systems, methods, and compositions for delivering endothelial cells into Schlemm's canal to restore physiological outflow in glaucoma and other ocular disorders. The document encompasses diverse devices and hydrogel carriers suitable for delivering endothelial cells, including conduits, microcatheters, scaffolds, stents, support devices, Schlemm's canal expanders, viscodilation balloons, tensioning sutures, hydrogel sleeves, and injectable formulations. The endothelial cells may be combined with extracellular matrix components, drugs, or growth factors, and may be delivered using controlled-release hydrogels to ensure uniform circumferential seeding. The system enables removal of dysfunctional Schlemm's canal endothelial cells, OCT/OCTA-guided functional analysis, and re-endothelialization via bioengineered scaffolds. Embodiments further integrate artificial intelligence for intraoperative guidance, predictive analytics, and postoperative monitoring of endothelial integration. Safe dosing strategies are disclosed to avoid canal obstruction, and commercial applications include combination biologic-device products and digital health solutions.

15 Claims, 8 Drawing Sheets

(52) U.S. Cl.
CPC .............. *A61M 2025/0057* (2013.01); *A61M 2202/0007* (2013.01); *A61M 2202/097* (2013.01); *A61M 2205/0238* (2013.01); *A61M 2205/3306* (2013.01); *A61M 2205/3327* (2013.01); *A61M 2210/0612* (2013.01)

(58) Field of Classification Search
CPC .... A61M 2202/097; A61M 2205/0238; A61M 2205/3306; A61M 2205/3327; A61M 2210/0612
See application file for complete search history.

(56) References Cited

U.S. PATENT DOCUMENTS

| | | | |
|---|---|---|---|
| 5,558,669 | A | 9/1996 | Reynard |
| 5,899,517 | A | 5/1999 | Murawa et al. |
| 6,140,127 | A | 10/2000 | Sprague |
| 6,428,501 | B1 | 8/2002 | Reynard |
| 8,439,972 | B2 | 5/2013 | Badawi et al. |
| 8,540,659 | B2 | 9/2013 | Berlin |
| 8,894,603 | B2 | 11/2014 | Badawi et al. |
| 9,510,973 | B2 | 12/2016 | Wardle |
| 9,642,746 | B2 | 5/2017 | Berlin |
| 10,154,924 | B2 | 12/2018 | Clauson et al. |
| 10,485,701 | B2 | 11/2019 | Haffner et al. |
| 10,517,769 | B2 | 12/2019 | Wood |
| 10,993,840 | B2 | 5/2021 | Berlin |
| 11,058,584 | B2 | 7/2021 | Berlin |
| 11,090,188 | B2 | 8/2021 | Badawi et al. |
| 11,116,660 | B2 | 9/2021 | Badawi et al. |
| 11,135,088 | B2 | 10/2021 | Wardle et al. |
| 11,259,961 | B2 | 3/2022 | Ianchulev |
| 11,344,477 | B2 | 5/2022 | Kahraman et al. |
| 11,389,327 | B2 | 7/2022 | Badawi et al. |
| 11,389,328 | B2 | 7/2022 | Badawi et al. |
| 11,419,762 | B2 | 8/2022 | Ianchulev |
| 11,504,270 | B1 | 11/2022 | Badawi et al. |
| 11,540,940 | B2 | 1/2023 | Noda et al. |
| 11,857,460 | B2 | 1/2024 | Badawi et al. |
| 11,872,158 | B2 | 1/2024 | Badawi et al. |
| 11,872,954 | B2 | 1/2024 | Neubauer |
| 11,938,058 | B2 | 3/2024 | Schieber et al. |
| 11,951,037 | B2 | 4/2024 | Badawi et al. |
| 12,016,796 | B2 | 6/2024 | Schieber et al. |
| 12,042,428 | B2 | 7/2024 | Badawi et al. |
| 12,213,914 | B2 | 2/2025 | Badawi et al. |
| 12,274,640 | B1 | 4/2025 | Reynard |
| 12,310,891 | B2 | 5/2025 | Badawi et al. |
| 12,310,892 | B2 | 5/2025 | Ianchulev et al. |
| 12,336,933 | B2 | 6/2025 | Noda et al. |
| 12,350,192 | B2 | 7/2025 | Badawi et al. |
| 2002/0013456 | A1 | 1/2002 | Sutcliffe et al. |
| 2002/0169130 | A1* | 11/2002 | Tu ............................. A61F 2/16 |
| | | | 514/249 |
| 2005/0220843 | A1* | 10/2005 | DeWitt ................... A61L 31/10 |
| | | | 424/487 |
| 2007/0191863 | A1* | 8/2007 | De Juan .............. A61F 9/00781 |
| | | | 606/108 |
| 2009/0138070 | A1* | 5/2009 | Holzer ...................... A61F 2/07 |
| | | | 623/1.42 |
| 2010/0185156 | A1* | 7/2010 | Kanner ............. A61M 25/0105 |
| | | | 604/190 |
| 2014/0296800 | A1* | 10/2014 | Erickson ........... A61M 39/0208 |
| | | | 604/288.02 |
| 2014/0323995 | A1* | 10/2014 | Clauson ............... A61F 9/0017 |
| | | | 604/290 |
| 2018/0036065 | A1 | 2/2018 | Yates et al. |
| 2019/0017017 | A1* | 1/2019 | Xie ........................ C12M 25/14 |
| 2019/0117459 | A1 | 4/2019 | Berlin |
| 2020/0188173 | A1 | 6/2020 | Berlin |
| 2020/0281766 | A1 | 9/2020 | Berlin |
| 2021/0386584 | A1 | 12/2021 | Badawi et al. |
| 2022/0104967 | A1 | 4/2022 | Badawi et al. |
| 2022/0104968 | A1 | 4/2022 | Badawi et al. |
| 2022/0280339 | A1 | 9/2022 | Badawi et al. |
| 2022/0280340 | A1 | 9/2022 | Badawi et al. |
| 2023/0080761 | A1* | 3/2023 | Taylor ................. A61K 9/0019 |
| | | | 424/488 |
| 2024/0366424 | A1 | 11/2024 | Badawi et al. |

FOREIGN PATENT DOCUMENTS

| | | |
|---|---|---|
| WO | 03045290 A1 | 6/2003 |
| WO | 2006066103 A2 | 6/2006 |
| WO | 2022062050 A1 | 3/2022 |

OTHER PUBLICATIONS

Blache U, Ehrbar M. Inspired by Nature: Hydrogels as Versatile Tools for Vascular Engineering. Adv Wound Care (New Rochelle). Jul. 1, 2018;7(7):232-246. doi: 10.1089/wound.2017.0760. PMID: 29984113; PMCID: PMC6032659 (Year: 2018).*

Carol W Chen,et al. Sustained release of endothelial progenitor cell-derived extracellular vesicles from shear-thinning hydrogels improves angiogenesis and promotes function after myocardial infarction, Cardiovascular Research, vol. 114, Issue 7, Jun. 1, 2018, pp. 1029-1040 (Year: 2018).*

* cited by examiner

Nanotopography
702

Nanopores
706

Hydrogel Sleeve
204

Nanoscale
Patterns
704

202

Bioactive
Sleeve
708

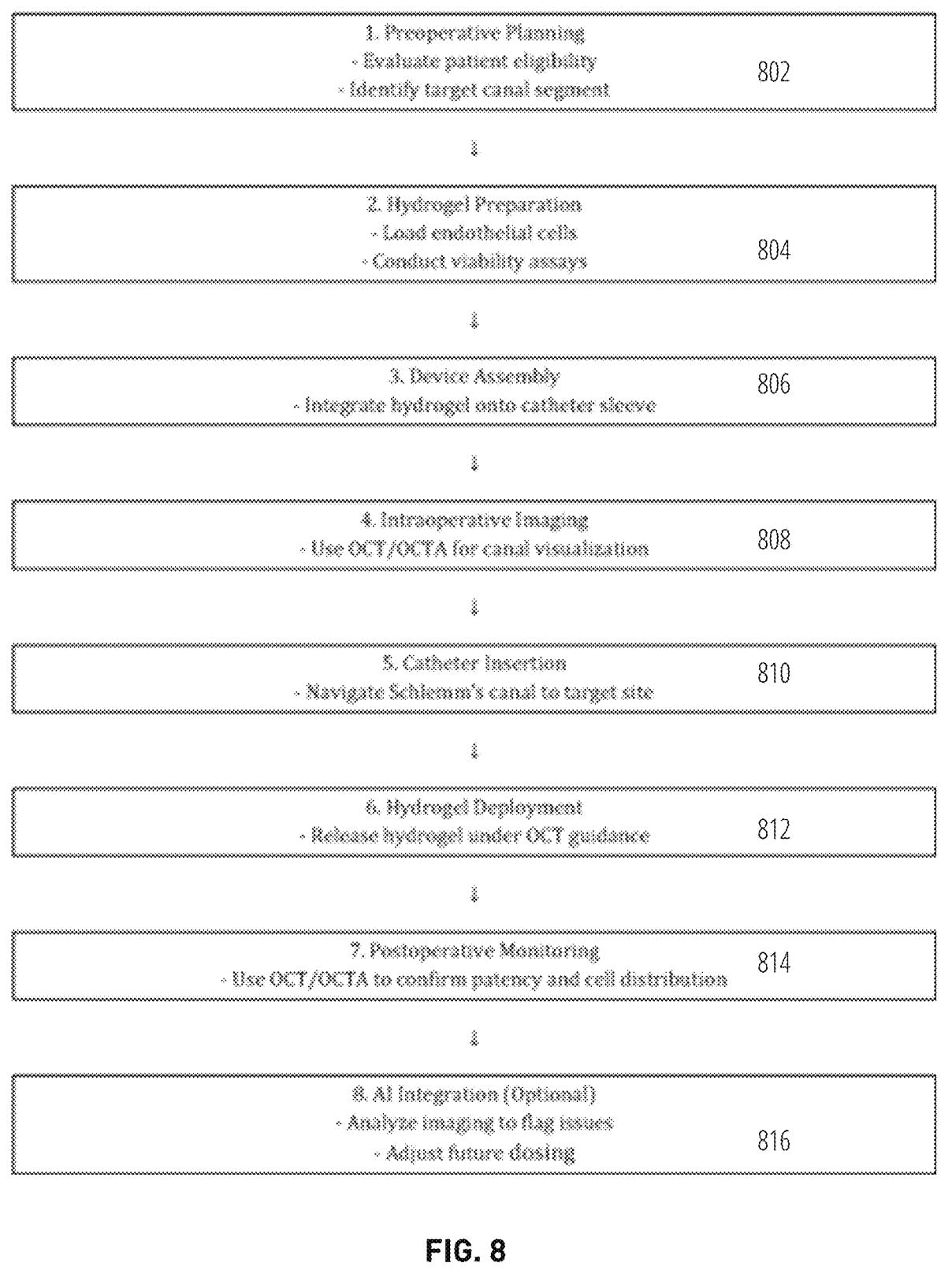

1. Preoperative Planning
- Evaluate patient eligibility
- Identify target canal segment                     802

↓

2. Hydrogel Preparation
- Load endothelial cells
- Conduct viability assays                          804

↓

3. Device Assembly
- Integrate hydrogel onto catheter sleeve           806

↓

4. Intraoperative Imaging
- Use OCT/OCTA for canal visualization              808

↓

5. Catheter Insertion
- Navigate Schlemm's canal to target site           810

↓

6. Hydrogel Deployment
- Release hydrogel under OCT guidance               812

↓

7. Postoperative Monitoring
- Use OCT/OCTA to confirm patency and cell distribution   814

↓

8. AI Integration (Optional)
- Analyze imaging to flag issues
- Adjust future dosing                              816

FIG. 8

SYSTEMS AND METHODS FOR ENDOTHELIAL REGENERATION OF SCHLEMM'S CANAL

CROSS-REFERENCE TO RELATED APPLICATIONS

This application is a Divisional of U.S. patent application Ser. No. 19/348,908, "Systems and Methods for Endothelial Regeneration of Schlemm's Canal", filed by inventor Michael Reynard on Oct. 3, 2025, said patent application incorporated herein in its entirety.

BACKGROUND

Field of the Inventions

The document relates generally to ophthalmic surgical and therapeutic techniques and more particularly to the delivery of endothelial cells into Schlemm's canal for the purpose of restoring physiological aqueous humor outflow and treating glaucoma and related conditions. The document also encompasses platform technologies for integrating endothelial cell therapy into various Schlemm's canal interventions, including but not limited to canaloplasty, viscodilation, microcatheter-based procedures, tension sutures, and future undisclosed devices.

Background of the Inventions

Glaucoma is a leading cause of irreversible blindness worldwide, affecting an estimated 80 million individuals. Elevated intraocular pressure (IOP) resulting from impaired aqueous humor outflow remains the primary modifiable risk factor. Minimally invasive glaucoma surgeries (MIGS) have emerged as effective alternatives to traditional trabeculectomy and tube shunt procedures, aiming to restore outflow through Schlemm's canal with reduced surgical trauma.

Despite advances in MIGS technology, long-term success rates remain limited by biological factors, including fibrosis, cellular damage, and loss of the canal's specialized inner wall endothelium. Schlemm's canal endothelium plays a critical role in aqueous humor transport through the formation of transcellular pores and vacuolar channels. Damage to or loss of this cell layer can compromise outflow even after successful mechanical interventions.

Currently available MIGS devices and procedures do not directly address the regenerative potential of replacing or repairing the endothelial lining of Schlemm's canal. A therapeutic gap exists for biologic or cell-based solutions capable of restoring normal canal function at the cellular level.

BRIEF SUMMARY

In one aspect, a device includes a catheter, configured for insertion into an incision providing access to Schlemm's canal of an eye, and a tubular hydrogel sleeve positioned around a distal shaft of the catheter, the tubular hydrogel sleeve includes endothelial cells.

The incision may be in the cornea. The tubular hydrogel sleeve may include polyethylene glycol (PEG). The tubular hydrogel sleeve may include collagen. The tubular hydrogel sleeve may include glucose. The tubular hydrogel sleeve may include nitinol. The tubular hydrogel sleeve may include nanopores. The device may also include a lumen configured to deliver a viscoelastic through the catheter.

In one aspect, a device includes a catheter, configured for insertion into an incision providing access to Schlemm's canal of an eye, and a hydrogel coating bonded to a surface of a distal shaft of the catheter, the hydrogel coating includes endothelial cells.

The incision may be in the sclera. The hydrogel coating may include hyaluronic acid. The hydrogel coating may include alginate. The device may also include a lumen configured to deliver a viscoelastic through the catheter.

In one aspect, a method includes creating an incision in an eye providing access to Schlemm's canal, inserting a catheter through the incision into the Schlemm's canal, the catheter includes hydrogel and endothelial cells, initiating degradation of the hydrogel to release the endothelial cells into the Schlemm's canal, and withdrawing the catheter.

The incision may be a corneal incision. The incision may be a scleral incision. The catheter may be inserted around one-quarter of the length of the Schlemm's canal. The method may also include monitoring coverage of the endothelial cells. The hydrogel may be a coating on the catheter. The hydrogel may be a tubular hydrogel sleeve positioned around a distal shaft of the catheter. The monitoring of the coverage of the endothelial cells may be performed with optical coherence tomography (OCT). The monitoring of the coverage of the endothelial cells may be performed with optical coherence tomography angiography (OCTA). Other technical features may be readily apparent to one skilled in the art from the following figures, descriptions, and claims.

BRIEF DESCRIPTION OF THE DRAWINGS

To easily identify the discussion of any particular element or act, the most significant digit or digits in a reference number refer to the figure number in which that element is first introduced.

FIG. 8 illustrates the regenerative hydrogel therapy workflow for Schlemm's canal.

DETAILED DESCRIPTION

This document provides a novel platform for regenerating the physiological outflow function of Schlemm's canal 104 through targeted endothelial cell delivery. Recognizing the limitations of mechanical glaucoma implants that bypass, rather than restore, the eye's native outflow resistance mechanisms, this document introduces a series of biologically-integrated and digitally enhanced delivery modalities that enable endothelial repopulation of Schlemm's canal 104.

At the core is the use of hydrogel-based systems, configured as sleeves, coatings, or injectable matrices, to deliver viable endothelial cells 208 to Schlemm's canal 104. These systems may be used independently or in conjunction with conventional interventional tools such as microcatheters, viscodilation balloons, and tensioning sutures. Hydrogel-coated conduits may slide circumferentially through the canal, releasing cells along their inner wall. Balloons used for viscodilation may simultaneously deliver cells embedded in degradable hydrogel layers, while tensioning sutures may act as bioactive scaffolds when impregnated with endothelial cell-laden coatings.

Additionally, this document includes injectable formulations that conform to Schlemm's canal 104 architecture, forming in-situ coatings that support cell adhesion and integration. The hydrogels may be engineered to degrade in a controlled manner, protecting cells during delivery and ensuring uniform distribution over time.

To enhance regenerative outcomes, the system optionally enables co-delivery of pharmaceutical agents, such as anti-inflammatory, anti-fibrotic, or angiogenic compounds. These agents support endothelial viability and mitigate the risk of fibrosis or canal obstruction.

Artificial intelligence further enhances the clinical utility of the techniques. Intraoperative AI may guide endothelial delivery in real time using OCT or OCTA. Postoperatively, AI-enabled imaging platforms may track cell integration and fluid flow dynamics, providing predictive insights and personalized care pathways for glaucoma management.

The system is designed to be biologically and digitally compatible with a wide range of existing surgical techniques. It avoids mechanical occlusion of the canal. The system may be integrated into combination biologic-device products, pre-packaged surgical kits, or digital platforms offering advanced analytics for treatment planning and follow-up.

By providing safe, scalable, and intelligent endothelial delivery methods, the system opens a new frontier in regenerative ophthalmology and physiologic intraocular pressure regulation.

Figure 1:
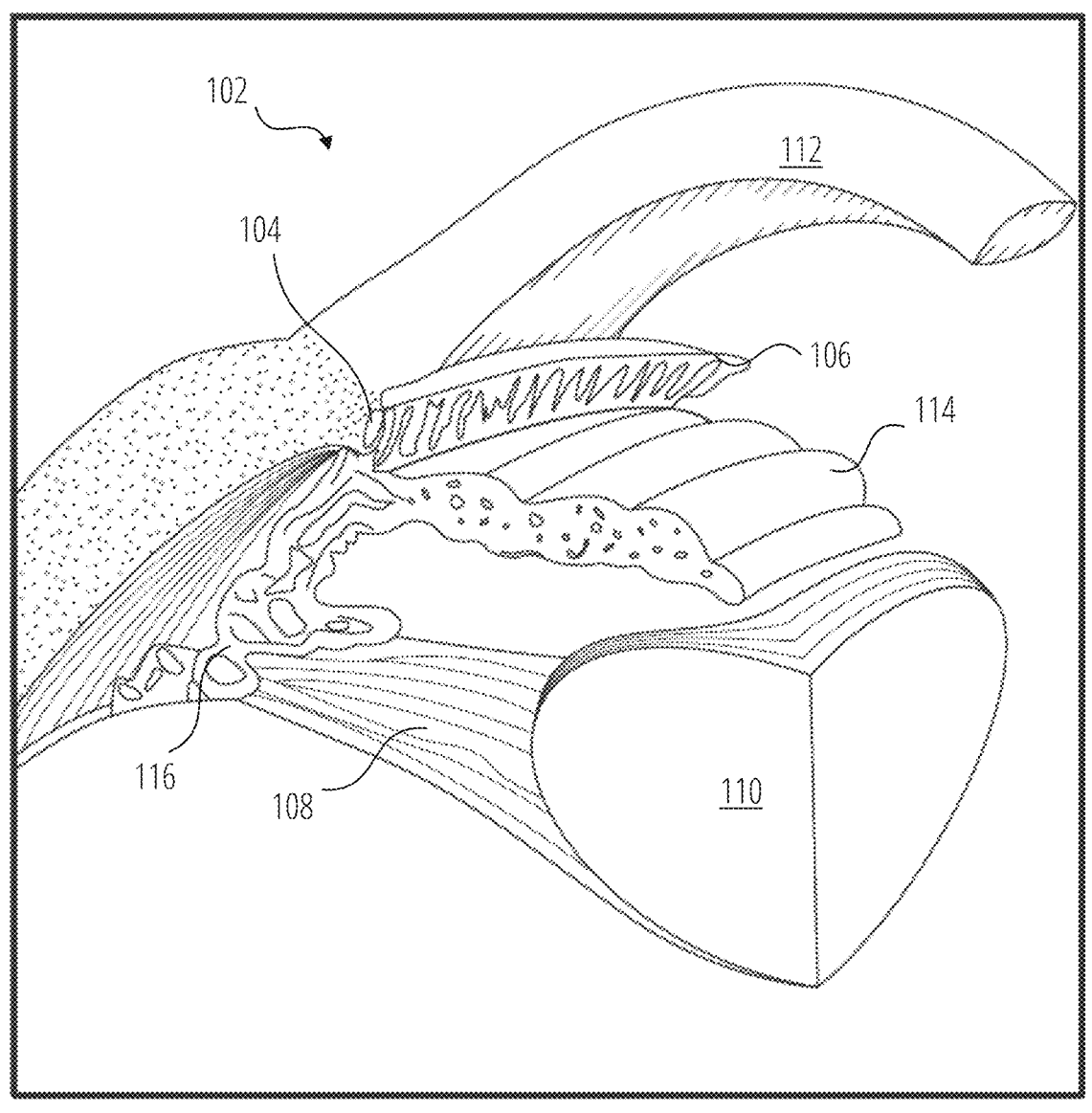
FIG. 1 illustrates the anatomy of Schlemm's Canal.

FIG. 1 shows the anatomy of Schlemm's canal 104 and the trabecular meshwork 106. Schlemm's canal 104 is represented by the white space that borders the posterior aspect of trabecular meshwork 106. The lens 110, the cornea 112, iris 114, ciliary body 116, and the Zonules 108 are also shown in FIG. 1.

Figure 2:
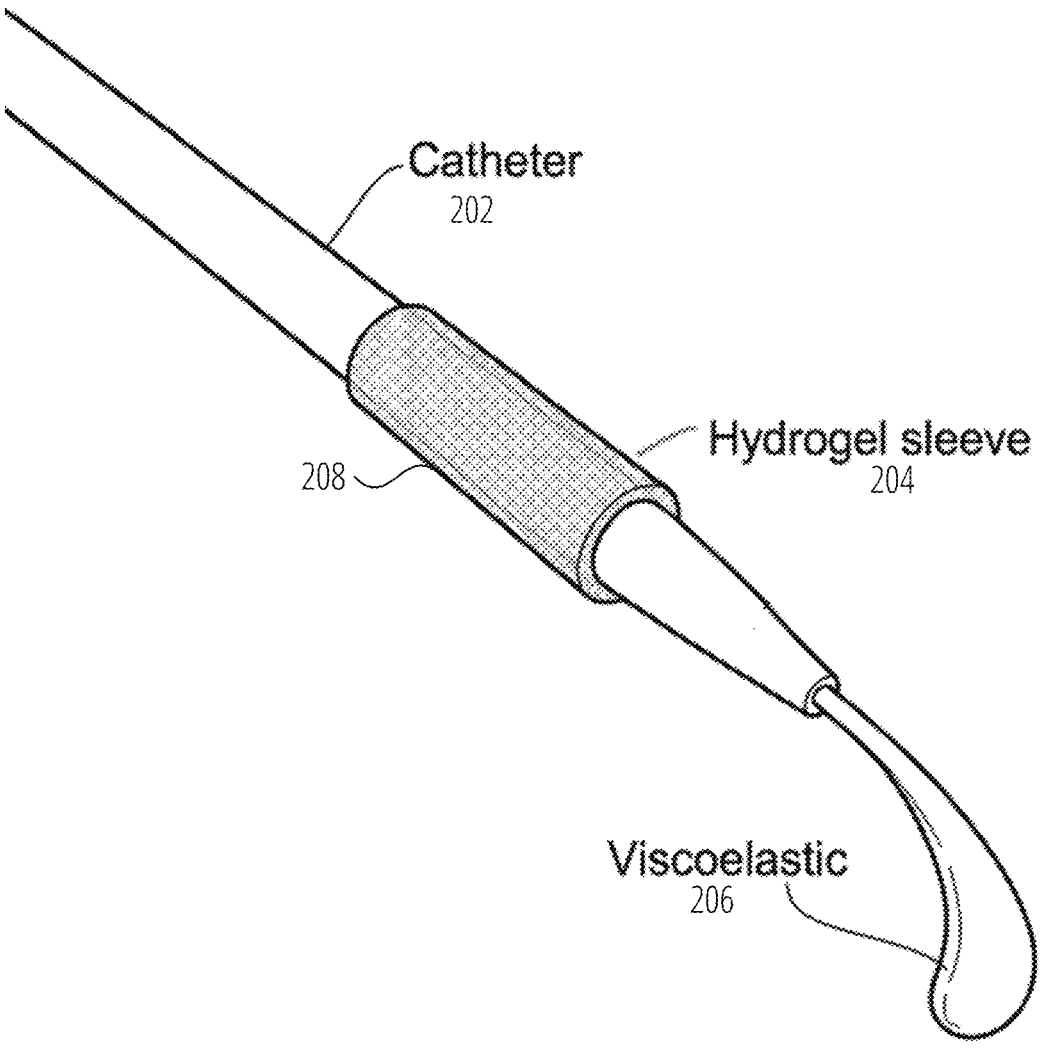
FIG. 2 shows a catheter with a hydrogel sleeve.

FIG. 2 shows a catheter 202 depicted with a hydrogel sleeve 204 encircling the external surface of the microcatheter. Viscoelastic 206 is being discharged from the catheter tip. The hydrogel sleeve 204 comprises a biocompatible matrix preloaded with endothelial cells 208 and configured to release said cells into Schlemm's canal 104 during circumferential catheter advancement directed circumferentially through the canal. The hydrogel sleeve 204 serves to reduce frictional resistance between the microcatheter and the canal wall, enhancing navigability and minimizing endothelial trauma.

Figure 3:
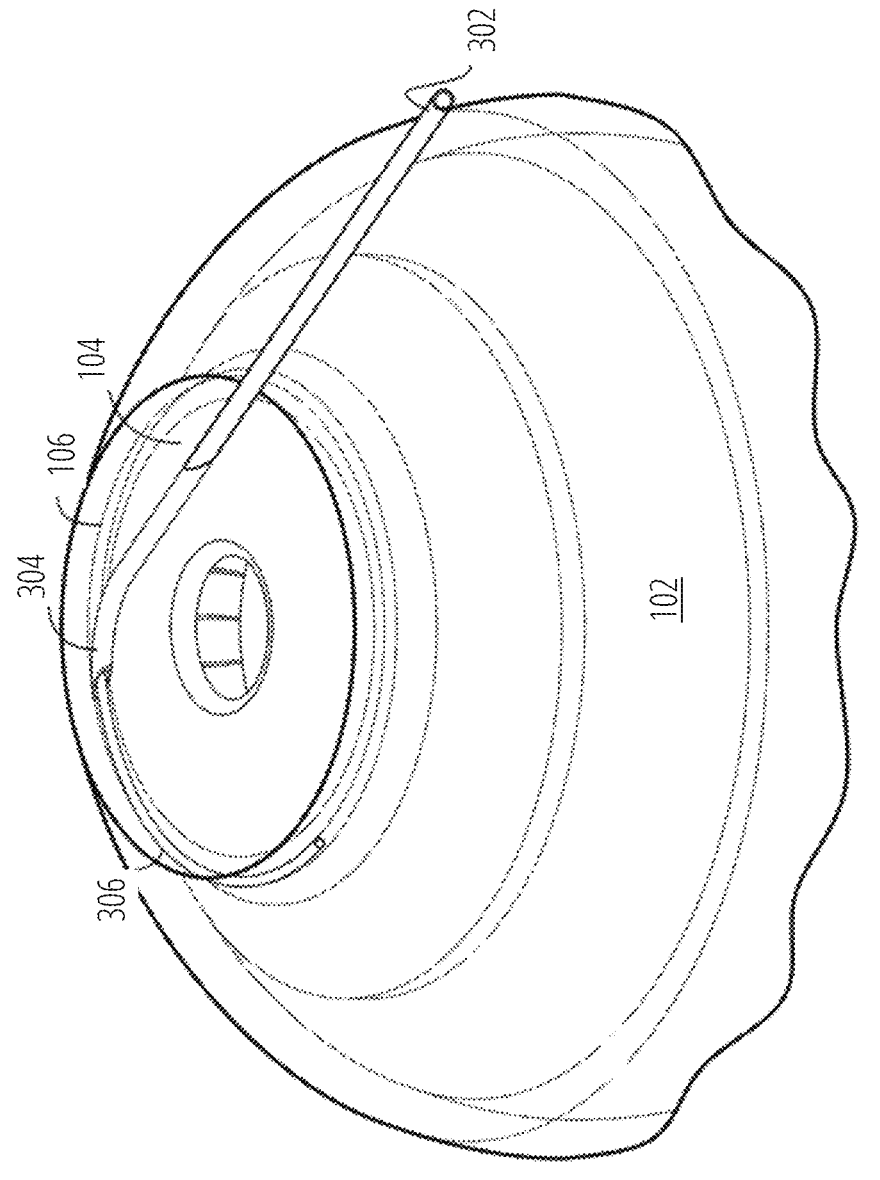
FIG. 3 illustrates an aspect of the subject matter in accordance with one embodiment.

FIG. 3 shows a perspective view of a microcatheter 302 advanced circumferentially within Schlemm's canal 104, shown traversing around the inner wall of the canal adjacent to the trabecular meshwork 106. The microcatheter 302 follows a curved path 304 and can be used to deliver various therapeutic agents 306 or materials along the canal circumference, including viscoelastic substances, endothelial cells embedded within hydrogel matrices, pharmaceutical drugs, diagnostic contrast agents, or gene therapy vectors.

Figure 4:
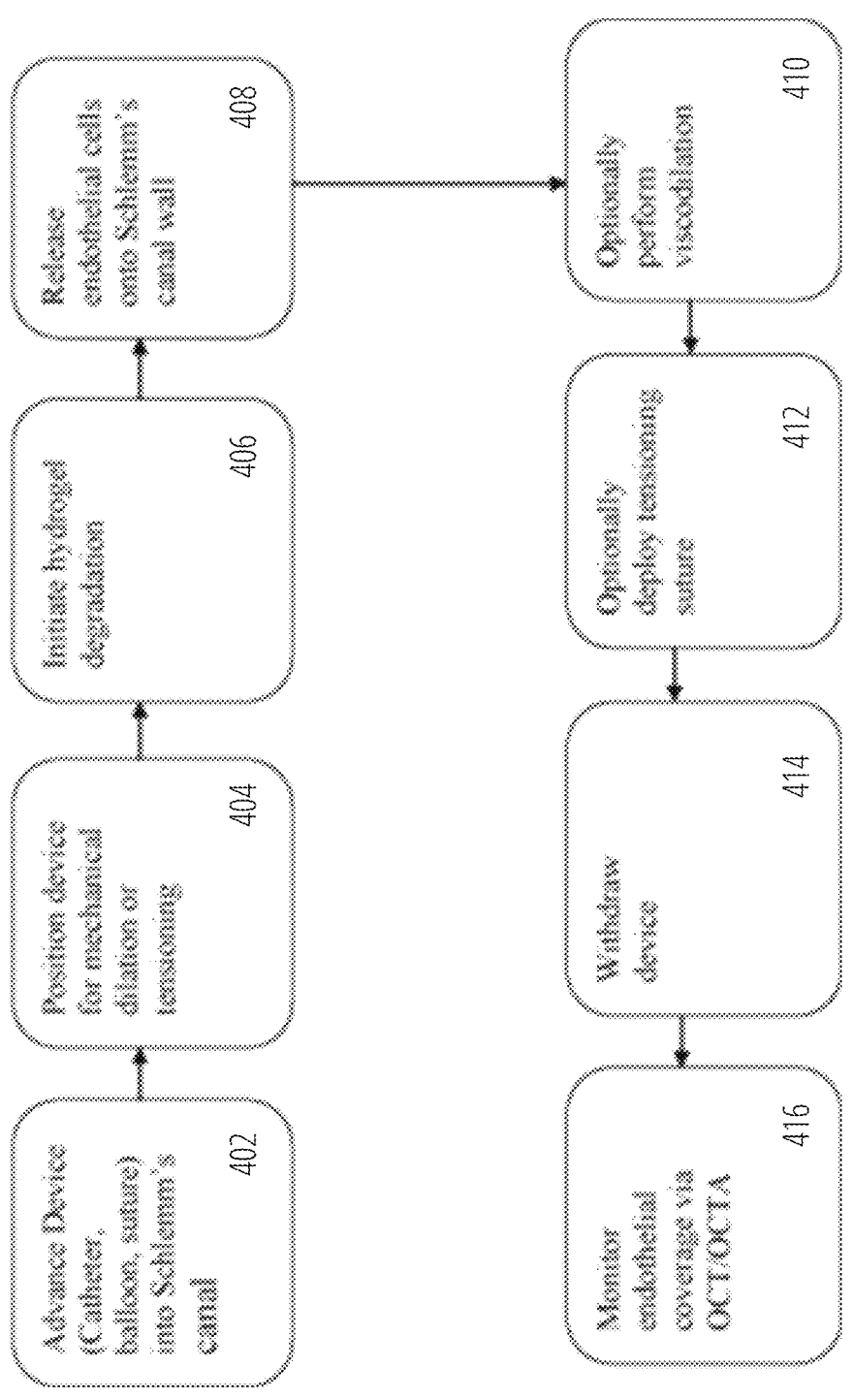
FIG. 4 illustrates a schematic block diagram illustrating an exemplary procedural workflow for endothelial cell delivery into Schlemm's canal.

FIG. 4 shows a schematic block diagram illustrating an exemplary procedural workflow for endothelial cell delivery into Schlemm's canal 104 using catheter-based or other advanced devices. In some scenarios, the existing endothelial cells that are dysfunctional or non-functioning are removed. This removal could be accomplished through surgical methods, such as scraping the inside of Schlemm's canal 104 with a micro-curette, micro-blade, or other micro-surgical instrument, or by using the viscoelastic 206 in combination with suctioning to dislodge and remove dysfunctional endothelial cells.

The procedural workflow may include advancing a delivery device 402, such as a microcatheter, balloon catheter, or tensioning suture system, into Schlemm's canal 104 and positioning it for therapeutic intervention 404. This could be by inserting the delivery device into an incision in the cornea 112 and Schlemm's canal 104. Next, the process may include the initiation of hydrogel degradation 406 and the release of endothelial cells 408. This may involve mechanical dilation, tensioning 412, or viscodilation 410. Endothelial cells may be delivered 408 through multiple methods, including infusion of an endothelial cell-loaded hydrogel directly through the catheter lumen, release of endothelial cells from an in situ-forming hydrogel matrix, or deployment of an endothelial cell-coated hydrogel sleeve mounted on the catheter exterior. Following endothelial cell transfer onto the canal wall 408, the delivery device is withdrawn 414, and optical coherence tomography (OCT) or OCT angiography (OCTA) may be used to monitor endothelial coverage, canal patency, and potential complications 416. When the device is then withdrawn 414, a tensioning suture 412 for performing additional viscodilation as indicated by the surgical plan may be deployed. This multi-modal approach enables both mechanical and biological enhancement of Schlemm's canal 104 to improve aqueous humor outflow and support regenerative treatment of glaucoma.

In certain embodiments, the delivery device may be introduced into Schlemm's canal 104 through a scleral incision (ab externo approach) rather than through a corneal incision (ab interno approach). A scleral entry site provides direct access to the canal and may be advantageous in cases where visualization or canaloplasty techniques are employed. This document therefore contemplates both ab interno and ab externo routes of access, including corneal, scleral, or other incisions that provide access to Schlemm's canal.

TABLE 1

| | Methods of Delivering Endothelial Cells in Canaloplasty | | | | |
|---|---|---|---|---|---|
| METHOD | DESCRIPTION OF DELIVERY | CELL TRANSFER MECHANISM | HYDROGEL ROLE | DEVICE CONSIDERATIONS | ENABLEMENT DETAILS |
| Hydrogel Coating on Catheter | Hydrogel layer pre-formed around catheter shaft and loaded with endothelial cells. | Cells contact canal wall during catheter advancement or withdrawal. | Acts as both lubricant and cell reservoir; may degrade to release cells gradually. | Diameter must remain < canal lumen (e.g. ~230 μm with coating). | Manufacturing enables precise coating |

TABLE 1-continued

| | | | | | |
|---|---|---|---|---|---|
| | Methods of Delivering Endothelial Cells in Canaloplasty | | | | |
| METHOD | DESCRIP- TION OF DELIVERY | CELL TRANSFER MECHANISM | HYDROGEL ROLE | DEVICE CONSIDER- ATIONS | ENABLEMENT DETAILS |
| Hydrogel Sleeve on Catheter | Hydrogel sleeve fabricated separately and slipped over catheter; loaded with endothelial cells. | Cells transferred via direct contact with canal wall as sleeve moves through canal. | Provides conformable fit; can swell slightly for better wall apposition. | Sleeve dimensions customizable intraoperatively to fit patient anatomy. | Sleeve wall thickness and cell loading tailored during manufacture or surgery; sleeves may be cryopreserved. |
| In Situ- Forming Hydrogel | Hydrogel precursor solution containing cells is injected through catheter into canal; polymerizes in place. | Cells embedded in gel matrix adhere to can.nl wall post- gelation. | Forms a hydrogel custom fit lining canal walls. | Requires precise gelation timing and safe polymerization kinetics. | Enables patient- specific adaptation; hydrogel formulations designed for fast, biocompatible curing. |
| Endothelial Cell Suspension Infusion | Free endothelial cell suspension injected directly into Schlemm's canal via catheter. | Cells settle and adhere to canal walls under fluidic forces and gravity. | None necessarily. may include low-viscosity carrier or minimal hydrogel additive. | Risk of cell washout if not paired with viscoelastic or gel carrier. | Requires control of infusion volume, flow rate, and cell concentration to achieve therapeutic cell densities. |
| Balloon Catheter Coating | Balloon surface coated with hydrogel loaded endothelial cells, balloon inflated in canal. | Inflation presses hydrogel (and cells) against canal wall for cell transfer. | Hydrogel layer facilitates adhesion under pressure. | Balloon diameter and pressure must avoid trauma. | Engineering ensures hydrogel withstands inflation while releasing cells effectively. |
| Tensioning Sutures Coated with Hydrogel | Sutures passed through canal with hydrogel coating containing endothelial cells. | As sutures tension or glide. cells contact canal wall. | Hydrogel enables cell retention and gradual release during manipulation. | Must balance suture handling with coating integrity. | Hydrogel chemistry designed for adhesion to suture fibers and controlled cell release. |

Table 1 provides a comprehensive summary of various embodiments for delivering endothelial cells into Schlemm's canal during canaloplasty procedures. Each method is described with respect to its delivery mechanism, the role of hydrogel (where applicable), device-specific considerations, and technical details supporting enablement. The listed techniques include pre-formed hydrogel coatings 602, hydrogel sleeves 204, in situ-forming hydrogels, endothelial cell suspensions, balloon catheter coatings, and tensioning sutures with hydrogel coatings 602. Key enablement factors for all embodiments include ensuring direct endothelial cell contact with the canal wall under surgical conditions, controlling hydrogel swelling behavior to maintain compatibility with the canal's lumen diameter (typically between 190 and 370 micrometers), and achieving precise cell densities (e.g., 2,500-3,500 cells per square millimeter of canal surface). Sterility, biocompatibility, and mechanical integrity are critical considerations across all embodiments to ensure safe and effective regenerative therapy.

1.0 TERMINOLOGY CLARIFICATION

As used throughout this application, the terms "conduit," "catheter," "microcatheter," and "device" 202 may be used interchangeably unless context clearly indicates otherwise. In many embodiments, this document relates to flexible tubular instruments capable of being advanced through Schlemm's canal 104 for diagnostic, therapeutic, or regenerative purposes. The term "conduit" is adopted broadly in this application to describe any such structure, regardless of whether it is used for mechanical manipulation, fluid delivery, cell delivery, viscodilation, or the combination of these functions. References to "catheter" or "microcatheter" 202 should be interpreted as including conduits of similar purpose or function. This convention is intended to promote clarity and to encompass the full scope of devices suitable for implementing the disclosed inventions across various commercial embodiments and surgical techniques.

Substrates vs. Additives: In the context of hydrogel-based Schlemm's canal 104 therapies, the term substrate refers to the primary material that forms the structural or functional base of a device, such as PEG or collagen, supporting the delivery of cells or therapeutic agents. By contrast, additives are secondary compounds incorporated into these substrates to enhance specific properties. These may include crosslinking agents, growth factors, imaging dyes, or anti-inflammatory drugs. While additives modulate the behavior of the hydrogel, they do not constitute the core material and are not considered substrates themselves. Distinguishing between substrates and additives is essential for accurate characterization and regulatory documentation of therapeutic devices.

The following detailed description sets forth exemplary embodiments of the inventions. All examples and embodiments are illustrative and are not intended to limit the scope of the inventions.

1.1 Overview of Endothelial Cell Therapy in Schlemm's Canal

This document provides systems, methods, and compositions for delivering endothelial cells into Schlemm's canal 104 to regenerate the canal's inner wall and restore physiological outflow of aqueous humor. Unlike purely mechanical MIGS devices, the system focuses on biological regeneration by repopulating Schlemm's canal 104 endothelium. The systems and methods encompass diverse delivery mechanisms and biological formulations designed to ensure safe, uniform, and clinically effective cell integration.

Schlemm's canal 104 is a delicate, circumferential vascular-like channel encircling the anterior chamber angle of the eye 102, situated just external to the trabecular meshwork 106. It plays a pivotal role in regulating intraocular pressure (IOP) by serving as a principal conduit for aqueous humor drainage from the anterior chamber into the collector channels and ultimately into the episcleral venous system.

The inner wall of Schlemm's canal 104 is lined with a specialized population of endothelial cells known as Schlemm's canal endothelial cells (SCECs). These cells exhibit unique characteristics, sharing features with both vascular endothelial cells and lymphatic endothelial cells, reflecting the canal's hybrid physiological function. Morphologically, they are flat, spindle-shaped, and interconnected by tight junctions, forming a semi-continuous monolayer that both regulates and facilitates fluid passage.

One hallmark of SCECs is their capacity to form transcellular pores and vacuolar channels, often referred to as giant vacuoles, which span the cytoplasm. These dynamic structures fluctuate in density and size in response to pressure gradients between the anterior chamber and the canal lumen. Through these transient pathways, aqueous humor passes from the juxtacanalicular tissue of the trabecular meshwork into Schlemm's canal 104. This transcellular transport is essential to maintaining proper IOP and physiological fluid balance.

Moreover, SCECs maintain critical interactions with the trabecular meshwork 106, both structurally and functionally. The trabecular meshwork 106 itself consists of collagenous and elastic beams covered with endothelial-like cells, forming a porous structure that progressively filters aqueous humor. As fluid traverses this meshwork, it faces increasing resistance, particularly in the juxtacanalicular connective tissue immediately adjacent to Schlemm's canal 104. SCECs act as a crucial final barrier and regulator, controlling the passage of aqueous humor into the canal and onward into the venous circulation.

The functional integrity of SCECs depends upon cell density and confluence, ensuring an intact monolayer that prevents abnormal flow pathways and uncontrolled fluid movement. The SCEC integrity also depends on cytoskeletal dynamics, enabling pore formation and modulation in response to varying IOP. Junctional integrity, maintaining selective permeability and preventing paracellular leakage impacts the functional integrity of the SCEC, as do extracellular matrix interactions, anchoring cells to the basal lamina, and preserving tissue architecture.

1.2 Causes of Dysfunction and Loss of Endothelial Cells

While primary open-angle glaucoma is a leading cause of SCEC loss and dysfunction, numerous additional factors can impair or reduce the viability of these critical cells, highlighting the broad clinical relevance of regenerative therapy for Schlemm's canal 104l.

1.3 Mechanical Trauma (Surgical and Iatrogenic)

Procedures such as trabecular goniotomy or trabeculotomy intentionally disrupt parts of the trabecular meshwork 106 and can inadvertently damage SCECs through scraping, tearing, or excessive manipulation. Similarly, viscodilation procedures, where viscoelastic substances are injected into Schlemm's canal 104 under pressure, can overstretch or rupture the delicate endothelial lining, especially if performed with high injection forces. Conduit advanced circumferentially within Schlemm's canal 104 can create frictional shear forces, potentially stripping endothelial cells from the Schlemm's canal 104 wall. Laser or energy-based MIGS procedures can generate thermal injury that extends beyond the trabecular meshwork 106 into Schlemm's canal 104, leading to collateral endothelial damage.

1.4 Medications and Chemical Exposure

Certain topical ocular medications, particularly those containing preservatives like benzalkonium chloride (BAK), exhibit cytotoxic effects. Chronic exposure may induce inflammation and compromise endothelial cell viability. Prolonged use of topical steroids can promote extracellular matrix accumulation and secondary outflow resistance, indirectly stressing SCECs. Although prostaglandin analogues are generally safe, they increase matrix metalloproteinase activity, which might affect the structural microenvironment surrounding SCECs.

1.5 Inflammatory or Autoimmune Disease

Inflammatory conditions such as uveitis expose Schlemm's canal 104l tissues to elevated cytokine levels, including interleukin-1 and tumor necrosis factor-alpha. This inflammatory milieu can trigger endothelial apoptosis or promote fibrotic remodeling, replacing functional endothelium with scar tissue.

1.6 Hemorrhage in Schlemm's Canal

Intraoperative or spontaneous hemorrhage can result in blood infiltration into Schlemm's canal 104. Breakdown products like iron can exert toxic effects on endothelial cells, while the presence of blood itself may provoke inflammatory and fibrotic responses, leading to canal stenosis or closure.

1.7 Elevated Intraocular Pressure

Even absent overt glaucoma, chronically elevated IOP can compress Schlemm's canal 104, distorting its geometry and impairing SCEC function. The mechanical stress reduces the formation of giant vacuoles and transcellular pores, further hindering fluid outflow.

1.8 Systemic Conditions

Systemic diseases like diabetes mellitus and hypertension may indirectly affect SCEC health. Microvascular changes, increased oxidative stress, and altered endothelial cell function associated with these conditions can predispose the canal to cellular injury or dysfunction.

1.9 Aging

Aging is associated with a natural decline in SCEC density and functionality. Structural stiffening of surrounding tissues increases mechanical strain on the canal wall, impairing the formation of giant vacuoles and leading to diminished outflow facility.

These diverse etiologies underscore the vulnerability of Schlemm's canal 104 endothelium and highlight the critical need for therapeutic strategies aimed at biological regeneration. Loss or dysfunction of SCECs contributes to increased outflow resistance, elevated IOP, and progressive optic nerve damage in glaucoma. Moreover, injuries to SCECs during MIGS or other ophthalmic procedures can compromise surgical outcomes, potentially leading to canal fibrosis, restenosis, or surgical failure.

104, including mechanical trauma from surgical interventions, chemical toxicity from topical medications, inflammatory and systemic diseases, and physiological stressors such as elevated intraocular pressure or aging. Each cause is

TABLE 2

| | | | | |
|---|---|---|---|---|
| Causes of Schlemm's Canal Endothelial Cell Loss or Dysfunction | | | | |
| Cause/ Category | Mechanism of Damage | Examples/Context | Possible Clinical Effects | Reversibility |
| Mechanical Trauma | Shearing, abrasion, stretching, tearing of SCECs | Microcatheter canaloplasty Trabecular goniotomy or trabeculotomy Balloon viscodilation Laser energy spillover | Local canal scarring Focal canal collapse Reduced outflow Increased risk of fibrosis | Partially reversible if mild; severe injury can cause permanent focal loss |
| Viscoelastic Over-pressurization | Excessive hydrostatic force rupturing endothelial lining | High-force OVD injections Uncontrolled viscodilation | Focal rupture of canal wall Blood reflux into canal Acute IOP spikes | Often reversible if transient, but repeated trauma may induce fibrosis |
| Topical Medication Toxicity | Chemical cytotoxicity, chronic inflammation | Long-term benzalkonium chloride (BAK) use Some preservatives | Subclinical inflammation Chronic endothelial stress | Reversible if exposure ceases early; prolonged toxicity may cause chronic damage |
| Steroid-Induced ECM Accumulation | Indirect stress from increased ECM deposition and outflow resistance | Chronic steroid therapy for ocular inflammation Post-surgical prophylaxis | Elevated IOP Reduced giant vacuole formation | Usually reversible if steroids withdrawn early; fibrosis risk if prolonged |
| Inflammatory/ Autoimmune Disorders | Cytokine-induced apoptosis or fibrotic remodeling | Juvenile idiopathic Uveitis (e.g. arthritis) Sarcoidosis Lupus | Local canal wall fibrosis Disrupted endothelial layer Increased outflow resistance | Partially reversible with anti-inflammatory treatment; permanent fibrosis if severe |
| Hemorrhage in Schlemm's Canal | Toxic effects from blood products (e.g. Iron), physical obstruction | Hyphema due to trauma or surgery Spontaneous micro-bleeds in fragile vessels | Fibrosis from hemosiderosis Local canal narrowing | Mild cases reversible; severe hemosiderosis can be permanent |
| Elevated IOP | Mechanical compression of canal, reducing pore formation | Angle closure Chronic Ocular hypertension episodes | Collapse of canal lumen Loss of transcellular pore density | Partially reversible if IOP controlled quickly; prolonged high IOP causes irreversible changes |
| Systemic Conditions | Microvascular damage, oxidative stress affecting endothelial health | Diabetes mellitus Hypertension Systemic vasculopathies | Increased canal wall rigidity Reduced endothelial cell proliferation Altered ECM remodeling | Often manageable with systemic disease control; severe changes may persist |
| Aging | Cellular senescence, loss of cytoskeletal plasticity, reduced repair capacity | Natural age-related decline | Fewer giant Thinning of endothelial layer vascuoles Reduced outflow facility | Gradual and irreversible; may be partially compensated by therapies |
| Genetic Disorders | Inherited defects in endothelial function or ECM composition | Rare syndromes affecting connective tissue | Increased glaucoma risk Structural canal anomalies | Depends on disorder, some genetic defects case permanent issues |

Table 2 summarizes a variety of factors known to cause loss or dysfunction of endothelial cells in Schlemm's canal associated with specific clinical contexts, mechanisms of injury, and varying degrees of reversibility. Recognition of these diverse etiologies underscores the vulnerability of Schlemm's canal 104 endothelium and highlights the clinical need for regenerative therapies, as disclosed herein, to restore or preserve endothelial function and maintain physiological aqueous humor outflow.

2.0 PHYSIOLOGICAL ROLE OF ENDOTHELIAL CELLS IN SCHLEMM'S CANAL AND REGENERATIVE THERAPY

Normal Schlemm's canal endothelial cells (SCECs) actively regulate aqueous humor outflow, responding to intraocular pressure (IOP) changes by adjusting transcellular pore density and forming dynamic fluid transport channels. In healthy eyes, SCEC density averages approximately 3,000 to 6,000 cells per square millimeter—a figure comparable to corneal endothelial density—forming a continuous monolayer that serves as both a semi-permeable barrier and a biomechanical interface between the trabecular meshwork 106 and collector channels.

dynamics, while excessive density may cause aggregation or obstruction of the canal lumen. This document addresses these challenges through engineered hydrogel delivery systems that support even cell distribution, regulate total effective bulk, and maintain canal patency within anatomical limits.

2.1 Dysfunction and Loss of Endothelial Cells

Diagnosis of Schlemm's canal 104 endothelial dysfunction remains clinically challenging, as direct visualization of endothelial cells in vivo is not yet achievable. Surgeons and clinicians must rely on indirect clues, including abnormal anterior segment imaging findings, reduced canal dimensions on OCT, poor surgical outcomes following MIGS procedures, and segmental outflow abnormalities detected by tracer-based techniques. While OCT and OCTA show promise for noninvasively assessing canal structure and flow, there remains an unmet need for regenerative approaches capable of restoring endothelial integrity, as disclosed herein, and for methods to dynamically monitor endothelial cell engraftment and function postoperatively.

TABLE 3

| Clinical Clue | Possible Underlying Cause | Clinical Presentation/ Observation | Specificity for SCEC Dysfunction |
|---|---|---|---|
| Reduced Response to IOP-Lowering Medications | SCECs unable to regulate outflow resistance effectively | Persistent elevated IOP despite multiple medications; limited TOP drop from aqueous suppressants of outflow enhancers | Moderate; can also occur in advanced TM fibrosis |
| Poor Outcome After MIGS | Pre-existing SCEC damage or fibrosis preventing new outflow pathways | Minimal or transient IOP lowering; early surgical failure | High; especially if no mechanical obstruction is seen |
| Canal Collapse on OCT | Loss of endothelial turgor, fibrotic remodeling | OCT imaging shows collapsed or narrowed Schlemm's canal lumen | Moderate; can also occur from pressure effects alone |
| Irregular Canal Contour on Imaging | Focal endothelial loss or fibrosis distorting canal walls | OCT or UBM reveals irregular shapes or partial obliteration | Moderate to high specificity |
| Hemorrhage During Surgery | Loss of endothelial barrier integrity; fragile canal wall | Reflux of blood into anterior chamber during goniotomy, trabeculotomy, or viscodilation | Moderate; minor bleeding may occur even in healthy eyes |
| Absent Episcleral Vein Blanching with Pressure | Loss of segmental flow due to endothelial dysfunction | No visible blanching or dye passage in certain canal segments during intraoperative or dye studies | High; reflects regional canal dysfunction |
| Intraoperative Smooth Wall Appearance | Fibrotic replacement of SCECs | Surgeon notes smooth, glistening canal wall lacking normal vascular markings | High specificity for endothelial or tissue loss |
| History of Chronic Inflammation or Medications | Chronic subclinical injury to SCECs | Patient history of uveitis, long-term steroids, or toxic preservative use | Indirect; raises suspicion but not diagnostic |

These cells secrete extracellular matrix molecules and enzymes that regulate the resistance of the juxtacanalicular tissue, maintain low outflow resistance, and contribute to local immune homeostasis. When SCEC populations are depleted or dysfunctional, pore formation is reduced, paracellular leakiness may increase, and perfusion becomes irregular or obstructed. This leads to elevated IOP and downstream glaucomatous injury.

For regenerative therapy, restoring SCEC density within the physiological range is critical. Both underpopulation and overpopulation can be detrimental; insufficient cell seeding may result in inadequate coverage and impaired fluid Table 3 summarizes clinical clues and intraoperative findings that may raise suspicion for dysfunction or loss of Schlemm's canal endothelial cells. While some indicators, such as irregular canal imaging or poor MIGS outcomes, are strongly suggestive of endothelial damage, other factors, like hemorrhage or a history of ocular inflammation, provide important contextual evidence. Recognition of these patterns can inform surgical planning, prognosis, and the potential utility of regenerative therapies, as disclosed herein.

2.2 Bleeding as a Clinical Sign of Schlemm's Canal Endothelial Cell Dysfunction

Bleeding within Schlemm's canal 104, particularly when observed during surgical interventions such as canaloplasty, trabecular goniotomy, or conduit-based procedures, serves as a potential clinical indicator of an underlying endothelial cell loss or dysfunction.

Under normal physiological conditions, Schlemm's canal 104 is lined by a continuous layer of specialized endothelial cells that form a semi-permeable barrier between the canal lumen and adjacent vascular structures, including collector channels and episcleral veins. These endothelial cells play a crucial role in preventing reflux of blood into the canal, maintaining controlled passage of aqueous humor, and preserving the integrity of intraocular pressure dynamics.

However, when this endothelial layer is compromised, whether through disease processes such as glaucoma, mechanical trauma during surgery, chronic inflammation, or exposure to cytotoxic medications, the barrier function becomes weakened. The loss or disruption of tight junctions and cellular cohesion allows blood from neighboring vascular structures to reflux into Schlemm's canal 104 and potentially into the anterior chamber.

Bleeding during canal-based surgeries can thus serve as a real-time intraoperative clue that the endothelial lining is damaged or absent. While minor hemorrhage is relatively common and often occurs even in otherwise healthy eyes due to delicate microvascular networks in the angle, excessive, spontaneous, or widespread bleeding is more concerning. Such hemorrhage often suggests a loss of endothelial integrity, allowing direct communication between Schlemm's canal 104 and episcleral or collector channel vasculature, fragility of the canal wall, possibly due to underlying fibrosis or scarring that has replaced healthy endothelial cells, and elevated pressure gradients between Schlemm's canal 104 and adjacent blood vessels, exacerbated by loss of regulatory endothelial mechanisms.

Surgeons may note this bleeding as a sudden reflux of blood into the anterior chamber when the canal is opened, dilated, or manipulated. Intraoperatively, the presence of smooth, glistening canal walls lacking normal vascular markings may further suggest prior endothelial loss, particularly if accompanied by hemorrhage.

Importantly, while bleeding is an indicator, it is not exclusively diagnostic of endothelial cell absence. Minor or focal hemorrhage can occur due to mechanical microtears during conduit passage, physiologic pressure changes during viscodilation, or surgical instrument contact with delicate angle structures.

Thus, bleeding should be interpreted in context, considering the extent, spontaneous nature, and persistence of hemorrhage, alongside other clinical and imaging findings. Nonetheless, significant bleeding during Schlemm's canal 104 procedures is a clinically relevant sign that the canal's endothelial barrier has been disrupted, underscoring the potential benefit of regenerative approaches to restore endothelial integrity and maintain physiological aqueous humor outflow.

TABLE 4

Hemorrhage during Goniotomy or Canaloplasty Can Be a Clue that
Schlemm's Canal Endothelium is Compromised

| Physiological Condition or Event | Mechanism or Explanation | Clinical Implications |
| --- | --- | --- |
| Healthy SCECs present | Form a semipermeable barrier between Schlemm's canal and adjacent blood | Minimal or no blood reflux into Schlemm's canal during routine |

TABLE 4-continued

Hemorrhage during Goniotomy or Canaloplasty Can Be a Clue that
Schlemm's Canal Endothelium is Compromised

| Physiological Condition or Event | Mechanism or Explanation | Clinical Implications |
| --- | --- | --- |
| | vessels, maintaining controlled separation even during pressure fluctuations | surgical manipulation; canal integrity preserved. |
| Damage or absence of SCECs | Disruption of tight junctions and cellular cohesion breaks the barrier function, creating direct communications between Schlemm's canal and blood vessels | Blood can reflux easily into Schlemm's canal or anterior chamber during surgical maneuvers, even with modest pressure changes. |
| Excessive hemorrhage during canal-based surgery | Indicates compromised endothelial lining, fragile canal wall, or abnormal vascular connections (e.g. Neovascularization or fibrosis replacing endothelium) | Suggests prior endothelial injury, potentially higher risk of surgical failure, fibrosis, or restenosis postoperatively. |
| Minor focal bleeding | Often due to mechanical microtears, instrument contact, or physiologic pressure changes during surgery | Common and typically not clinically significant if self-limited; not necessarily diagnostic of underlying endothelial loss. |
| Smooth, glistening canal walls observed intraoperatively | May reflect fibrotic replacement of healthy endothelium, lacking normal vascular patterning. | Raises suspicion for prior endothelial loss and potential long-term compromise of canal function. |

Table 4 highlights how hemorrhage encountered during goniotomy or canaloplasty may serve as an indicator of Schlemm's canal 104 endothelial compromise. While minor bleeding is frequently observed and often benign, excessive or spontaneous hemorrhage often suggests underlying endothelial disruption, canal fragility, or pathological remodeling such as fibrosis or neovascularization. Recognition of this intraoperative sign is critical in identifying patients who may benefit from endothelial regenerative therapies as disclosed herein.

3.0 RATIONALE FOR REGENERATIVE ENDOTHELIAL CELL THERAPY

Given these vulnerabilities, the biological regeneration of Schlemm's canal 104 endothelium represents a novel therapeutic approach. Rather than merely creating a mechanical pathway for fluid drainage, this document envisions reestablishing a viable, functional endothelial cell layer within Schlemm's canal 104. Delivered endothelial cells are intended to re-form transcellular pores and giant vacuoles essential for physiological fluid outflow; secrete regulatory molecules that modulate extracellular matrix turnover and prevent fibrosis; maintain barrier integrity while dynamically responding to changes in IOP; and promote sustained canal patency and reduce the risk of surgical failure or progressive glaucomatous damage.

By integrating endothelial cell therapy with MIGS procedures, the techniques seek to deliver not only immediate surgical efficacy but long-term restoration of physiological outflow. The systems and methods disclosed herein aim to preserve or restore the natural architecture and function of Schlemm's canal 104*l*, thereby achieving more sustainable IOP control and reducing the risk of progressive glaucomatous damage.

3.1 Platform for Advancement

This document is envisioned not merely as a single device or treatment method, but as a platform technology capable of evolving alongside evolving developments in ophthalmic surgery and biomedical engineering. While initially described for regenerating Schlemm's canal 104 endothelium in the context of canaloplasty or minimally invasive glaucoma surgeries (MIGS), the foundational principles, namely, the delivery of viable endothelial cells 208 via biocompatible materials such as hydrogels, are inherently adaptable to a broad spectrum of ophthalmic interventions.

This platform concept anticipates that a variety of future devices or procedural tools, many of which have not yet been described in the literature, could be developed to interface with Schlemm's canal 104. These might include new types of conduit with advanced steering capabilities, smart devices capable of real-time pressure sensing and feedback, biodegradable scaffolds designed to maintain canal patency while simultaneously delivering therapeutic cells, evolving implants with integrated drug or cell release functions, and robotics-assisted devices offering ultra-precise deployment of biological payloads.

By designing a biologically integrated system, it can be modularly combined with both existing and future technologies. For instance, the hydrogel sleeves 204 or hydrogel coatings 602 described herein could be adapted to conform to new geometries or mechanical profiles of emerging surgical tools. The endothelial cell formulations could likewise be tailored to meet requirements of new delivery mechanisms or combined therapies.

This platform approach ensures that the system remains adaptable and compatible with evolving devices and surgical techniques.

3.2 Device-Based Delivery Embodiments

The present document encompasses methods for delivering endothelial cells 208 into Schlemm's canal 104 to facilitate regeneration of its endothelial lining and restore physiological aqueous humor outflow. In particular, the system contemplates the use of hydrogel and other materials as carriers and protective matrices for endothelial cell delivery. These hydrogels may be provided in two principal formats, both of which fall within the scope of this document.

In some embodiments, the hydrogel is pre-formed as a sleeve or coating manufactured onto the exterior surface of a conduit prior to surgical use, ensuring precise control over coating thickness, cell loading, and mechanical characteristics.

In other embodiments, the hydrogel layer is designed to form in situ during the surgical procedure itself, whereby liquid hydrogel precursors are applied around the conduit within Schlemm's canal 104 and subsequently undergo gelatin or polymerization to create a conformal coating. Both pre-formed and in situ-formed hydrogel approaches are contemplated as versatile and complementary strategies for achieving safe, uniform, and effective endothelial cell delivery within the anatomical constraints and procedural dynamics of Schlemm's canal 104 interventions.

Deployment and Disengagement Methodology of Hydrogel Sleeve from Canaloplasty Catheter In the disclosed embodiment, the hydrogel sleeve is preloaded onto the distal segment of a flexible canaloplasty catheter. The methodology of deployment and disengagement includes the following steps: |

1. Preparation and Insertion. The hydrogel sleeve 204, in a dehydrated or semi-hydrated compressed state, is affixed circumferentially around the distal shaft of the catheter 202. The catheter 202 is inserted ab interno through a corneal incision into Schlemm's canal 104 using standard microcatheterization techniques. Navigation through the canal may be facilitated by viscoelastic injection, transillumination, or OCT guidance. In other embodiments, ab externo routes of access, including corneal, scleral, or other incisions may provide access to Schlemm's canal.

2. Advancement through Schlemm's canal 104. As the catheter 202 advances circumferentially through Schlemm's canal 104, the hydrogel sleeve 204 remains secured due to a frictional fit or temporary biodegradable tethering. The hydrogel remains in a compact state to minimize canal trauma and preserve visibility and control.

3. Controlled Hydration and Expansion. Upon reaching the intended delivery site, commonly a segment spanning 90° (one quarter of the length of Schlemm's canal 104) to 180° (one half of the length), a hydration trigger is initiated. This may be achieved through passive absorption of aqueous humor, controlled infusion of sterile saline or BSS via an integrated lumen, or local application of a hydrating agent using a dual-lumen catheter 202 design. Hydration activates the hydrogel, causing it to swell and gently press against the trabecular meshwork 106 and inner wall of Schlemm's canal 104.

4. Disengagement Mechanism. Once the hydrogel sleeve 204 has fully expanded and anchored to the canal wall, disengagement from the catheter 202 is facilitated by catheter retraction: the gentle withdrawal leaves the hydrogel sleeve 204 in situ; sheath-assisted release: a retractable external sheath is removed first, forcing the sleeve; thermoresponsive or Enzymatic Release: a dissolvable tether disengages the sleeve once deployed.

5. Post-Deployment Positioning and Confirmation. Following deployment, the hydrogel sleeve 204 conforms to the Schlemm's canal 104 curvature, optionally releasing therapeutic agents and facilitating endothelial cell migration. OCT imaging or gonioscopy may be used to confirm appropriate placement and canal patency.

3.3 Endothelial Cell Seeding Versus Native Regeneration

In certain embodiments, the hydrogel-based hydrogel sleeve 204 may optionally incorporate pre-seeded endothelial cells 208 on its surface to further enhance tissue integration and accelerate Schlemm's canal 104 regeneration. Such embedded cells may include autologous or allogenic Schlemm's canal endothelial cells or endothelial-like cells derived from limbal progenitors or induced pluripotent stem cells. These seeded cells may promote rapid endothelial coverage, secrete anti-fibrotic mediators, and support early canal patency. However, it is recognized that the native Schlemm's canal 104 environment contains a resident population of endothelial cells capable of repopulating the hydrogel surface through guided migration. The hydrogel may be engineered with integrin-binding peptides, such as RGD, and loaded with nitric oxide donors, VEGF mimetics, or extracellular matrix analogs to recruit and align native cells without requiring pre-seeding. Given that Schlemm's canal endothelial cells typically migrate at approximately 100 microns per day, complete surface coverage of the scaffold may occur within 10-14 days post-implantation. This suggests that while endothelial cell embedding may improve outcomes in certain high-risk or fibrotic settings, it is not essential for achieving optimal Clinical performance. A bioactive, cell-free hydrogel may offer a more scalable, off-the-shelf therapeutic platform with comparable long-term benefit.

TABLE 5

Comparison of Cell-Seeded vs. Cell-Free Hydrogel Strategies

| Feature | Cell-Seeded Hydrogel | Cell-Free, Bioactive Hydrogel |
|---|---|---|
| Endothelial coverage speed | Immediate (pre-attached cells) | Rapid via SCEC migration (~10-14 days) |
| Regenerative signaling | Endothelial-secreted NO, cytokines | Drug-loaded hydrogel (NO donors, VEGF) |
| Integration with host tissue | High, especially in scarred tissue | High with appropriate ECM mimicry |
| Production complexity | Requires GMP cell sourcing and viability maintenance | Simplified, off-the-shelf manufacturing |
| Shelf life and storage | Limited; refrigeration or cyropreservation required | Extended; dry or hydrated formats possible |
| Clinical scalability | Challenging due to regulatory and logistical hurdles | Favorable for wide distribution and use |

Table 5 shows the strategic comparison of Endothelial cell-seeded versus bioactive cell-free hydrogels for canal-based regenerative therapy. Table 5 presents a comparative analysis of two approaches to promoting endothelial regeneration within Schlemm's canal 104: (1) hydrogel scaffolds pre-seeded with endothelial cells 208, and (2) bioengineered, cell-free hydrogels that stimulate endogenous repair through molecular and structural cues. Key performance indicators include the speed of endothelial coverage, mechanisms of regenerative signaling, integration with host tissues, and practical considerations such as manufacturing complexity, storage requirements, and scalability. The comparison underscores that while cell-seeded constructs may confer early advantages in select clinical scenarios, bioactive acellular hydrogels offer compelling benefits in terms of production simplicity, logistical feasibility, and widespread therapeutic deployment.

4.0 SUBSTRATES FOR REGENERATIVE ENDOTHELIAL CELL THERAPY

Hydrogel represents an ideal substrate material for use in Schlemm's canal therapies due to its unique combination of biocompatibility, tunable mechanical properties, and ability to serve as a carrier for both cellular and pharmacological agents. When designed with appropriate swelling characteristics, hydrogels can conform gently to the lumen of Schlemm's canal 104, minimizing trauma while providing a stable interface for therapeutic interaction with surrounding tissue.

As a primary material for endothelial cell delivery, hydrogel supports cellular viability by offering a hydrated three-dimensional matrix that mimics native extracellular environments. This facilitates nutrient exchange, promotes cell adhesion, and enables gradual engraftment into the canal wall. The inherent porosity of certain hydrogel formulations allows for diffusion of oxygen, glucose, growth factors, and signaling molecules essential for endothelial cell survival and integration. In this setting, hydrogel may be used as a fully formed conduit or microcatheter, delivering cells directly while maintaining structural compatibility with the canal's delicate architecture.

In other embodiments, hydrogel may function as a coating or sleeve applied to devices fabricated from structurally supportive materials such as Nitinol. This hybrid approach combines the mechanical resilience of the core material with the biologic functionality of the hydrogel layer. The hydrogel coating 602 acts as a bioactive interface, enabling the sustained delivery of nutrients, anti-inflammatory agents, or endothelial cells 208. This layered system supports controlled release profiles, protects the canal from shear-induced damage, and may be tailored to degrade over time, gradually transferring therapeutic agents into the canal wall.

One of the most widely used hydrogel materials in biomedical applications is polyethylene glycol (PEG). PEG is a synthetic, hydrophilic polymer known for its high biocompatibility, non-immunogenicity, and customizable properties. PEG-based hydrogels offer excellent water retention and mimic natural tissue environments, supporting cell survival and nutrient diffusion. They can be chemically crosslinked to form stable, tunable matrices that gel in situ, and can be engineered to degrade at controlled rates. These features make PEG an optimal candidate for forming hydrogel sleeves 204 or hydrogel coatings 602 that deliver endothelial cells 208 or nutrients into Schlemm's canal 104. Furthermore, PEG hydrogels are compatible with injectable formats and can be combined with other materials and agents to enhance therapeutic versatility.

Whether used alone or in conjunction with another material, hydrogel enhances the adaptability and safety of Schlemm's canal therapies. It provides a versatile platform capable of delivering regenerative therapies with minimal invasiveness, while enabling synergy with imaging guidance and artificial intelligence systems for optimized dosing and procedural execution. As such, hydrogel addresses both the mechanical and biological requirements of effective canal-based glaucoma intervention.

4.1 Comparison of PEG Hydrogel with Alternative Substrates

While polyethylene glycol (PEG) hydrogels are highly regarded for their tunability and compatibility with Schlemm's canal therapy, other hydrogel and polymeric materials have also been explored for use in similar ophthalmic applications.

One alternative is hyaluronic acid (HA), a naturally occurring glycosaminoglycan with strong biocompatibility and water retention. HA has the advantage of being recognized by native cell receptors. However, HA degrades more rapidly than PEG and offers less control over mechanical stiffness and crosslinking behavior. This limits its utility for long-duration cell delivery or structural coating applications.

Another material, alginate, is derived from seaweed and forms hydrogels through ion-induced gelation. While alginate can be used for cell encapsulation and is considered biocompatible, its degradation is difficult to finely tune, and it often lacks the mechanical integrity necessary for use in narrow, pressurized microenvironments like Schlemm's canal 104.

Collagen-based hydrogels more closely mimic extracellular matrix composition and support cell attachment. However, they can be immunogenic depending on the source, degrade unpredictably, and are prone to batch-to-batch variability, making regulatory standardization more difficult compared to PEG.

Synthetic alternatives like polyvinyl alcohol (PVA) and polylactic-co-glycolic acid (PLGA) can offer enhanced mechanical strength or delayed degradation but typically lack the same level of hydrophilicity and cell-friendly microenvironment found in PEG. Moreover, degradation byproducts from PLGA can be acidic and inflammatory. In summary, PEG hydrogels combine structural tunability, predictable degradation, non-immunogenicity, and customizable biofunctionality in a way that uniquely suits the anatomic and therapeutic demands of Schlemm's canal intervention. Their compatibility with in situ gelation, imaging contrast enhancement, and AI-optimized delivery protocols further solidifies their role as the preferred substrate for the hydrogel-enabled systems.

TABLE 6

Example of types of Hydrogel

| Hydrogel Type | Composition | Longevity (in vivo) | Key Features |
|---|---|---|---|
| PEG-based (Polyethylene Glycol) | Synthetic, biocompatible | Days to months (tunable) | Chemically stable, customizable degradation via hydrolysis or enzymatic triggers |
| HA-based (Hyaluronic Acid) | Natural, polysaccharide | Hours to weeks (enzyme-labile) | Biodegradable by hyaluronidase; fast resorption unless chemically modified |
| PVA-based (polyvinyl Alcohol) | Synthetic, water-soluble | Weeks to months (non-degradable unless modified) | Stable in aqueous environments; often used with physical crosslinking |
| Gelatin-based | Denatured collagen protein | Houses to days | Rapidly degraded by proteases; suitable for short-term delivery |
| Alginate-based | Seaweed-derived polysaccharide | Days to weeks | Ionically crosslinked; moderately stable but mechanically weak |
| Fibrin gels | Blood-derived protein network | <1 week | Quickly resorbed by proteolysis; highly biocompatible but short-lived |
| Chitosan-based | Derived from crustacean shells | Weeks to months | Biodegradable, mucoadhesive; degradation via lysozymes |
| Self-assembling peptide gels | Short peptides forming nanofibrous networks | Days to weeks | Tunable degradational used in regenerative medicine |

TABLE 7

Additives Supporting Transfer of Schlemm's Canal Endothelial Cells

| Additive | Function | Notes/Use Case |
|---|---|---|
| Fibrinogen/ Thrombin | Gelation and temporary matrix for cell adherence | Used to stabilize cells during injection |
| RGD Peptides | Promotes cell adhesion to matrix | Supports integrin-mediated binding during transfer |
| Hyaluronic Acid | Viscosity agent and hydration support | Facilitates smooth injection and minimizes shear stress |
| Collagen Type I | Scaffold support | Provides ECM-like environment during cell transit |
| Trehalose | Osmoprotectant | Protects cell membranes during handling and delivery |
| Albumin | Carrier protein | Stabilizes cells and prevents aggregation |

TABLE 7-continued

Additives Supporting Transfer of Schlemm's Canal Endothelial Cells

| Additive | Function | Notes/Use Case |
|---|---|---|
| Poloxamer 407 | Thermosensitive gelling agent | Enables in situ gelation upon warming to body temperature |

Table 7 lists biological and chemical additives that facilitate the safe and effective transfer of endothelial cells through Schlemm's canal. These additives enhance cell viability, promote adhesion, and reduce mechanical stress during injection or conduit-based delivery.

In a particular embodiment, the disclosed hydrogel implant comprises a tubular, microporous scaffold constructed of PEG-based core polymers with an outer bioactive matrix of HA or gelatin, engineered for biodegradable support of Schlemm's canal 104. The device is enhanced with surface nanostructures and peptide ligands to promote endothelial migration, and may further incorporate embedded therapeutic agents or seeded endothelial cells to accelerate physiologic restoration. Designed for temporary deployment in Schlemm's canal 104, the device supports long-term canal patency and aqueous outflow through short-term modulation of the tissue environment, as substantiated by clinical analogs, tissue engineering evidence, and mathematical modeling.

4.2 Hydrogel Substrates for Cell Viability and Nutrient Exchange

In certain embodiments, hydrogels used as coatings or sleeves for conduits in Schlemm's canal 104 are formulated to include specialized substrates designed to support the viability, metabolic function, and maintenance of endothelial cells during storage, surgical handling, and in situ residence within the canal. Because endothelial cells are metabolically active and sensitive to nutrient deprivation, maintaining their physiological health is critical to achieving effective regenerative outcomes.

Hydrogel substrates may incorporate biopolymers such as hyaluronic acid, gelatin, collagen, or fibrin, which serve both as physical scaffolds and as bioactive environments that facilitate cell attachment, survival, and function. These materials possess inherent bioactivity through specific integrin-binding domains (e.g., RGD sequences in gelatin and collagen) that promote endothelial cell adhesion and spreading, thereby helping cells maintain their phenotype and viability during implantation. Additions to the substrate may include one or more additives selected from a group of endothelial adhesion peptides, including but not limited to pentapeptides, growth factors, or nutrient factors, suitable for enhancing Schlemm's canal endothelial cell viability or integration.

Moreover, hydrogels may be loaded with low concentrations of soluble nutrients, growth factors, and antioxidants to enhance cell survival during ex vivo storage and early postoperative periods. For instance, substrates may include components such as glucose, amino acids, vitamins, or specific trophic factors like VEGF (vascular endothelial growth factor) and bFGF (basic fibroblast growth factor), which are known to promote endothelial cell proliferation and resistance to oxidative stress. Controlled release of these nutrients ensures that endothelial cells 208 embedded within the hydrogel remain viable even in the transiently avascular environment of Schlemm's canal 104 immediately following implantation.

Importantly, hydrogel matrices can be engineered to exhibit controlled permeability, allowing the passive diffusion of nutrients from surrounding ocular tissues and aqueous humor into the hydrogel layer while simultaneously permitting metabolic waste products to diffuse outward. This balance of nutrient influx and waste efflux is essential to prevent localized cell hypoxia, acidosis, or toxic metabolite accumulation, which could compromise cell function or viability.

TABLE 8

Additives Supporting Existing Schlemm's Canal Endothelial Cells

| Additive | Function | Notes/Use Case |
|---|---|---|
| VEGF (low dose) | Supports endothelial cell survival | Used cautiously to avoid neovascularization |
| bFGF (Basic Fibroblast Growth Factor) | Promotes proliferation and repair | May support endothelial regeneration |
| Hydrocortisone | Reduces inflammation | Protects against inflammatory loss postoperatively |
| S1P (Sphingosine-1-phosphate) | Enhances barrier function and cell survival | Stabilizes junctions |
| Nitric Oxide Donors | Enhance vasodilation and flow | May stimulate endogenous repair |
| Ascorbic Acid (Vitamin C) | Antioxidant and cofactor in collagen synthesis | Supports cellular repair and homeostasis |
| Dexamethasone (low-dose) | Anti-inflammatory steroid | Prevents immune-mediated injury without overwhelming suppression |

Table 8 presents additives that help maintain and stabilize the native endothelial lining of Schlemm's canal. These agents promote cellular survival, reduce inflammation, and support tissue repair in post-treatment or regenerative settings.

4.3 Hydrogel Substrates for Therapeutic Agent Delivery

In further embodiments, hydrogel coatings 602 or hydrogel sleeves 204 function not only as cellular delivery matrices but also as controlled-release vehicles for pharmaceutical agents intended to modulate the biological environment within Schlemm's canal 104. The hydrogel network can be loaded with therapeutic substances including, but not limited to, anti-fibrotic agents (e.g., mitomycin-C, pirfenidone), anti-inflammatory drugs (e.g., corticosteroids, nonsteroidal anti-inflammatory agents), or pro-regenerative compounds (e.g., transforming growth factor beta inhibitors, matrix metalloproteinase inhibitors).

Such therapeutic agents may be incorporated into the hydrogel by physical entrapment, ionic interactions, or covalent conjugation to the hydrogel backbone. The release profile of these agents can be finely tuned by modifying the hydrogel's crosslink density, hydrophilic-hydrophobic balance, or by embedding nanoparticles or microparticles within the hydrogel matrix to serve as secondary reservoirs for drug storage and gradual release.

Importantly, therapeutic loading may be performed with or without concurrent endothelial cell incorporation. In some embodiments, hydrogels serve purely as pharmaceutical delivery devices, devoid of cells, to create a localized pharmacologic microenvironment aimed at preventing postoperative scarring, controlling inflammation, or modulating tissue remodeling after canaloplasty procedures. In other embodiments, hydrogels simultaneously deliver both viable endothelial cells 208 and pharmaceutical agents, leveraging a combined mechanical, cellular, and pharmacologic therapeutic strategy.

For example, a PEG-based hydrogel sleeve may be preloaded with endothelial cells 208 at a density of approximately 3,000 cells/mm$^2$ while also carrying a low dose of mitomycin-C intended to inhibit fibroblast proliferation and scar formation in the surgical site. The hydrogel's controlled swelling and gradual degradation enable a sustained release of both cells and therapeutic agents, maximizing the regenerative and anti-fibrotic benefits of the treatment.

The incorporation of pharmaceutical substrates into hydrogel systems provides a crucial adjunct to mechanical and cellular strategies, further supporting the regenerative goals by reducing postoperative complications and enhancing long-term canal patency and function.

Radiopaque markers incorporated in the sleeve, coating, or shaft of a conduit can assist in identifying a device. Multiple coatings on a conduit, sleeve, or other device that enters Schlemm's canal 104 may be spaced along the conduit for sequential delivery. Pre-seeded endothelial cells 208 may be protected in a gelatin coating that dissolves post-deployment to enhance survival.

4.4 Hydrogel Sleeve Integrated with Endothelium

In certain embodiments, a hydrogel sleeve is pre-formed ex vivo and either manufactured directly onto the conduit or configured as a separate tubular structure that can be slid over the conduit shaft prior to the surgical procedure. This hydrogel sleeve is fabricated with an inner diameter precisely sized to fit snugly around the conduit and an outer diameter suitable for safe passage through Schlemm's canal 104, thereby ensuring compatibility with the anatomical dimensions and preserving fluid dynamics necessary for proper canal function.

The hydrogel sleeve 204 may be formed from highly transparent polyethylene glycol (PEG)-based hydrogels, which facilitate visual confirmation of the sleeve's placement and alignment with underlying conduit markings. Alternatively, translucent hydrogel formulations may be employed, particularly when preloaded with endothelial cells 208 or therapeutic agents, where minor optical haze is acceptable without compromising surgical visualization.

Beyond hydrogels, the endothelial cell delivery sleeve can be fabricated from various alternative materials, including biodegradable polymers, electrospun fiber matrices, natural biopolymers, thermoplastic elastomers, or shape-memory polymers. These materials are chosen based on their biocompatibility, ability to support cell viability, mechanical flexibility, and dimensions suitable for navigation within Schlemm's canal 104.

The manufacturing process leverages established industrial techniques such as dip-coating, spray-coating, extrusion, or molding to produce hydrogel sleeves 204 with highly uniform thickness and reproducible physical and biological properties. The typical wall thickness of the hydrogel sleeve 204 ranges between 10 and 30 micrometers per side, depending on the desired cell payload and mechanical robustness. For example, a hydrogel sleeve 204 with a 10-micrometer wall thickness per side fitted onto a 200-micrometer bare conduit results in a total outer diameter of approximately 220 micrometers. A 15-micrometer wall thickness yields a diameter of around 230 micrometers, while a thicker sleeve of 30 micrometers per side results in a diameter near 260 micrometers. These dimensions remain compatible with most commercially available introducer lumens, which generally possess internal diameters between 250 and 300 micrometers.

Critical to the safe performance of hydrogel sleeves 204 is the need to minimize volumetric swelling upon hydration. Preferred hydrogel chemistries for this application exhibit swelling behavior below approximately 10-15% to prevent potential canal lumen obstruction during or after implantation.

A key advantage of hydrogel sleeves 204 is their capacity to be preloaded ex vivo with endothelial cells 208 under sterile conditions, thus enabling the conduit to serve as both a mechanical navigation tool and a biological delivery platform for regenerative therapy. The hydrogel matrix functions as a protective medium preserving cell viability and as a controlled-release reservoir that gradually delivers endothelial cells 208 and therapeutic agents into the canal wall. This dual-purpose design transforms conventional canaloplasty conduits into active regenerative devices capable of restoring physiological endothelial cell coverage and function.

Following complete circumferential or segmental navigation of Schlemm's canal 104l, the hydrogel sleeve 204 may be released from the conduit either mechanically or through mechanisms such as swelling, softening, or enzymatic cleavage. Once released, the hydrogel sleeve 204 remains in place within Schlemm's canal 104, where it gradually degrades and facilitates uniform endothelial cell delivery along the canal circumference. Possible release mechanisms include friction-based retention during conduit withdrawal, hydrogel expansion upon exposure to aqueous humor, thermoresponsive softening at body temperature, enzymatic degradation triggered by matrix metalloproteinases (e.g., MMP-2), or mechanical plunger actuation.

In addition to their role as delivery vehicles, hydrogel sleeves 204 provide mechanical benefits during the surgical procedure. They act as a protective layer between the conduit and the delicate canal wall, potentially reducing friction, minimizing trauma, and enhancing the safety of conduit advancement through Schlemm's canal 104. Furthermore, surgeons can customize sleeve length intraoperatively to treat specific regions of Schlemm's canal 104, offering precision in both mechanical intervention and biological therapy.

Collectively, the use of pre-formed hydrogel sleeves 204 represents a significant advancement in the field of regenerative canaloplasty. This approach integrates manufacturing precision with biological functionality, providing a scalable and practical solution for delivering endothelial cells 208 while maintaining safe conduit navigation and preserving Schlemm's canal 104 anatomy and function.

4.5 Hydrogel Endothelial Coating Applied to Conduits

In certain embodiments, a pre-formed hydrogel coating 602 is applied to the outer surface of a conduit (such as a catheter 202) during manufacturing. This hydrogel layer is engineered to serve as both a mechanical interface facilitating device navigation through Schlemm's canal 104 and a biological delivery platform capable of depositing endothelial cells 208 or therapeutic agents onto the canal wall.

Manufacturing techniques such as dip-coating, spray-coating, extrusion, or molding enable the formation of a uniform hydrogel layer around the conduit shaft. After application, the hydrogel is crosslinked and cured ex vivo to impart mechanical integrity, dimensional stability, and desired porosity or mesh size. Crosslinking may involve chemical reactions between reactive functional groups, photopolymerization using ultraviolet or visible light, or thermal curing methods, selected based on the hydrogel's chemical composition and intended performance.

The pre-formed hydrogel layer can be preloaded with therapeutic agents, including growth factors, anti-fibrotic compounds, or other bioactive molecules, and with viable endothelial cells 208. This dual-functional design transforms the conduit from a purely mechanical instrument into a biologically active delivery system capable of facilitating regenerative therapy.

Hydrogel coatings 602 are typically fabricated to be very thin, often ranging from approximately 5 to 15 micrometers in radial thickness. As a result, such a coating may increase the conduit's overall diameter by only about 10 to 30 micrometers, a dimension that ensures the coated device remains well below the inner diameter of commercially available introducer lumens, which range from approximately 250 to 300 micrometers. This dimensional compatibility enables hydrogel-coated conduits to be navigated safely within Schlemm's canal 104 and ensures compatibility with existing surgical instruments and techniques.

Hydrogel Coated Conduits for Canaloplasty

In certain embodiments, hydrogel coatings 602 are applied to conduits used for canaloplasty, either as pre-formed structures manufactured onto the conduit shaft or as in situ-formed hydrogels applied during surgery. The purpose of such hydrogel layers in canaloplasty includes reducing friction between the conduit and Schlemm's canal wall, enabling delivery of endothelial cells 208 or bioactive agents to promote canal healing and reduce fibrosis, and maintaining conduit flexibility and maneuverability within the narrow and curved canal lumen.

Figure 5:
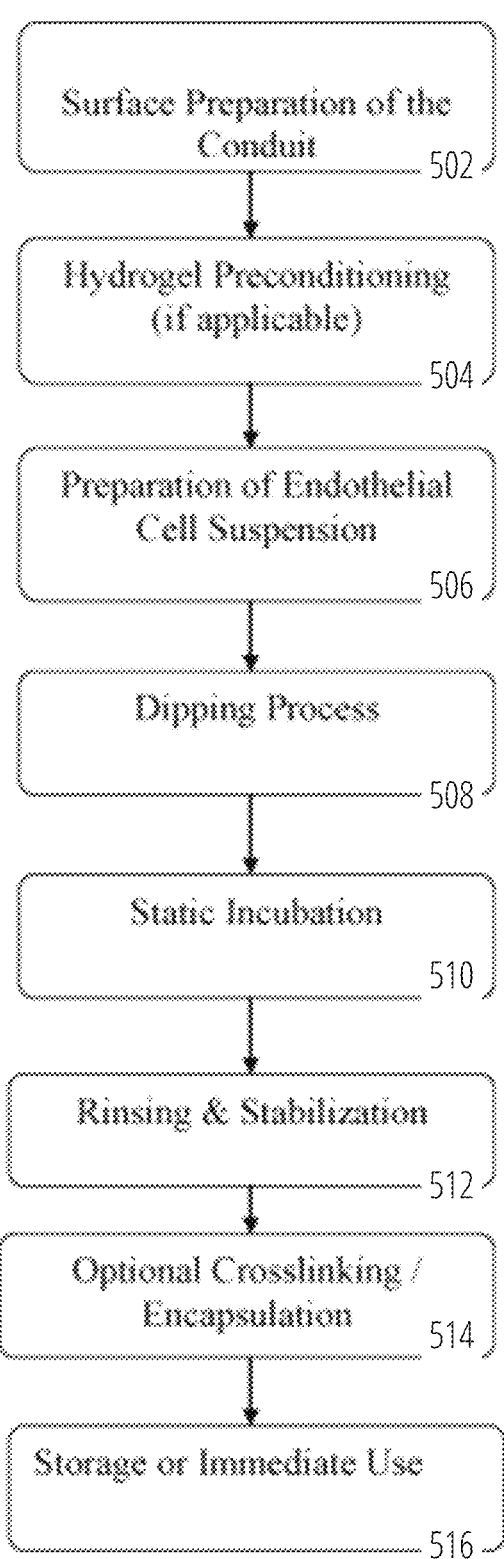
FIG. 5 is a flowchart outlining the standardized process for dip-coating a hydrogel-coated conduit with endothelial cells.

FIG. 5 is a flowchart outlining the standardized process for dip-coating a hydrogel-coated conduit with endothelial cells 208. This stepwise approach ensures optimal surface preparation, cell adhesion, viability, and storage for regenerative therapeutic applications in Schlemm's canal.

Dip-Coating a Conduit with Endothelial Cells

The process of dip-coating a conduit with endothelial cells 208 for therapeutic use in Schlemm's canal 104 begins with careful preparation of the conduit's surface 502. This initial step ensures that the surface is free from particulates and residues, achieved by cleaning with ethanol and sterile phosphate-buffered saline (PBS). Where appropriate, surface activation techniques such as plasma treatment or UV/ozone exposure are employed to enhance the adherence of subsequent coatings. If the conduit has not already been coated, a hydrogel layer is applied using either dip-coating or spray-coating techniques, followed by crosslinking to stabilize the coating. Following the hydrogel application, the surface may be preconditioned 504 to improve cellular adhesion. This involves soaking the hydrogel in a solution enriched with extracellular matrix (ECM) proteins, such as fibronectin or laminin, or in culture media to better mimic the natural environment for endothelial cells. Parallel to this, a suspension of endothelial cells must be prepared 506. These cells, either primary or immortalized (such as HUVECs), are cultured and expanded under sterile conditions. They are then suspended in a serum-rich medium at a concentration ranging from one to ten million cells per milliliter. Adhesion enhancers, like RGD peptides, may be added to increase the likelihood of successful attachment.

With both the conduit and the cell suspension ready, the actual dipping process 508 begins. The hydrogel-coated conduit is carefully held with sterile forceps and vertically dipped into the endothelial cell suspension. The duration of immersion typically ranges from thirty seconds to five minutes, and the withdrawal is performed slowly—at a rate of one to five millimeters per second—to ensure an even distribution of cells along the surface. To achieve higher densities, the dipping process can be repeated multiple times. Once coated, the conduit is placed horizontally or at an incline within a sterile incubation chamber 510. The environment is maintained at 37° C. with 5% carbon dioxide for a period ranging from thirty minutes to two hours, allowing the cells to properly attach to the hydrogel surface. After incubation, the conduit is gently rinsed 512 with sterile media or PBS to remove any non-adherent cells. If desired, a second hydrogel layer containing embedded cells can be applied, followed by additional crosslinking 514 to further secure the cells and improve resistance to mechanical shear. Finally, the coated conduit is either used immediately or stored under sterile, temperature-controlled conditions for short-term preservation 516. Prior to deployment, the viability and density of the attached endothelial cells 208 must be validated to ensure therapeutic efficacy. For clinical-grade products, compliance with good manufacturing practice (GMP) standards and quality control protocols is essential. The optimization of hydrogel selection, withdrawal rate during dipping, and coating thickness remains critical to achieving consistent and reproducible outcomes.

In some instances, the conduit may include a coating disposed only on the inner surfaces and/or outer surfaces of the conduit. While the coating may be disposed on both the outer and inner surfaces, the coating may be disposed on only one of the outer surface or the inner surface. Further, while the coating may extend over the entirety of the outer surface and the inner surface, in some embodiments, the coating may cover only a portion of the outer and/or inner surfaces. For example, the coating may cover 10% or more, 25% or more, or 75% or more of the surface area of the conduit. These are just examples. In some instances, the coating may cover less than 10% or more than 75% of the surface area of the conduit, as desired.

Endothelial Aggregation

Endothelial cell aggregation is an important factor to consider when determining the appropriate coating density for conduit-based delivery into Schlemm's canal 104/. At elevated densities, specifically in the range of one million cells per square centimeter ($10^6$ cells/cm$^2$) or more, several complications may arise that can diminish therapeutic efficacy and compromise safety.

One of the principal concerns with excessive cell density is the limitation of nutrient and oxygen diffusion. When endothelial cells form thick aggregates, the inner cells may become deprived of essential metabolic support, resulting in reduced viability or apoptosis. Additionally, endothelial cells are biologically optimized to function as a monolayer; when they are forced into multilayered clusters, their morphology, signaling, and behavior can deviate from normal physiological function. This loss of monolayer organization can impair the formation of a consistent and functional endothelial lining within Schlemm's canal 104.

Moreover, high-density coatings often lead to uneven cell distribution across the conduit surface. Clumping or patchy adherence can result in irregular regenerative patterns along the canal wall. These inconsistencies may also increase the risk of shear-induced detachment, especially during conduit insertion or fluid perfusion. Aggregated cells are less securely adhered and more prone to dislodgement under mechanical stress, which may compromise the targeted therapeutic outcome.

To mitigate these risks and ensure optimal coating performance, a cell density in the range of ten thousand to one hundred thousand cells per square centimeter ($10^4$-$10^5$ cells/ cm$^2$) is recommended. Within this range, endothelial cells are more likely to establish a uniform, viable monolayer, preserving their phenotype and functional characteristics. This density also minimizes the risk of aggregation, enhances cellular adherence, and improves survival rates after deployment into Schlemm's canal 104, thereby supporting a more predictable and sustained regenerative response.

TABLE 9

Endothelial Coating Density and Aggregation Risk

| Coating Density (cells/cm$^2$) | Expected Behavior | Aggregation Risk | Recommended Use |
|---|---|---|---|
| $10^3$ | Sparse coverage; incomplete monolayer | None | Insufficient for effective therapy |
| $10^4$ | Uniform monolayer; optimal function | Low | Ideal for most applications |
| $10^5$ | Dense monolayer; acceptable with monitoring | Moderate | Use with caution and validation |
| $10^6$ | High aggregation risk; viability concerns | High | Not recommended without optimization |

Table 9 outlines the impact of varying endothelial cell coating densities on catheter performance, cellular behavior, and therapeutic safety. Sparse coatings around $10^3$ cells/cm$^2$ result in insufficient coverage, while moderate densities between $10^4$ and $10^5$ cells/cm$^2$ provide optimal or acceptable monolayer formation with low to moderate aggregation risk. Densities approaching or exceeding $10^6$ cells/cm$^2$ pose a high risk of aggregation, reduced cell viability, and should only be considered with rigorous optimization.

Uniform Coating

Maintaining precise and uniform coating thickness is necessary, as it preserves consistent mechanical performance, navigability, and predictable behavior during delicate canaloplasty procedures. A uniform hydrogel layer minimizes the risk of canal obstruction, mechanical trauma, or unpredictable frictional resistance during device advancement. Moreover, pre-formed hydrogel coatings 602 provide significant advantages by allowing precise control over cell loading and the uniform distribution of therapeutic substances within the hydrogel matrix. This manufacturing precision enhances dosing accuracy and increases the likelihood of therapeutic efficacy and consistent biological outcomes.

Another benefit of pre-formed hydrogel coatings 602 is that they create a ready-to-use device, streamlining the surgical workflow. Surgeons can retrieve the hydrogel-coated conduit directly from sterile packaging and proceed with the intervention without the need for intraoperative hydrogel preparation or mixing procedures, thereby reducing operative time and procedural complexity. Pre-formed hydrogel coatings and hydrogel sleeves 204 also ensure manufacturing consistency by providing a uniform coating thickness and mechanical properties across production batches. This consistency is particularly crucial given the narrow and highly variable dimensions of Schlemm's canal 104, allowing surgeons to rely on predictable device behavior during delicate procedures.

Despite these advantages, pre-formed hydrogel coatings 602 present certain engineering and logistical challenges. Hydrogels are susceptible to dehydration during storage and handling. Loss of moisture can compromise the hydrogel's structural integrity, flexibility, or the viability of embedded endothelial cells 208. Therefore, specialized moisture-retaining packaging solutions, such as blister packs, foil pouches, or integrated humidification systems, are essential to maintain hydrogel functionality throughout its shelf life.

Additionally, pre-formed hydrogel layers can exhibit a degree of mechanical fragility, particularly when subjected to bending, twisting, or friction during handling, shipping, or surgical manipulation. This mechanical vulnerability highlights the importance of thoughtful product design and material selection to ensure that the hydrogel layer remains structurally intact and functional when introduced into Schlemm's canal 104. Furthermore, the need for moisture-retentive packaging and robust handling protocols adds manufacturing complexity and cost, underscoring the necessity of careful engineering and supply chain management.

of the canal treated, the estimated regenerated length, and the percentage of the canal receiving therapy. Shorter dipping lengths (e.g., 3 mm or 6 mm) are suitable for localized or focal defects, while longer segments (e.g., 24 mm to 36 mm) enable broader or full-canal regeneration for patients with diffuse disease or advanced glaucoma. Clinical considerations are provided to guide therapeutic planning based on the severity and distribution of Schlemm's canal pathology.

Projected Longevity of Schlemm's Canal Endothelial Cell Implants

The expected longevity of endothelial cells implanted into Schlemm's canal 104 is determined by a combination of biological viability, integration potential, and environmental

TABLE 10

Dimensional consideration for coatings and sleeves

| Parameter | Value (Typical) | Comment |
|---|---|---|
| Bare Catheter Diameter | 180-250 μm (commonly 200 μm) | Consistent across the cited patents. |
| Hydrogel Coating Thickness (per side) | 10-20 μm | To avoid exceeding introducer lumen diameters and ensure smooth catheter passage. |
| Total Diameter with Hydrogel Coating | 200 + (2 × 15) = 230 μm | Example based on a 15 μm coating per side. |
| Introducer Lumen Diameter | 250-400 μm | Limits total catheter diameter. |
| Typical Clearance in Introducer | 50-100 μm | Needed for device maneuvering and fluid movement. |
| Schlemm's Canal Lumen Diameter | 190-370 μm | Provides further boundary for safe catheter sizing. |

Table 10 provides dimensional specifications compiled from U.S. Pat. Nos. 12,042,428, 10,485,701, and 11,951,037, which serve to inform design parameters for hydrogel-coated and sleeved microcatheters in canaloplasty. These specifications help ensure that the combined diameter of the catheter and hydrogel layer remains suitable for introducer lumens, the anatomy of Schlemm's canal, and the fluid dynamics required for safe device operation and endothelial cell delivery.

Conduit Dipping Length and Regenerative Coverage factors. Native Schlemm's canal endothelial cells are known for their low turnover rate and can persist for many years under physiological conditions. Transplanted cells, whether autologous or allogeneic, must overcome additional challenges, including adhesion, flow stress, and immune tolerance.

The implanted cells may either survive long-term or trigger endogenous regeneration, both of which can restore the canal's function. Success depends on substrate compatibility, cellular response to flow dynamics, immunologic

TABLE 11

Relationship Between Conduit Dipping Length and Regenerative Coverage in Schlemm's Canal

| Dipped Catheter Length (mm) | Approximate Arc Treated (°) | Estimated Regenerated Canal Length (mm) | Regeneration Coverage (%) | Clinical Considerations |
|---|---|---|---|---|
| 3 mm | 30° | 3 MM | 8% | Localized treatment; for focal defects |
| 6 | 60 | 6 | 17 | Expanded treatment zone; small focal fibrosis |
| 12 | 120 | 12 | 33 | Partial quadrant; early glaucoma |
| 18 | 180 | 18 | 50 | Hemicanaloplasty equivalent |
| 24 | 240 | 24 | 67 | Broad coverage; useful for diffuse disease |
| 30 | 300 | 30 | 83 | Extensive coverage; near-total therapy |
| 36 | 360 | 36 | 100 | Full canal regeneration for pan-canal restoration |

Table 11 outlines the correlation between the length of a catheter segment coated with endothelial cells 208 and the corresponding regenerative coverage within Schlemm's canal 104. The dipped catheter length directly affects the arc conditions, and integration into the native matrix. In clinical applications, the ideal goal is to achieve sustained re-endothelialization that stabilizes intraocular pressure while minimizing the need for repeat intervention.

TABLE 12

| Factors Affecting Longevity of Implanted Endothelial Cells | | |
|---|---|---|
| Factor | Positive Impact | Negative Impact |
| Substrate adhesion | ECM-coated hydrogel or native wall | Poor adhesion, shear detachment |
| Perfusion and flow | Moderate shear stress promotes health | High turbulence may cause detachment |
| Cell type origin | Autologous preferred | Allogeneic risk of immune rejection |
| Immunologic response | Anti-rejection protocols, immune shielding | Local inflammation, cytokine exposure |
| Hydrogel support | Proper matrix facilitates integration | Over-swelling or degradation can be hostile |
| Ocular medication | Supportive therapies (e.g., anti-inflammatories) | Corticosteroids may suppress viability |

Table 12 outlines the projected lifespan of endothelial cells transplanted into Schlemm's canal 104 under optimized conditions, including ideal cell density, surface coverage, and catheter placement. It highlights the expected duration of therapeutic effect on intraocular pressure (IOP) and underscores the temporal limitations of cell viability in vivo. The data inform retreatment timelines and potential adjunctive strategies to extend clinical benefit.

Pre-formed hydrogel and hydrogel sleeves 204 represent a practical and progressive embodiment. They combine precise manufacturing with biological functionality, enabling safe navigation through Schlemm's canal 104 while delivering therapeutic endothelial cells and agents. With meticulous design, quality control, and handling practices, pre-formed hydrogel-coated conduits are configured to enhance the regenerative capacity of canaloplasty procedures, all while remaining compatible with current surgical techniques and anatomical constraints.

4.6 Endothelialization of Systemic Vasculature Versus Schlemm's Canal

Although various vascular prostheses have been developed to promote endothelialization in systemic circulation, these devices are designed primarily for high-pressure arterial and venous environments and exhibit structural, mechanical, and biologic properties tailored to thromboresistance and systemic vascular integration. The devices include microporous synthetic grafts with polymeric coatings and optional bioactive compounds for promoting endothelial cell adherence and minimizing platelet aggregation.

The systems and methods disclosed herein are directed specifically to Schlemm's canal 104, a low-pressure, microanatomic structure within the ocular anterior segment responsible for regulating aqueous humor outflow. Unlike systemic vasculature, Schlemm's canal 104 features a unique monolayer of specialized endothelial cells, which express distinctive pore-forming and shear-responsive behaviors critical to intraocular pressure (IOP) homeostasis.

Furthermore, the present disclosure emphasizes dual-layer endothelial integration—including mural and trabecular-facing surfaces—and supports segmental outflow modulation, optical imaging compatibility, and flow-responsive degradation. The coatings and polymers are selected not only for endothelial affinity but also for compatibility with optical coherence tomography (OCT), OCTA-based monitoring, and drug-eluting ECM remodeling. These design choices ensure that the hydrogel coating 602 or hydrogel sleeve 204 does not impede the conduit's ability to traverse the canal, minimizes the risk of canal trauma or obstruction, and enables reliable delivery of therapeutic agents or endothelial cells.

TABLE 13

| Schlemm's Canal Endothelial Conduits vs. Cardiovascular Endothelial Grafts | | |
|---|---|---|
| Feature | Schlemm's Canal Endothelial Conduits | Cardiovascular Endothelial Grafts |
| Anatomic Site | Schlemm's canal (ocular outflow tract) | Arteries and veins (systemic circulation) |
| Pressure Environment | Low-pressure (~10-21 mmHg) | High-pressure (50-120 mmHg in arteries) |
| Primary Function | Regulate aqueous humor drainage to control IOP | Restore blood flow and prevent thrombosis |
| Flow Regulation | Segmental, pressure-sensitive, often micropore-mediated | Continuous, high-volume laminar flow |
| Cell Type Targeted | Schlemm's canal endothelial cells (SCECs), mural cells | Vascular endothelial cells (e.g., aortic, venous) |
| Coating Purpose | Promote integration, shear-sensing, and outflow modulation | Reduce thrombosis and encourage re-endothelialization |
| Example Coatings | Fibronectin, laminin, collagen IV, nitric oxide-releasing gels | Heparin, polyethylene oxide, collagen |
| Drug-Eluting Purpose | ECM remodeling, nitric oxide release, fibrosis prevention | Anticoagulation (e.g., heparin), anti-proliferative drugs |
| Monitoring Modality | Optical Coherence Tomography (OCT/OCTA) compatibility | Angiography, ultrasound |
| Implant Size | Sub-millimeter to 3 mm curved microstents | Typically >4 mm diameter, 1-10 cm length |
| Degradation Profile (if bioabsorbable) | 1-6 months for pressure-dependent degradation | 6-18 months or longer for vascular remodeling |
| Immune Environment | Ocular immune privilege zone | Systemic immune surveillance |
| Clinical Risk Factors | Fibrosis, blockage of collector channels, scarring | Thrombosis, restenosis, inflammation |
| Reactivity to Implants | Requires ultra-low profile, non-reactive materials | Accepts thicker wall prostheses with flow-tolerant porosity |
| AI Diagnostic Integration | AI-assisted OCT/OCTA interpretation, risk prediction | Rare; generally not integrated |

5.0 COATINGS AND SLEEVES

TABLE 14

Practical Manufacturing Considerations for Hydrogel Coated and
Sleeved Microcatheters in Canaloplasty

| Feature | Coating | Sleeve |
|---|---|---|
| Thickness Control | Excellent (dip or spray) | More variable, mold-dependent |
| Cell Loading Capacity | Lower | Higher |
| Mechanical Robustness | More delicate | Potentially sturdier |
| Hydration Needs | Must remain hydrated | Also moisture-sensitive but often thicker and sturdier |
| Manufacturing Complexity | Moderate-High | High |
| Customizability | Less flexible | Highly customizable |
| Surgeon Workflow Impact | Minimal | Adds intraoperative steps |
| Regulatory Path | Simpler (single device) | More complex (two parts) |

Table 14 summarizes key manufacturing and engineering parameters relevant to creating hydrogel coatings 602 and hydrogel sleeves 204 for microcatheters intended for use in Schlemm's canal 104. It presents dimensional tolerances, hydrogel thickness constraints, swelling allowances, endothelial cell loading ranges, and minimum effective device lengths required for clinical efficacy. The information reflects practical limits imposed by existing introducer lumen diameters, anatomical canal dimensions, and mechanical handling during surgical procedures. These considerations collectively support enablement and feasibility for both hydrogel-coated and hydrogel-sleeved catheter embodiments in regenerative canaloplasty applications.

5.1 Comparisons for Hydrogel Sleeves and Coatings for Canaloplasty Devices

Several U.S. patents, including U.S. Pat. Nos. 12,042,428, 10,485,701, and 11,951,037, describe introducer-compatible conduits for canaloplasty with outer diameters ranging from approximately 180 μm to 250 μm. Introducer lumens vary between 250 μm and 400 μm, leaving a typical clearance of 50-100 μm. These tolerances guide design constraints for hydrogel coatings 602 and hydrogel sleeves 204 intended to deliver endothelial cells 208 or therapeutic agents.

Hydrogel coatings 602 should be limited to 10-20 μm per side to avoid significant encroachment, leading to a coated conduit diameter of 220-240 μm. This remains compatible with most introducers and with Schlemm's canal 104 dimensions, which typically range from 190-370 μm in vertical height and 30-75 μm in width. As swelling may occur post-implantation, hydrogel chemistry should be optimized to ensure dimensional stability.

Hydrogel sleeves 204, encasing the conduit, require more volume and must be carefully designed to avoid exceeding introducer tolerances or anatomical limits. Both coatings and sleeves fall within the scope of this document, provided that their combined diameter and swelling behavior remain within safe surgical and anatomical parameters.

Figure 6:
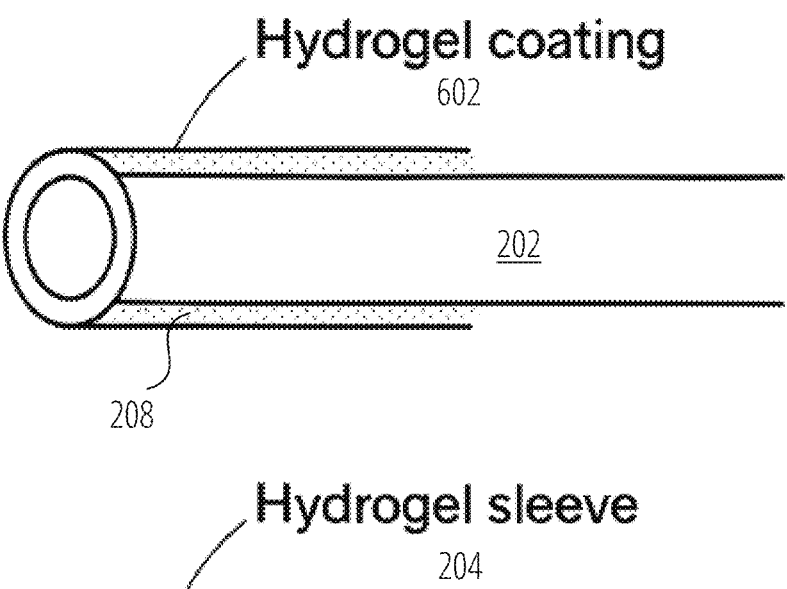
FIG. 6 shows a comparative cross-sectional view of hydrogel sleeve vs. hydrogel coating on a canaloplasty catheter

FIG. 6 shows a comparative cross-sectional view of a hydrogel sleeve 204 vs. A hydrogel coating 602 on a canaloplasty catheter. This schematic illustrates the dimensional and structural differences between two embodiments of regenerative hydrogel application: (1) a hydrogel sleeve 204 loosely encasing the catheter, and (2) a thin hydrogel coating 602 conformally bonded to the catheter 202 surface. The hydrogel sleeve 204 configuration adds greater thickness and may present anatomical fit challenges within Schlemm's canal 104, particularly in narrow or fibrotic regions. In contrast, the coated configuration maintains a low profile and preserves canal clearance, making it more suitable for widespread clinical application. The detailed narrative that follows addresses the anatomical implications, deployment considerations, and disclaimers relevant to each embodiment.

Dimensional and Anatomical Considerations: Hydrogel Coatings Vs. Sleeves

Standard microcatheters used in canaloplasty procedures typically have an outer diameter (OD) of approximately 250 microns (m). When a hydrogel coating 602 is applied directly to the catheter 202 surface, it can be engineered as a thin conformal layer, typically 5 to 15 μm per side, resulting in a total device diameter of 260-280 μm. This low-profile modification preserves the catheter's maneuverability and compatibility with Schlemm's canal 104 without significantly increasing its cross-sectional footprint. In many applications, hydrogel coatings 602 provide a safer dimensional profile than hydrogel sleeves 204, particularly when regenerative therapies are deployed in narrow or fibrotic canals.

In contrast, a hydrogel sleeve 204, which loosely envelops the catheter 202 in a tubular structure, contributes substantially more thickness. Even under conservative assumptions, a hydrogel sleeve 204 may add 25 to 50 μm per side, producing a total diameter of 300-350 μm. This enlarged profile may interfere with navigation and deployment in certain anatomies and increases the risk of frictional trauma or mispositioning, especially in compromised or stenotic Schlemm's canals 104.

These dimensional differences are clinically significant when compared to the native anatomy of Schlemm's canal 104. In its natural, undistended state, the canal typically exhibits a flattened elliptical shape with lumen heights of 190-350 μm and widths of 30-75 μm. While surgical viscodilation can temporarily expand the canal diameter to 400-500 μm, this effect is inconsistent and may not be sustained along the canal's entire circumference.

Accordingly, hydrogel coatings 602 offer superior anatomical compatibility and reduced risk, especially in systems where the catheter's diameter is already near the upper threshold of the canal. Coatings also reduce concerns related to hydrogel swelling, deployment friction, and intraluminal occlusion, making them a preferred regenerative approach in many clinical scenarios.

It must be emphasized, however, that the safe and effective use of hydrogel-based regenerative therapy depends on the specific canaloplasty system and patient anatomy. Practitioners and developers are encouraged to perform due diligence and evaluate whether their chosen approach, whether coating or sleeve, is appropriately matched to the anatomical and procedural environment. This serves as a fair and prudent warning to support safety, efficacy, and regulatory compliance in all implementations of this technology.

5.2. In Situ-Forming Hydrogel Coating

In other embodiments, the hydrogel coating 602 may form in situ during the surgical procedure, wherein liquid hydrogel precursors are applied to the conduit surface and undergo polymerization or gelation within Schlemm's canal 104. This approach allows for a conformable and patient-specific coating that adapts to anatomical variations.

In this embodiment, the hydrogel layer is designed to form in situ on the surface of the conduit during the surgical procedure itself. Unlike pre-formed hydrogel coatings 602 applied ex vivo, in situ-forming hydrogels provide a dynamic and adaptable approach, allowing the hydrogel to conform precisely to Schlemm's canal 104 anatomy and surgical conditions encountered intraoperatively.

Various in situ-forming mechanisms are contemplated, including injectable precursors, wherein two liquid components are mixed immediately prior to or during injection into Schlemm's canal 104. Upon contact or mixing within the canal, these precursors undergo chemical crosslinking or physical gelation, forming a hydrogel layer that encapsulates the conduit shaft. Photocurable hydrogels, in which a liquid hydrogel precursor is first applied to the conduit surface. Following conduit placement within Schlemm's canal 104, the hydrogel is polymerized and solidified using an external energy source, such as ultraviolet (UV) light, thereby forming a conformal coating around the conduit. Thermo-responsive hydrogels, which remain in a liquid state at lower temperatures (e.g., room temperature) and rapidly transition into a gel upon exposure to physiological temperatures within the eye 102. This transition ensures that the hydrogel solidifies only after the conduit has been correctly positioned in Schlemm's canal 104.

5.3 Hydrogel Embodiments for Conduit Coatings

In one embodiment, endothelial cells 208 are delivered into Schlemm's canal 104 via a microcatheter advanced circumferentially through the canal lumen. This approach leverages the precision and safety profile of established microcatheter-based procedures while introducing the novel benefit of biological cell therapy aimed at regenerating the endothelium of Schlemm's canal 104.

Hydrogel configurations may be prepared in either pre-formed or in situ formats. With a pre-formed hydrogel, the bare conduit diameter is 200 μm, the hydrogel adds 15 μm per side, resulting in a total diameter of 230 μm. The coating thickness is directly measurable and controlled during manufacturing.

With in situ hydrogel, the conduit remains approximately 200 μm in diameter, and the hydrogel fills gaps between the conduit surface and the canal wall. This may not significantly alter the conduit's effective diameter.

In certain embodiments, the hydrogel coating 602 is pre-formed and applied ex vivo, yielding a ready-to-use device with a uniform coating thickness and the potential for preloaded endothelial cells 208 or therapeutic agents.

5.4 In Situ-Forming Hydrogel

In situ-forming hydrogel systems offer distinct and significant advantages in the context of endothelial cell delivery to Schlemm's canal 104. One primary benefit lies in their inherent ability to conform intimately to the complex, three-dimensional architecture of the canal. This conformability ensures that the hydrogel molds precisely against the canal walls, thereby minimizing gaps or spaces that might otherwise interfere with effective cell transfer or engraftment.

Additionally, the in situ-forming hydrogel technique requires minimal pre-procedural preparation because the hydrogel matrix is created only during the surgical procedure itself. This characteristic can simplify logistical concerns and reduce storage demands, making it a practical option for surgical environments.

Another important advantage is the hydrogel's adaptability during surgery, allowing the surgeon to tailor the formulation in real time to address patient-specific anatomical features, such as variations in canal diameter, curvature, or localized regions of fibrosis. This flexibility enables a highly personalized approach to regenerative therapy, enhancing both safety and efficacy.

5.5 In Situ-Forming Hydrogels

Despite these benefits, the use of in situ-forming hydrogels presents several technical and procedural challenges that must be carefully addressed to ensure successful outcomes. The technique requires a high degree of surgical precision and impeccable timing, as the gelation or polymerization process must be meticulously controlled to prevent premature solidification or unintended hydrogel placement.

Furthermore, the kinetics of the polymerization or gelation reactions must be sufficiently rapid to align with the practical constraints of surgery, thereby avoiding intraoperative delays that could prolong the procedure and increase the risk of complications.

It is also essential to consider the chemical and physical properties of the hydrogel formulation itself; certain chemistries used to initiate gelation may produce heat or release reactive byproducts during polymerization. Such effects could pose risks to the delicate endothelial cells or surrounding ocular tissues if not rigorously controlled. Consequently, the design and selection of in situ-forming hydrogels demand a careful balance between achieving rapid, reliable gelation and maintaining a biocompatible environment conducive to cellular viability and tissue regeneration.

5.6 Illustrative Example of In Situ-Forming Hydrogels

By way of example, a surgeon may inject a liquid hyaluronic acid (HA)-based hydrogel precursor into Schlemm's canal 104 while the conduit is in place. The precursor material subsequently undergoes rapid gelation, forming a thin, conformal hydrogel layer that encapsulates the conduit shaft. This hydrogel layer can then serve both as a lubricious interface, reducing friction during conduit manipulation, and as a carrier matrix for endothelial cells, enabling direct cell transfer to the canal wall as the conduit is advanced or withdrawn.

5.7 Hydrogel Sleeve Embodiment

Among the embodiments disclosed here is the hydrogel sleeve 204 configuration, designed to enhance both mechanical safety and biological efficacy during Schlemm's canal 104 intervention. This embodiment consists of a pre-formed cylindrical sleeve of hydrogel material, concentrically fitted around a microcatheter shaft. The inner diameter of the sleeve is engineered to maintain a snug, stable fit along the conduit, while the outer diameter is optimized for safe passage through Schlemm's canal 104, minimizing trauma to the delicate endothelium.

Upon deployment, the hydrogel sleeve 204 enables uniform circumferential delivery of therapeutic agents, particularly endothelial cells 208, directly along the canal's inner wall. Several deployment strategies may be employed to activate or release the sleeve from the conduit. These include friction-based retention, whereby the hydrogel sleeve 204 is gently dislodged during conduit withdrawal; swelling behavior triggered by contact with aqueous humor; thermoresponsive softening upon reaching physiological body temperature; enzymatic degradation mediated by local protease activity; or the use of a mechanical plunger to advance the sleeve into position.

This design offers multiple benefits: it provides mechanical protection to Schlemm's canal 104 during insertion, facilitates precise and circumferential cell delivery, and ensures a controlled and localized release of the hydrogel's contents once deployed. In a representative example, the sleeve is constructed from polyethylene glycol diacrylate (PEGDA) and is pre-loaded with endothelial cells 208 at a concentration of approximately $1 \times 10^6$ cells/mL. The formulation is engineered to degrade gradually over 5 to 10 minutes in vivo, allowing for time-controlled diffusion of cells and bioactive factors into the surrounding tissue.

By combining structural protection, targeted delivery, and biological integration, the hydrogel sleeve 204 represents a highly versatile and effective embodiment within the broader platform of regenerative Schlemm's canal therapies.

6.0 DESIGN AND ENGINEERING OF COATINGS AND SLEEVES

The document contemplates multiple design features to ensure compatibility and safe use of hydrogel coatings 602 or hydrogel sleeves 204 that are implanted in surgery involving Schlemm's canal 104, including the precise control of hydrogel wall thickness during manufacturing to ensure total conduit diameter remains below canal lumen diameters (typically 190 μm to 370 μm) and introducer lumen diameters (typically 250 μm to 300 μm). The use of low-swelling hydrogel formulations, such as crosslinked PEG or modified hyaluronic acid, to limit dimensional changes during surgery, is also considered, as is the design of the sleeve's internal surface (e.g., microtexturing) to enhance gripping on the conduit shaft and prevent migration during manipulation. Mechanical resilience of the hydrogel matrix to withstand bending forces encountered during 360-degree canal catheterization is also considered.

Thus, based on commercially available conduit and introducer dimensions, and with appropriate engineering of hydrogel properties, the use of hydrogel coatings 602 or hydrogel sleeves 204 for delivering endothelial cells 208 in Schlemm's canal 104 is fully enabled. The disclosed embodiments provide a practical path for integration into existing surgical workflows without significant risk of device incompatibility or procedural complications.

6.1 Surgical Advantages Provided by Hydrogel Coatings and Sleeves

A pre-formed hydrogel embodiment, implemented either as a hydrogel coating 602 or as a hydrogel sleeve 204 on a microcatheter and delivered sterile, can incorporate a polyethylene glycol (PEG) hydrogel layer that is already crosslinked and loaded with endothelial cells. This configuration provides a low-friction surface that enhances navigation through Schlemm's canal 104 and serves as a biological delivery vehicle, depositing endothelial cells 208 along the canal wall to support regenerative healing. Obstructive elements in Schlemm's canal 104, including scar tissue, septae, and regions of constriction, may be traversed more smoothly due to the reduced frictional surface of the hydrogel-coated or sleeved conduit. This section introduces key mechanical and lubricity considerations relevant to the friction-reduction calculations, selection of conduit base materials, and comparative analysis of hydrogel and alternative coating materials.

6.2 Methodology and Calculations for Friction Reduction

In certain embodiments, a hydrogel coating 602 or hydrogel sleeve 204 reduces frictional forces between the microcatheter and the wall of Schlemm's canal 104. The magnitude of this friction reduction depends on both the physical properties of the hydrogel and the inherent frictional characteristics of the conduit's base material.

Different conduit materials exhibit distinct coefficients of friction (hereinafter referred to as "μ_bare"), such as:

Polyimide: approximately 0.35

PTFE (polytetrafluoroethylene): approximately 0.10

PEEK (polyether ether ketone): approximately 0.20

Silicone: approximately 0.25

When a hydrogel coating is applied, the coefficient of friction at the hydrogel-tissue interface generally ranges from approximately 0.05 to 0.10.

For example, a polyimide conduit may experience a reduction in friction of approximately 74 percent. Let $\mu_{bare}$ represent the coefficient of friction of the uncoated conduit, and $\mu_{coated}$ represent the coefficient of friction after the hydrogel coating 602 is applied. The percent reduction in friction is calculated according to the following formula:

$$\text{Percentage Reduction} = \frac{\mu_{bare} - \mu_{coated}}{\mu_{bare}} \times 100$$

Applying this equation to a polyimide conduit:

$$\text{Percentage Reduction} = \frac{0.35 - 0.09}{0.35} \times 100 \approx 74\%$$

Conversely, a PTFE conduit, which already possesses a relatively low coefficient of friction, may achieve only a modest reduction of approximately 10 percent. Nonetheless, hydrogel coatings 602 provide additional biological benefits, including facilitating endothelial cell delivery and offering a protective interface that reduces mechanical trauma to the canal wall.

A reduction of 74 percent means that the frictional resistance experienced during conduit navigation is significantly lowered, improving maneuverability through Schlemm's canal 104 and minimizing the risk of mechanical injury to the delicate canal structures.

Accordingly, the hydrogel-coated embodiments disclosed herein are compatible with various conduit materials and designs used in existing and future canaloplasty devices, offering both mechanical lubricity and biological regenerative advantages.

6.3 Calculation of Frictional Force for Conduit Navigation

During conduit-based interventions in Schlemm's canal 104, resistance to conduit advancement is determined by frictional forces between the conduit surface and the canal wall. The frictional force:

$$F_{friction} = \mu \times N$$

where:

$F_{friction}$ is the frictional force during motion (Newtons, N).

$\mu$ is the coefficient of friction between the conduit surface and the endothelial lining of Schlemm's canal 104.

N is the normal force pressing the conduit against the canal wall (Newtons, N).

This formula details the variables affecting friction forces. It focuses on how normal force and coefficient of friction together determine resistance during conduit motion.

The coefficient of friction depends on the conduit base material (e.g., polyimide, PTFE, silicone), the presence and type of surface coatings (hydrophilic or hydrogel coatings), and the degree of hydration and lubrication during surgery.

Bare conduit materials typically exhibit higher friction, while hydrogel coatings reduce substantially, creating a lubricious surface that facilitates safer and smoother device navigation.

6.4 Effect of Hydrogel Coating

Uncoated microcatheters commonly exhibit coefficients of friction in the range of approximately:

$\mu_{bare} \approx 0.25$ to $0.35$

When a hydrogel coating 602 is applied, the coefficient of friction can be substantially reduced, often falling within the range of:

$\mu_{coated} \approx 0.05$ to $0.10$

This represents a significant reduction, potentially exceeding 70% compared to bare conduits.

6.5 Diameter Calculations for Coatings and Sleeves

Another critical design parameter is the diameter of a conduit such as a conduit, both in its bare state and with any hydrogel coating 602 applied. The average diameter of Schlemm's canal 104 lumen ranges from approximately 190 micrometers (μm) to 370 μm. To prevent mechanical obstruction or trauma, the outer diameter of a hydrogel-coated conduit should remain below the canal's lumen diameter.

Let:

$D_{bare}$=bare conduit diameter.

$t_{hydrogel}$=hydrogel coating thickness.

Then the total coated microcatheter diameter (hereinafter referred to as "$D_{coated}$") is calculated as:

$$D_{coated} = D_{bare} + 2 \times t \text{ hydrogel}$$

For example, if

Bare conduit diameter=$D_{bare}$=200 μm.

Hydrogel coating thickness=$t_{hydrogel}$=15 μm

Then the total coated diameter is calculated as:

$$D_{coated} = 200 \text{ μm} \pm (2 \times 15 \text{ μm}) = 230 \text{ μm}$$

This calculated diameter remains within the typical anatomical range of Schlemm's canal 104 and would be suitable for safe device navigation. Thus, both the coefficient of friction and the conduit's total diameter must be precisely engineered to ensure effective and safe conduit passage during canaloplasty procedures.

6.6 Impact of Hydrogel Coatings on Friction and Conduit Navigation

When a hydrogel layer is applied, the outer frictional interface shifts from the base conduit material to the hydrogel-tissue interface, and hydrogel-coated conduits typically demonstrate coefficients of friction in the range of approximately 0.05 to 0.10.

This represents a potential reduction in frictional resistance of up to 70 to 80 percent compared to certain bare conduit materials.

6.7 Lubricity and Friction Metrics

The hydrogel sleeve 204 or hydrogel coating 602 is purposefully engineered to enhance compatibility with existing canaloplasty devices, including microcatheters commonly used for viscodilation and trabeculotomy. Rather than impeding function, the hydrogel layer actively improves device performance by serving as a lubricious interface between the conduit and the inner wall of Schlemm's canal 104. This lubricity facilitates smoother passage of the device, minimizing mechanical trauma and enhancing procedural safety.

Hydrogels are ideal for this purpose due to their intrinsic properties. Their high water content creates a hydrated boundary layer that reduces interfacial shear forces and mechanical resistance. Many hydrogels, such as polyethylene glycol (PEG) derivatives and hyaluronic acid, are already well established as medical lubricants. These materials are widely used in ophthalmic viscoelastic devices, intraocular lens coatings, cardiovascular conduits, and urinary conduits precisely because of their low-friction behavior and biocompatibility.

Importantly, hydrogel coatings 602 can be engineered to remain extremely thin, typically in the range of 10-30 microns. This thin profile ensures that the hydrogel does not substantially increase the outer diameter of the conduit, preserving compatibility with the confined space of Schlemm's canal 104 and avoiding any risk of canal obstruction or interference with viscoelastic flow. Additionally, swelling of the hydrogel can be modulated to occur only after deployment, and selective segmental application allows hydrogel placement to avoid interfering with injection ports or imaging windows.

One of the most quantifiable benefits of hydrogel application is its dramatic reduction of frictional force. Frictional resistance encountered during conduit advancement or withdrawal is governed by the relationship:

$$F_{friction} = \mu \times N$$

where: $F_{friction}$ is the frictional force (in Newtons), $\mu \times$ is the coefficient of friction between the conduit and the canal wall (dimensionless), and N is the normal force exerted by the conduit on the canal wall (in Newtons).

Uncoated microcatheters typically exhibit coefficients of friction in the range of $\mu_{bare} \approx 0.25$ to $0.35$. By contrast, hydrogel-coated conduits can achieve $\mu_{coated} \approx 0.05$ to $0.10$. For instance, if an uncoated conduit demonstrates $\mu_{bare} \approx 0.30$ and the coated version exhibits $\mu_{coated} \approx 0.09$, the resultant frictional force is reduced by approximately 70% under equivalent normal loads. This significant reduction minimizes the risk of endothelial abrasion or shear injury and enables more delicate navigation within Schlemm's canal 104.

Thus, the hydrogel component not only enables biological delivery of endothelial cells 208 but also provides a mechanical advantage. It ensures safe, low-resistance transit of microcatheters through delicate intraocular structures, an essential consideration in minimally invasive glaucoma surgeries. These characteristics demonstrate that hydrogel sleeves 204 and hydrogel coatings 602 do not interfere with canaloplasty functionality. Rather, they enhance it by improving safety, control, and regenerative potential, solidifying the hydrogel's dual role as both a therapeutic delivery vehicle and a surgical performance enhancer.

Illustrative Example Calculation

Consider a scenario where the normal force exerted between the conduit and the canal wall is: N=0.15 N For a bare conduit: $F_{friction,\ bare} = \mu\ bare \times N = 0.30 \times 0.15 = 0.045$ N For a hydrogel-coated conduit: $F_{friction,\ coated} = \mu_{coated} \times N = 0.09 \times 0.15 = 0.0135$ N The difference in frictional force is: $\Delta F = F_{friction,\ bare} - F_{friction,\ coated} = 0.045 - 0.0135 = 0.0315$ N This yields a percent reduction in frictional force of:

$$\text{Percent Reduction} = (\Delta F / F_{friction,\ bare}) \times 100\% = (0.0315/0.045) \times 100\% \approx 70\%$$

Thus, the hydrogel coating 602 can reduce conduit friction against Schlemm's canal wall by approximately 70% under equivalent normal forces. This significant benefit facilitates safer, less traumatic device insertion and enhances the surgical precision and comfort of intraocular canal-based procedures.

Thus, the hydrogel component not only enables biological delivery of endothelial cells 208 but also provides a mechanical advantage. It ensures safe, low-resistance transit of microcatheters through delicate intraocular structures—an essential consideration in minimally invasive glaucoma surgeries. These characteristics demonstrate that hydrogel sleeves and coatings do not interfere with canaloplasty functionality. Rather, they enhance it by improving safety, control, and regenerative potential, solidifying the hydrogel's dual role as both a therapeutic delivery vehicle and a surgical performance enhancer.

Clinical Significance

The reduction in conduit friction achieved through hydrogel coatings 602 holds profound implications for both surgical efficacy and ocular tissue preservation. Clinically, decreased resistance during conduit navigation enhances the surgeon's ability to maneuver within Schlemm's canal 104 with greater precision and reduced force, which is especially critical in narrow or tortuous canal segments. This lubricity translates into smoother advancement, less tactile feedback interference, and a diminished likelihood of abrupt microcatheter jumps or binding.

Lowering the coefficient of friction minimizes shear forces exerted upon the canal's endothelial lining. Schlemm's canal 104 endothelium is a delicate, functionally specialized tissue involved in aqueous humor outflow regulation. Excessive mechanical trauma during device passage risks disrupting this vital layer, potentially impairing physiological outflow or inciting local inflammation. By mitigating this risk, hydrogel-coated conduits not only preserve native tissue integrity but also create a more hospitable environment for regenerative therapies, including the delivery of therapeutic endothelial cells 208.

In this dual role, hydrogel-coated embodiments do not merely transport regenerative agents, they actively contribute to a safer, more refined surgical platform. Compared to uncoated devices, these constructs offer an elegant combination of mechanical enhancement and biological compatibility, supporting a paradigm shift toward minimally invasive, precision-guided glaucoma interventions. These innovations align with modern surgical objectives of reducing collateral tissue injury, shortening recovery times, and optimizing long-term outcomes in canaloplasty and related procedures.

SUMMARY

Reducing friction provides critical clinical benefits, including smoother conduit passage through Schlemm's canal, minimized endothelial trauma during threading or viscodilation, enhanced control and precision for the surgeon, and lower risk of iatrogenic damage to the canal's delicate inner wall.

TABLE 15

Dimensional Comparisons for Coatings and Sleeves

| Feature | Bare Conduit | Hydrogel Sleeve (Thin Wall) | Hydrogel Sleeve (Thicker Wall) | Introducer Lumen | Comments |
|---|---|---|---|---|---|
| Conduit Diameter (µm) | 200 µm | 220-230 µm | 240-260 µm | 250-300 µm | Sleeve must stay well below lumen ID to ensure smooth passage. |
| Sleeve Wall Thickness (per side) | | 10-15 µm | 20-30 µm | | Thin walls preferred for clearance. |
| Total Diameter Increase | | +20-30 µm | +40-60 µm | | Thicker sleeves risk friction or blockage. |
| Annular Clearance in Lumen | | 10-40 µm | Possibly ≤10 µm or none | 10-50 µm desired | Lower clearance raises risk of tight fit or blockage. |
| Hydrogel Swelling | | <10-15% volumetric | 20-30% volumetric | | Low-swelling chemistries critical for safety. |
| Typical Sleeve Length | | 5-20 mm | 5-20 mm | | Customizable for surgical anatomy. |
| Mechanical Robustness | Good | Good if thin & cross-linked | Risk of buckling | | Thin sleeves preferred to avoid mechanical failures. |
| Cell Payload | N/A | Moderate | Higher capacity | | Thicker sleeves may carry more cells but risk tight fits. |

Table 15 summarizes dimensional parameters relevant to hydrogel coating 602 and hydrogel sleeves 204 applied to canaloplasty microcatheters. It provides typical bare catheter diameters, hydrogel layer thicknesses, and resulting outer diameters for coated or sleeved configurations. These dimensions are engineered to ensure safe passage through introducer lumens and Schlemm's canal 104, while accommodating hydrogel swelling limits and preserving sufficient clearance for viscoelastic flow and device maneuverability. The data presented support the enablement of both hydrogel coatings 602 and hydrogel sleeves 204 as viable embodiments for delivering endothelial cells 208 or therapeutic agents during canaloplasty.

TABLE 16

Design Parameters for Hydrogel Application

| Parameter | Typical Value | Details and Rationale |
|---|---|---|
| Hydrogel Coating Thickness (per side) | 10-20 µm | Sufficient for lubricity, cell loading, and minimal diameter increase. Enables significant |

TABLE 16-continued

| Design Parameters for Hydrogel Application | | |
|---|---|---|
| Parameter | Typical Value | Details and Rationale |
| | | friction reduction (up to ~70-80%). |
| Total Diameter Increase from Coating | ≤40 μm | Keeps catheter safely within Schlemm's canal diameter limits (typically 190-370 μm). |
| Recommended Coated/Sleeved Length (Full Canaloplasty) | 35-40 mm | Matches approximate Schlemm's canal circumference (35-37 mm) to enable uniform treatment and cell delivery. |
| Recommended Coated/Sleeved Length (Segmental Treatment) | 9-18 mm | Suitable for partial canaloplasty procedures (quarter or half canal). Reduces hydrogel volume for targeted therapy. |
| Endothelial Cell Density in Hydrogel | ~2,000-5,000 cells/mm² | Enables effective cell seeding onto canal walls during short surgical exposure. |
| Working Length of Catheter Shaft | ~100-150 mm | Commercially typical catheter length. Accommodates various coating or sleeve segment lengths. |

Table 16 summarizes the recommended engineering specifications for hydrogel coatings 602 and hydrogel sleeves 204 used in microcatheter-based canaloplasty procedures. Each parameter is tailored to optimize lubricity, endothelial cell delivery, and mechanical compatibility with Schlemm's canal 104. Considerations include coating thickness for friction reduction, preservation of canal patency through minimal diameter increases, segmental and circumferential treatment lengths, and safe therapeutic cell densities, all within the dimensional constraints of intraocular microdevices. These design values reflect translational feasibility and support both biological and procedural goals.

6.8 Hydrogel Coating Thickness.

Experimental and clinical data indicate that a hydrogel coating 602 of approximately 10 to 20 micrometers (m) per side is sufficient to produce substantial lubricity gains, lowering the coefficient of friction at the hydrogel-tissue interface to approximately 0.05 to 0.10. Even thin hydrogel layers can carry high densities of endothelial cells 208, typically in the range of 2,000 to 5,000 cells per square millimeter, sufficient for regenerative therapy during short surgical exposure times.

6.9 Design Tolerance

The combined diameter of the conduit plus hydrogel layer must remain below the average Schlemm's canal 104 diameter of approximately 190 to 370 μm. A 200 μm bare conduit with a 15 μm hydrogel layer on each side yields a total diameter of 230 μm, safely within anatomical tolerances.

6.10 Conduit Length for Coatings

For circumferential canaloplasty, a hydrogel-coated segment length of approximately 35 to 40 millimeters is optimal to match the full circumference of Schlemm's canal 104. Shorter segments, ranging from 9 to 18 millimeters, may be used for segmental treatments or focal pathology. Conduits typically have a working length of 100 to 150 millimeters, accommodating these coated segments without interfering with conduit handling or introducer passage.

TABLE 17

| Correlation Between Hydrogel Implant Length and Schlemm's Canal Regeneration | | | |
|---|---|---|---|
| Hydrogel Length (mm) | Canal Angle Covered (°) | With Pre-Seeded Endothelial Cells | With Native Cell Migration (10-14 days) |
| 2 mm | 20° | Immediate coverage and remodeling of ~20° | Likely complete within 10 days |
| 5 | 50 | Rapid regenerative alignment, ~50° | Complete coverage in 10-14 days |
| 10 | 100 | Immediate endothelial support across full span | May require 2-3 weeks for complete migration |
| 18 | 180 | Feasible with expanded pre-seeding or multicentric loading | Possible with staged or zone-wide migration over 3-4 weeks |
| 36 | 360 | Requires extensive cell expansion and controlled distribution | Unlikely without multiple implants or advanced cell-guiding strategies |

Table 17 correlates the angular coverage of Schlemm's canal 104 regeneration with the physical length of the hydrogel implant. It distinguishes between scenarios with pre-seeded endothelial cells 208 and those relying on cell-free, bioactive hydrogel guidance of native Schlemm's canal endothelial cells (SCECs). The analysis assumes an average human Schlemm's canal 104 circumference of approximately 360 degrees or about 36 mm in arc length, and SCEC migration rates of about 100 μm/day.

Considerations for Variable Conduit Lengths

This document anticipates that conduits that include microcatheters may be used for partial (e.g., 180°) or full (360°) canalization. Thus, manufacturers may produce hydrogel sleeves 204 in standardized lengths to fit different surgical plans; surgeon-prepared sleeves allow real-time customization, enabling precise tailoring to the anatomy and surgical objectives of each patient; and in some embodiments, the hydrogel sleeve 204 is configured as a scored hydrogel that is technically also described as frangible hydrogel. In this configuration, the hydrogel sleeve 204 has one or more linear or circumferential grooves that are pre-engineered into the body of the hydrogel to facilitate controlled mechanical separation upon retraction, resistance, or targeted manipulation. These scored regions define frangible zones that reduce the force required to separate hydrogel segments, ensuring atraumatic disengagement when anatomical limitations prevent full deployment.

6.11 Biodegradable Polymers as Alternatives to Hydrogel

This document further contemplates that materials other than hydrogels may be utilized in the construction of sleeves or coatings intended for delivering endothelial cells 208 into Schlemm's canal 104. Although hydrogels offer substantial advantages for cell delivery due to their hydrophilic nature, biocompatibility, and capacity for controlled degradation, they are not without limitations. Such limitations include potential swelling within the confined space of Schlemm's canal 104, mechanical fragility under surgical manipulation, and challenges associated with maintaining viable cells during storage and handling. Accordingly, this document envisions alternative substrates that may overcome these limitations and provide additional functional benefits.

In certain embodiments, the sleeve or coating may comprise biodegradable polymers such as poly(lactic-co-glycolic acid) (PLGA), polycaprolactone (PCL), or polydioxanone (PDO). These polymers are well-characterized for medical applications and possess adjustable degradation profiles, allowing their resorption over defined periods following implantation. Such polymers can be fabricated into thin films, meshes, or tubular sleeves suitable for insertion into Schlemm's canal 104. However, these materials are generally hydrophobic and may require surface modification, including plasma treatment, chemical grafting, or peptide conjugation, to enhance endothelial cell adhesion. Furthermore, while offering improved mechanical robustness compared to hydrogels, solid polymer sleeves may present increased stiffness, necessitating careful engineering to avoid mechanical injury to delicate canal tissues.

In other embodiments, the sleeve may comprise electrospun nanofiber mats formed from materials such as PLGA, gelatin, or silk fibroin. Electrospinning technology enables the fabrication of ultra-thin, highly porous fibrous structures with significant surface area, promoting cell attachment and nutrient diffusion. Such sleeves may conform closely to the geometry of Schlemm's canal 104. However, electrospun mats may be susceptible to mechanical damage under manipulation and may pose challenges in achieving uniform endothelial cell seeding due to their high porosity and delicate structure.

Further contemplated are collagen-based sleeves, which leverage the inherent biocompatibility and cell-binding properties of collagen, a major constituent of the extracellular matrix. Collagen sleeves may be fabricated as thin-walled tubular structures capable of supporting endothelial cell adhesion and growth. However, collagen is subject to relatively rapid enzymatic degradation in vivo and possesses lower mechanical strength compared to synthetic polymers, potentially limiting its durability during surgical handling and post-implantation. Additionally, sourcing and purification of collagen must be managed carefully to minimize the risk of immunogenic reactions.

In yet other embodiments, the sleeve may comprise thermoplastic elastomers (TPEs), including styrene block copolymers and polyurethane elastomers. TPEs offer significant elasticity and mechanical durability, enabling the fabrication of sleeves capable of withstanding bending, stretching, and compressive forces encountered during canaloplasty procedures. Nevertheless, TPEs are generally hydrophobic and exhibit low intrinsic cell adhesion properties, necessitating surface modification techniques such as hydrophilic coatings or bioactive surface treatments to support endothelial cell attachment and viability. Additionally, TPEs are non-degradable, which may require their subsequent removal or careful consideration of their long-term biocompatibility if left in situ.

Further contemplated are bioresorbable shape-memory polymers (SMPs) capable of reversible deformation. SMPs such as poly(F-caprolactone)-based materials may be manufactured in compressed configurations and subsequently expand to conform to Schlemm's canal 104 geometry upon exposure to body temperature. This property allows the creation of sleeves that remain compact during insertion and subsequently expand to establish uniform contact with the canal wall, facilitating endothelial cell delivery. However, SMP fabrication and control over degradation kinetics require advanced manufacturing processes, and care must be taken to ensure that degradation byproducts are biocompatible.

Additionally, this document contemplates the use of hydrophilic coatings applied onto non-hydrogel sleeves. For instance, a base substrate formed from PLGA, polyurethane, or other polymeric materials may be coated with thin layers of hydrophilic substances, including polyethylene glycol (PEG) brushes, hyaluronic acid, or other biocompatible molecules, to promote cell adhesion. This approach combines the mechanical stability of solid polymers with a cell-friendly interface. Nonetheless, the limited thickness of such coatings restricts the total capacity for cell incorporation, and potential risks exist regarding coating delamination during surgical manipulation.

Natural polymers, including silk fibroin and chitosan, are also contemplated. Silk fibroin offers excellent tensile strength and biocompatibility, while chitosan is biodegradable and possesses inherent antimicrobial properties. Both materials may be fabricated into thin, flexible sleeves capable of supporting endothelial cell adhesion. However, these materials can be mechanically fragile, and variations in processing conditions may introduce inconsistencies in material properties.

While hydrogels provide excellent cell viability and controlled release characteristics, they may exhibit excessive swelling and mechanical softness, which is unsuitable for certain applications. Conversely, alternative substrates offer improved mechanical properties and stability but often require additional processing to achieve adequate cell compatibility. The present document, therefore, contemplates the selection and optimization of sleeve materials based on a balance of mechanical performance, biocompatibility, manufacturability, degradation profile, and the specific anatomical constraints of Schlemm's canal 104.

This document further contemplates that any of the aforementioned alternative substrates may be utilized individually or in combination with hydrogel coatings, forming composite sleeves that integrate the desirable properties of both material classes. For example, a solid polymer sleeve may be overlaid with a thin hydrogel layer to enhance cell adhesion while maintaining the sleeve's structural integrity.

Accordingly, the scope of the present document encompasses sleeves and coatings for endothelial cell delivery formed from hydrogels, synthetic polymers, natural polymers, composite materials, or combinations thereof, provided such materials are configured to preserve endothelial cell viability, facilitate controlled cell delivery, and conform to the physical dimensions and functional requirements of Schlemm's canal 104.

TABLE 18

| Comparison of Hydrogel vs. Alternative Sleeve Substrates | | |
| --- | --- | --- |
| Feature | Hydrogel Sleeves | Alternative Substrates |
| Cell Adhesion | Excellent intrinsic adhesion for endothelial cells. | Requires surface modification for adhesion. |
| Mechanical Strength | Soft, easily damaged under shear stress. | Often mechanically stronger and more durable. |
| Swelling Risk | High; must be controlled to avoid canal compression. | Low to none; solid polymers maintain dimensions. |
| Optical Clarity | Generally clear or translucent. | Often opaque unless fabricated very thin. |
| Thickness Control | Excellent; can be made very thin. | More variable; some polymers hard to make ultra-thin. |
| Drug Loading Capability | Very high; hydrogels can embed drugs. | Moderate; surface coatings or matrix embedding needed. |
| Shelf Life | Sensitive to dehydration; may require cryostorage. | Generally better shelf stability; less moisture sensitivity. |

TABLE 18-continued

Comparison of Hydrogel vs. Alternative Sleeve Substrates

| Feature | Hydrogel Sleeves | Alternative Substrates |
| --- | --- | --- |
| Biodegradability | Typically bioresorbable. | Varies; some resorbable, others permanent. |
| Processing Complexity | Moderate; hydrogel chemistry critical. | Higher for shape-memory polymers or electrospun mats. |
| Suitability for Canaloplasty | Proven in ophthalmic use. | Promising but requires further biocompatibility testing. |

Table 18 is a comparison of hydrogel sleeve 204 and alternative polymeric substrates for delivering endothelial cells 208 into Schlemm's canal 104. While hydrogels offer excellent biocompatibility and cell handling properties, alternative substrates may provide superior mechanical stability and predictable sizing.

In-Situ-Forming Hydrogel Coating with Endothelium

In this embodiment, the hydrogel layer forms on the conduit surface during surgery. This can occur via injectable precursors, where two liquid components are mixed and injected into Schlemm's canal 104, where they gel around the conduit. Alternatively, photocurable hydrogels may be used, where a liquid hydrogel precursor is applied to the conduit and polymerized using light (e.g., UV) after placement. Or thermo-responsive hydrogels may be used, the thermo-responsive hydrogels remain liquid at room temperature but gel at body temperature.

In-situ-forming has several advantages, such as being highly conformable to canal anatomy, requiring minimal pre-procedural preparation, and being tailored to patient-specific anatomy intraoperatively. It has several challenges, such as requiring precise timing and surgical technique, the polymerization or gelation kinetics must be fast enough for surgical practicality, and it may produce heat or byproducts that could harm cells or tissue (depending on chemistry).

6.12 Illustrative Example—In Situ Hydrogel Delivery of Endothelial Cells

In one embodiment, endothelial cells are delivered into Schlemm's canal 104 using an in situ-forming hydrogel system administered via a microcatheter during canaloplasty surgery.

A surgeon initiates the procedure by performing standard canaloplasty access to Schlemm's canal 104. Once the microcatheter is inserted circumferentially through the canal lumen, the surgeon prepares a liquid hydrogel precursor solution comprising hyaluronic acid (HA) derivatives. The hydrogel precursor solution is kept in liquid form at room temperature, ensuring ease of injection and handling.

The hydrogel solution is loaded into a syringe or an infusion pump system connected to the proximal end of the microcatheter. The solution may optionally contain endothelial cells suspended within the hydrogel precursor. The cell suspension is typically prepared at a defined cell density, for example, between approximately 2,500 and 3,500 endothelial cells per square millimeter of canal surface area, to achieve effective seeding of the canal wall.

Under direct surgical visualization, the surgeon gently injects the HA-based hydrogel precursor through the conduit's lumen into Schlemm's canal 104. As the liquid hydrogel exits the conduit tip, it flows circumferentially around the conduit shaft. This results in a thin, conforming layer of hydrogel forming along the inner surface of the canal and surrounding the conduit shaft.

6.13 In Situ-Forming and Preloaded Hydrogel Coating Embodiments for Endothelial Delivery This embodiment describes a dual strategy for endothelial cell delivery using advanced hydrogel systems: in situ-forming hydrogels applied intraoperatively and preloaded hydrogel coatings engineered onto microcatheters prior to surgery. Both approaches aim to achieve precise, minimally invasive transfer of viable endothelial cells directly to Schlemm's canal 104, supporting regeneration of the canal's inner lining and promoting long-term restoration of physiologic aqueous humor outflow.

In Situ Hydrogel Formation

In one implementation, endothelial cells are suspended within a hydrogel precursor solution that is introduced into Schlemm's canal 104 through a microcatheter. Gelation is initiated in situ by one of several mechanisms: thermally responsive gelation, in which the hydrogel transitions from a liquid to a gel at physiological temperatures (~37° C.); ionically induced gelation, activated by the native ionic composition of the aqueous humor (e.g., calcium or magnesium ions triggering crosslinking); or photopolymerization, where embedded photoinitiators are activated by a surgical light source (UV or visible spectrum), leading to rapid crosslinking.

These gelation mechanisms enable rapid transformation of the hydrogel, typically within seconds to a few minutes, supporting seamless integration into the surgical workflow. As the gel solidifies within the canal, it immobilizes the endothelial cells in close apposition to the canal wall, optimizing conditions for cell adhesion, survival, and potential engraftment.

Once the gel layer is established, the conduit is carefully withdrawn, leaving a thin hydrogel coating in place. This residual matrix serves multiple functions, include mechanical protection of Schlemm's canal 104 by acting as a cushioning barrier; therapeutic delivery of endothelial cells directly to the tissue surface; and controlled release, as the hydrogel's degradability profile enables gradual exposure and integration of the delivered cells.

Hydrogel thickness in this embodiment can be customized, often ranging from 10 to 50 micrometers, allowing sufficient cell loading without significantly compromising canal patency. Hyaluronic acid (HA)-based hydrogels are particularly suited for this role due to their biocompatibility, viscoelasticity, and natural presence in ocular tissues. PEG-based systems and other FDA-approved materials may also be employed, depending on the surgeon's preference and desired gel properties.

Importantly, this in situ approach offers the surgeon real-time control over hydrogel volume and cell concentration, making it adaptable to variations in Schlemm's canal anatomy, including differences in canal curvature, diameter, or localized fibrosis. It presents a highly customizable method for delivering regenerative therapy in a targeted and reproducible manner.

Preloaded Hydrogel Coatings on Microcatheters

In a complementary embodiment, the hydrogel coating is manufactured directly onto the microcatheter shaft. Endothelial cells 208 are embedded within the hydrogel during production under sterile, GMP-compliant conditions. During surgery, as the conduit is advanced or withdrawn within Schlemm's canal 104, the embedded cells are deposited through direct contact between the hydrogel surface and the canal wall. This promotes cell adherence and mimics the natural endothelial lining.

Several hydrogel materials are suitable for this purpose, each offering specific advantages: polyethylene glycol (PEG) diacrylate provides tunable mechanical and swelling properties with excellent biocompatibility; hyaluronic acid derivatives, naturally occurring in ocular tissue, offer superior hydration and support cell viability; PLGA-based hydrogels are biodegradable and capable of modulating cell release kinetics; and gelatin methacrylate (GelMA) supports cell attachment and mechanical customization through crosslinking density.

Hydrogel coatings are precisely engineered to meet key surgical performance standards, such as thickness control, typically 10-50 μm, to preserve conduit maneuverability and avoid obstruction of Schlemm's canal 104; controlled degradation, designed to release cells steadily rather than in a burst, improving engraftment efficiency; and mechanical resilience, ensuring that coatings remain intact during conduit navigation without premature detachment or damage.

These design parameters make the hydrogel-coated conduit both biologically active and mechanically compatible with canaloplasty workflows. It provides not only regenerative therapeutic benefit but also a reduction in procedural friction, which minimizes trauma and improves handling.

Clinical Relevance

Together, these hydrogel-based delivery strategies, whether applied intraoperatively or pre-manufactured, enable a safe, scalable, and highly effective means of restoring endothelial integrity to Schlemm's canal 104. The dual-functionality of the hydrogel as both a lubricious interface and a therapeutic matrix represents a significant advancement over conventional mechanical-only interventions, positioning this system as a transformative tool in the treatment of glaucoma.

6.14 Surgeon-Prepared Hydrogel Sleeves

In certain embodiments, the hydrogel sleeve 204 used for endothelial cell delivery is not pre-manufactured but instead prepared intraoperatively by the surgeon or surgical team. This flexible, surgeon-driven approach allows for real-time customization of sleeve dimensions, cell concentration, and material properties, enhancing the adaptability of the device to individual patient anatomy and procedural requirements.

The process begins with the mixing of a hydrogel precursor solution, which may consist of biocompatible polymers such as polyethylene glycol diacrylate (PEGDA), gelatin methacryloyl (GelMA), or other approved formulations. If the hydrogel sleeve 204 is intended to deliver endothelial cells 208, these cells are gently suspended into the hydrogel precursor under sterile conditions just prior to application. This ensures cell viability and preserves biological activity during the short time window before implantation.

Next, the hydrogel solution is applied to a sterile mandrel or directly onto the microcatheter shaft by dipping or molding. This step allows the sleeve to be shaped to the desired length and diameter, whether intended for full 360-degree canalization or for targeted segmental delivery. The flexibility of this method supports surgical discretion based on intraoperative findings, such as areas of scarring or localized canal narrowing.

Following the shaping process, the hydrogel is subjected to in situ crosslinking, which stabilizes its structure. Depending on the selected hydrogel chemistry, crosslinking can be initiated via chemical catalysis, thermal activation, or photopolymerization using visible or UV light. In the case of thermo-responsive hydrogels, simple warming to body temperature may be sufficient to induce solidification and adherence to the conduit.

If the hydrogel sleeve 204 is formed separately from the conduit, it is carefully transferred and slid over the conduit shaft in a sterile environment, ensuring proper alignment and structural integrity. The resulting sleeve is then ready for immediate deployment into Schlemm's canal 104.

Because these surgeon-prepared hydrogel sleeves 204 are freshly created, they are not intended for storage or reuse and must be used immediately following fabrication. This approach eliminates concerns related to long-term bioburden or shelf-life stability, and instead supports a personalized, procedure-integrated application of the technology.

Overall, the surgeon-prepared hydrogel sleeve 204 embodiment offers a versatile and scalable option within the platform. It empowers clinicians with on-demand fabrication capabilities that can respond to patient-specific anatomy, intraoperative variables, or procedural complexity, without sacrificing biocompatibility, safety, or therapeutic efficacy.

6.15 Deployment Process of Hydrogel Sleeves in Schlemm's Canal

Whether using a pre-manufactured hydrogel sleeve 204 or a surgeon-prepared version created intraoperatively, the deployment of the sleeve into Schlemm's canal 104 follows a carefully controlled sequence that ensures optimal contact between therapeutic materials and the canal wall.

The process begins with the preparation phase, during which the hydrogel sleeve 204 is either removed from sterile packaging or freshly formed directly onto the conduit shaft using in situ crosslinking techniques. In cases where the sleeve is fabricated separately, it is gently slid over the conduit under sterile conditions, aligned precisely along the segment of the shaft that will interface with Schlemm's canal 104. Proper positioning is necessary, as it ensures that endothelial cells 208, if present, will be delivered uniformly along the intended length of the canal.

Once prepared, the conduit-sleeve assembly is introduced into Schlemm's canal 104 through a small surgical access point, such as a goniotomy incision. The surgeon carefully advances the device circumferentially within the canal lumen, guiding it along the natural curvature of the canal while preserving the integrity of the surrounding trabecular meshwork 106 and endothelium.

As the conduit progresses through the canal, the hydrogel sleeve 204 makes direct contact with the inner wall, facilitating the transfer of endothelial cells 208, nutrients, or therapeutic agents embedded within the hydrogel matrix. This stage is particularly important for achieving uniform cell seeding and ensuring maximum surface engagement. The advancement may be performed in a continuous sweep or in incremental steps, depending on the surgeon's preference and the specific geometry of the canal.

Following delivery, the hydrogel sleeve 204 may behave in one of two ways, depending on its design characteristics. In some embodiments, the sleeve is designed to remain in place, adhering to the canal wall and providing a sustained release of its cellular or pharmacological payload. In other cases, the sleeve is engineered to partially disintegrate or remain as a thin coating, detaching from the conduit shaft as it is withdrawn, leaving behind a bioactive hydrogel film that continues to support regeneration.

Upon completing the desired treatment span, whether a full 360 degrees or a targeted segment, the surgeon withdraws the conduit from the canal. The result is a precisely delivered hydrogel intervention that offers mechanical protection during deployment, ensures uniform circumferential contact, and supports long-term integration of endothelial cells or other therapeutic agents.

To enhance the safety and efficacy of cell-based delivery, the hydrogel matrix may be structurally modulated to support the uniform spatial distribution of endothelial or other therapeutic cells. These modifications include the incorporation of pore networks or internal scaffolding geometries that inhibit excessive cell clustering and promote even dispersion throughout the canal. In certain embodiments, the hydrogel is engineered with controlled release kinetics, allowing therapeutic cells or agents to be released gradually over time rather than in a concentrated burst. This reduces the risk of sudden aggregation, local obstruction, or asymmetric therapeutic exposure.

To enable real-time procedural feedback, the hydrogel formulations are made optically compatible with OCT and OCTA imaging, facilitating noninvasive monitoring of deployment, distribution, and swelling behavior. These imaging modalities allow clinicians to identify regions of hyperreflectivity that may correspond to unwanted cell buildup, providing an opportunity for timely correction or dosage modulation.

Additionally, viability assays are performed during hydrogel preparation to confirm the functional integrity of encapsulated cells. These include markers of apoptosis, membrane integrity, and metabolic activity to ensure that only viable and therapeutically active cells are delivered to the canal environment. This multi-layered strategy ensures the hydrogel serves as a biofunctional and precision-guided platform for safe regenerative therapy.

This deployment method, applicable to both pre-formed and intraoperatively constructed sleeves, highlights the adaptability to diverse surgical workflows and canal geometries. By combining ease of use with therapeutic precision, the hydrogel sleeve 204 approach provides a promising tool for restoring Schlemm's canal 104 function in glaucoma treatment.

Deployment and Disengagement Methodology of Hydrogel Sleeve from Canaloplasty Catheter In the disclosed embodiment, the hydrogel sleeve 204 is pre-loaded onto the distal segment of a flexible canaloplasty catheter. The methodology of deployment and disengagement includes the following steps:

1. Preparation and Insertion. The hydrogel sleeve 204 in a dehydrated or semi-hydrated compressed state. is affixed circumferentially around the distal shaft of the catheter 202. The catheter 202 is inserted ab interno through a corneal incision into Schlemm's canal 104 using standard microcatheterization techniques. Navigation through the canal may be facilitated by viscoelastic injection, transillumination, or OCT guidance. In other embodiments, ab externo routes of access, including corneal, scleral, or other incisions may provide access to Schlemm's canal.

2. Advancement through Schlemm's Canal. As the catheter 202 advances circumferentially through Schlemm's canal 104, the hydrogel sleeve 204 remains securely positioned due to functional fit or temporary biodegradable tethering. The hydrogel remains in a compact state to minimize canal trauma and preserve visibility and control.

3. Controlled Hydration and Expansion. Upon reaching the intended delivery site, commonly a segment spanning 90° to 180°, a hydration trigger is initiated. This may be achieved through passive absorption of aqueous humor, controlled infusion of sterile saline or BSS via an integrated lumen, or local application of a hydrating agent using a dual-lumen catheter design. Hydration activates the hydrogel, causing it to swell and gently press against the trabecular meshwork 106 and the inner wall of Schlemm's canal 104.

4. Disengagement Mechanism. Once the hydrogel sleeve 204 has fully expanded and anchored to the canal wall, disengagement from the catheter is facilitated by catheter retraction, the gentle withdrawal leaves the sleeve in situ; sheath-assisted release, a retractable external sheath is removed first, freeing the sleeve; or thermoresponsive or enzymatic release, where a dissolvable tether disengages the sleeve once deployed.

5. Post-Deployment Positioning and Confirmation. Following deployment, the hydrogel sleeve 204 conforms to the canal curvature, optionally releasing therapeutic agents and facilitating endothelial cell migration. OCT imaging or gonioscopy may be used to confirm appropriate placement and canal patency.

The illustrated methodology presents a clinically adaptable strategy for deploying a hydrogel sleeve 204 from the distal end of a canaloplasty catheter 202 to deliver therapeutic agents within Schlemm's canal 104. The process begins with insertion of the catheter 202 bearing a compressed, dehydrated hydrogel sleeve 204, carefully navigated through the canal using viscoelastic guidance or OCT imaging. As the catheter 202 advances circumferentially, the hydrogel remains in position due to frictional fit or temporary adhesive properties.

Upon reaching the targeted segment of the canal, hydration is initiated, either through passive aqueous uptake or via controlled infusion through a single- or dual-lumen design. The hydrogel swells in situ, conforming to the canal's inner wall and gently expanding to support contact with the trabecular meshwork 106, while preserving space for aqueous outflow.

Disengagement of the hydrogel sleeve 204 may be achieved through multiple mechanisms, including catheter retraction, sheath-assisted release, or enzymatically responsive tethers that dissolve upon exposure. Following deployment, the sleeve conforms to the canal curvature, enabling sustained contact for drug delivery or endothelial cell migration. Imaging confirmation using OCT or gonioscopy ensures proper positioning and patency, underscoring the technique's precision and safety. This system represents a transformative advancement in minimally invasive glaucoma surgery, combining mechanical precision with biologically active regeneration.

6.16 Hydrogel as a Temporary Cell Reservoir

One aspect of the present document is the use of a hydrogel matrix loaded with endothelial cells 208 and applied either as a coating or sleeve on the microcatheter. During surgery, this hydrogel maintains intimate contact with the inner wall of Schlemm's canal 104, providing a physical medium through which endothelial cells 208 can be transferred to the tissue.

Even if the conduit remains in place only briefly, the hydrogel serves as a local reservoir that retains the cells adjacent to the target tissue. Following conduit withdrawal, the hydrogel may continue to release endothelial cells 208 gradually over a period of minutes to hours, allowing cell transfer to persist even after the surgical manipulation has concluded.

6.17 Controlled Release Properties of Hydrogels

Hydrogels can be precisely engineered to facilitate controlled, slow release of endothelial cells 208 rather than releasing them all at once. This can be accomplished through several mechanisms, such as diffusion-based release, where cells migrate out of the hydrogel matrix into surrounding tissue; enzymatic degradation, where specific enzymes in the ocular environment gradually break down the hydrogel, liberating embedded cells; and swelling-controlled release, whereby hydrogel expansion under physiological conditions enables a regulated discharge of cells.

These mechanisms collectively extend the time frame of endothelial cell exposure to Schlemm's canal 104 beyond the immediate surgical window, increasing the likelihood of successful cell integration and regeneration.

6.18 Advantages of High Local Cell Concentration

Unlike systemic therapies, which disperse cells throughout the entire body, the hydrogel approach places endothelial cells 208 directly against the inner wall of Schlemm's canal 104. This targeted, localized delivery achieves cell concentrations at the tissue interface that are orders of magnitude higher than those achieved through systemic administration, enabling effective cellular therapy even with relatively short physical contact times.

A few minutes of high local concentration can produce biological effects that would otherwise require prolonged systemic exposure, thereby amplifying the therapeutic impact of the procedure while minimizing systemic risks.

6.19 Examples of Endothelial Regenerative Embodiments

Example 1—Conduit Hydrogel Coating

A conduit was dip-coated with PEG-diacrylate hydrogel loaded with $1\times10^6$ endothelial cells/mL. The conduit was threaded through an ex vivo human eye model. OCT imaging showed uniform gel transfer to Schlemm's canal 104 walls.

Example 2—Hydrogel Sleeve Deployment

A hydrogel sleeve 204 was formed around a conduit shaft, measuring 250 μm outer diameter. Upon placement and conduit withdrawal, the sleeve remained circumferentially in Schlemm's canal 104, confirmed by histological sectioning.

Example 3—Injectable Hydrogel

An HA-based hydrogel loaded with endothelial cells was injected into Schlemm's canal 104 through a microcatheter in an ex vivo model. Post-injection, the gel maintained canal patency, and cell viability exceeded 85% at 24 hours.

Example 4—AI Guidance

AI algorithms processed intraoperative OCT images, identifying canal segments lacking endothelial coverage. Targeted hydrogel delivery was performed only in these segments, minimizing total cell dose.

6.20 Nanotechnology-Enhanced Strategies for Canal Endothelialization

The system may be further optimized through the integration of nanotechnology, enabling precise control over endothelial cell behavior, therapeutic agent delivery, and structural conformation within Schlemm's canal 104. Nanotechnology-based modifications enhance the interface between the hydrogel system and the native canal wall, creating a bioresponsive and regenerative environment tailored for intraocular application.

One principal embodiment involves the incorporation of embedded nanopores-nanoscale channels or cavities ranging from 20 to 200 nanometers in diameter, within the hydrogel matrix. These nanopores serve as microscale reservoirs for the storage of therapeutic agents, such as anti-fibrotic compounds, growth factors, or cell adhesion modulators. Controlled pore size and distribution enable predictable diffusion kinetics, facilitating gradual and sustained release of agents in situ. This slow-release mechanism reduces dosing frequency while maximizing therapeutic bioavailability at the target site.

Another feature involves nanoscale ridges or grooves, ranging from 100 to 800 nanometers in width and 50 to 500 nanometers in depth, embossed into the surface of the hydrogel that interfaces with the Schlemm's canal endothelium. These aligned nanoridges provide directional cues for endothelial cell migration and elongation, encouraging the formation of an ordered, functional cellular monolayer. This is especially beneficial in regenerative scenarios where cell guidance and contact inhibition are essential to reestablishing canal integrity.

In certain embodiments, the hydrogel surface may include nanofibrous coatings or electrospun nanofibers that mimic the native extracellular matrix. These fibers, typically ranging from 50 to 400 nanometers in diameter, offer biochemical and topographical signals to promote cell adhesion, viability, and junction formation. The nanofibrous layer may be impregnated with peptides or protein motifs such as RGD (arginine-glycine-aspartate) to further enhance cell attachment and spreading.

Additional nanotechnology features may include nanosensors embedded within the hydrogel scaffold that respond to changes in pH, pressure, or oxygen tension-indicating early signs of fibrosis, ischemia, or implant degradation. These sensors may be fabricated using biocompatible quantum dots, carbon nanotubes, or silicon nanowires, ranging from 10 to 100 nanometers in scale.

Together, these nanotechnology-enabled designs create a multifunctional scaffold capable of supporting precise endothelial cell alignment, sustained therapeutic delivery, dynamic tissue interaction, and real-time sensing. Such capabilities advance into the frontier of adaptive, personalized glaucoma therapy.

6.21 PEGylation and Immunoinert Nanocoatings

To further enhance biocompatibility and minimize adverse immune responses within Schlemm's canal 104, certain embodiments of the disclosed hydrogel-based system may incorporate immunoinert nanocoatings. These include PEGylated (polyethylene glycol-modified) surface layers applied to either the hydrogel matrix or underlying conduit. PEGylation is known to reduce protein adsorption and cellular recognition by the host immune system, thereby extending device residence time and improving tolerability. Nanostructured PEG domains may be covalently tethered to hydrogel backbones or incorporated via layer-by-layer deposition methods, yielding surfaces that resist fibrotic encapsulation and local inflammation. Such coatings are especially advantageous in applications requiring prolonged implantation, repeated procedures, or where canal trauma must be minimized. These embodiments may be further modified to include zwitterionic or polysaccharide-based nanocoatings that similarly reduce immunogenicity while preserving the hydrogel's mechanical and bioactive functions.

TABLE 19

| | Nanotechnology Embodiments for Schlemm's Canal Regenerative Therapy | | |
|---|---|---|---|
| Nanotechnology Feature | Description | Functional Purpose | Size/ Dimension Range |
| Nanoporous Hydrogel Matrix | Hydrogel structure embedded with interconnected nanopores to retain and release therapeutic agents. | Sustained release of growth factors, cytokines, or anti- inflammatory compounds to enhance endothelialization. | 10-100 nm pore diameter |
| Nanoridges for Cell Guidance | Aligned nanoscale ridges fabricated along the inner surface of the hydrogel sleeve. | Promotes directional migration and alignment of Schlemm's canal endothelial cells. | 50-200 nm ridge spacing |
| Nanotopography Modulation | Surface patterning at the nanoscale to mimic the natural extracellular matrix. | Enhances cellular adhesion, spreading, and phenotype retention of implanted endothelial cells. | 20-300 nm feature height/depth |
| Nanoparticle Incorporation | Incorporation of biodegradable nanoparticles within the hydrogel matrix. | Facilitates co-delivery of signaling molecules or imaging agents. | 80-150 nm particle diameter |
| Nanosensor Doping | Integration of smart nanosensors responsive to environmental changes (e.g. pH, oxygen) | Enables real-time monitoring of hydrogel degradation or cell viability. | 50-200 nm sensor unit size |
| Nanochannel Delivery Networks | Engineered nanochannels withing the hydrogel wall. | Regulates spatial and temporal distribution of therapeutic payloads across the canal. | 50-100 nm channel diameter |

Table 19 outlines a series of nanotechnology strategies integrated into the hydrogel-based system to optimize endothelialization, therapeutic delivery, and structural compatibility within Schlemm's canal 104. These nanotechnology-based features may be incorporated into coatings, sleeves, or other therapeutic devices deployed within Schlemm's canal 104.

Figure 7:
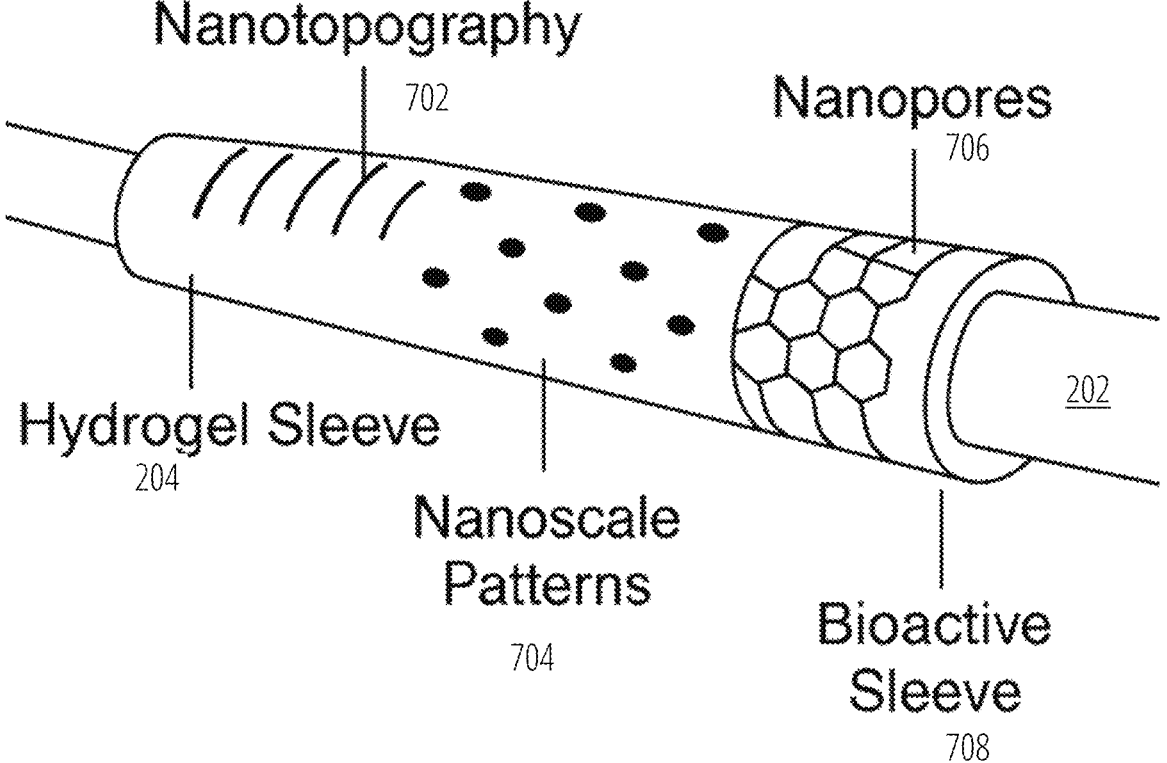
FIG. 7 illustrates a schematic representation of a hydrogel sleeve.

FIG. 7 is a schematic representation of a hydrogel sleeve featuring integrated nanotechnology for regenerative therapy in Schlemm's canal 104. The illustrated embodiment includes embedded nanopores 706 functioning as drug reservoirs for controlled release, nanoscale ridges 702 to promote guided endothelial cell migration, and a hydrogel matrix enveloping the delivery conduit. The hydrogel sleeve 204 in this embodiment also includes nanoscale patterns 704 and a bioactive sleeve 708. The system is configured to conform to the anatomical dimensions of Schlemm's canal 104 while supporting endothelial repopulation and sustained therapeutic delivery.

The FIG. 8 flowchart outlines the procedural sequence for implementing hydrogel-based regenerative therapy in Schlemm's canal 104. It includes key stages from device preparation and endothelial cell viability assessment to targeted hydrogel delivery, OCT/OCTA monitoring, and postoperative AI-assisted follow-up. The flow emphasizes precision deployment, imaging-guided adjustments, and safety checkpoints to optimize therapeutic outcomes while minimizing canal obstruction or endothelial loss.

The sequence begins with preoperative planning 802, evaluating the patient's eligibility and identifying the target canal segments. The next step is hydrogel preparation 804, loading the endothelial cells 208, and conducting viability assays. Device assembly 806 comes next, integrating the hydrogel onto the catheter 202 sleeve. Then, the intraoperative imaging 808 uses OCT/OCTA for canal visualization. The sequence then includes catheter insertion 810 and the navigation of Schlemm's canal 104 to the target site. Hydrogel deployment 812 is the next step, releasing the hydrogel under OCT guidance. This is followed by postoperative monitoring 814, which uses OCT/OCTA to confirm patency and cell distribution. AI integration 816 is an optional aspect of the sequence, analyzing imaging to flag issues and adjust future dosing.

7.0 PHYSIOLOGICAL IMPORTANCE OF SCHLEMM'S CANAL ENDOTHELIUM

Schlemm's canal 104 is a delicate, circumferential structure fundamental to the regulation of aqueous humor outflow and intraocular pressure (IOP). Under normal conditions, its endothelial lining exhibits a native cell density estimated at approximately 3,000 to 6,000 cells per square millimeter, a figure similar in magnitude to corneal endothelial densities. These specialized endothelial cells serve essential physiological functions, including maintaining a semi-permeable barrier between aqueous humor and the collector channels, regulating transcellular fluid passage via giant vacuoles and intracellular pores, and preserving low hydraulic resistance within the outflow pathway.

7.1 Anatomical and Volumetric Considerations

Anatomically, Schlemm's canal 104 features a lumen diameter typically ranging from about 190 micrometers to 370 micrometers, resulting in a very limited internal volume. For a full 360-degree canal length of roughly 35 millimeters, the total inner surface area can range from approximately 30 to 40 square millimeters, depending on diameter. These constraints place strict limits on how much hydrogel volume and how many endothelial cells may be introduced safely. Overfilling Schlemm's canal 104 with excessive hydrogel or excessive cellular density risks mechanical trauma, lumen obstruction, elevated IOP, and occlusion of collector channel ostia.

7.2 Risks of Excessive Cell Density

While endothelial cell delivery into Schlemm's canal 104 offers regenerative potential, there are significant biological and mechanical risks associated with excessive cell density:

Lumen Obstruction: Excessive cells or cell aggregates can physically block the canal lumen, impeding aqueous outflow and elevating IOP.

Aggregation-Induced Stenosis: Dense clusters or cell sheets may cause localized narrowing, leading to segmental blockages within Schlemm's canal 104, particularly if hydrogel properties promote cell clustering or if non-viable cells accumulate as debris.

Ischemic Stress: Excessive cell layering can hinder oxygen and nutrient diffusion within canal wall tissues, raising the risk of hypoxic injury, inflammation, or fibrosis.

Inflammatory Response: Excess cellular debris or apoptotic cells may trigger localized immune responses, undermining the regenerative effect.

For these reasons, regenerative procedures across ophthalmology and vascular surgery often limit surface seeding densities to around 5,000 cells per square millimeter or less to prevent excessive layering.

Conversely, introducing excessively high endothelial cell densities into hydrogel matrices creates several risks. High cell concentrations can promote aggregation and clumping, resulting in focal or diffuse blockage of the canal lumen and leading to mechanical obstruction of aqueous outflow. Dense cell clusters can impede nutrient and oxygen diffusion into surrounding tissues, causing localized ischemic injury, endothelial cell death, or fibrosis.

Furthermore, excessive cellular load may provoke immune responses, triggering inflammation that narrows the canal or damages newly seeded endothelial layers. Cells may also fail to adhere properly under conditions of high cell density, risking detachment due to fluid shear stress and potential downstream obstruction of collector channels. Clinically, excessive endothelial cell density can present as acute postoperative IOP spikes, visible narrowing of Schlemm's canal during gonioscopy, or heightened anterior chamber inflammation.

7.3 Risks of Low Cell Density

Delivering too few endothelial cells into Schlemm's canal 104 can result in incomplete coverage of the canal wall, leaving exposed regions vulnerable to fibrosis, scarring, and permanent narrowing. Sparse cellular coverage reduces the formation of transcellular pores, thereby elevating outflow resistance and potentially leading to persistently elevated IOP. Exposed stromal regions also increase susceptibility to inflammatory responses, which can accelerate scar formation and compromise canal patency. Although low cell density might not produce immediate symptoms, it can manifest clinically as a gradual elevation of IOP or structural changes within Schlemm's canal 104 over time.

7.4 Canal Volume and Dosing Calculations for Safe Therapeutic Delivery

Safe dosing is necessary to avoid lumen obstruction or postoperative stenosis. Schlemm's canal 104 has a typical inner diameter of ~190-350 μm and an estimated volume of ~1μ-5 μL.

To guide precise dosing, the system employs individualized calculations of canal volume using OCT-derived metrics:

$$\text{Canal Volume (μL)} = \text{Cross-sectional area (mm}^2) \times \text{Treatment length (mm)}$$

If a target seeding density of 3,000 cells/mm² is selected, the total number of cells can be calculated by multiplying this target by the measured internal surface area of the treated canal segment. This ensures that endothelial delivery remains within physiologic ranges and minimizes the risk of overfilling or hydrogel-induced stenosis.

Determining a safe yet therapeutically effective endothelial cell dose requires balancing canal geometry with biological requirements. A practical ceiling of approximately 5,000 cells per square millimeter is often used as a safe upper limit.

For example, consider a full 360-degree segment of Schlemm's canal 104 with an internal diameter of 250 micrometers. The canal's inner circumference would be π×diameter (approximately 0.785 mm), and for a length of 15 millimeters, the surface area would be about 11.8 mm². At 5,000 cells per square millimeter, this would translate to roughly 59,000 cells for the treated segment.

Strategies to avoid overdosing include segmented delivery, hydrogel carriers with controlled cell release, and AI-guided dosing based on patient-specific canal volume measurements.

7.5 Mathematical Modeling for Safe Endothelial Cell Dosing

Calculations show:

$$V = \pi \times (d2)^2 \times L \text{ For } d=250 \text{ μm and } L=36 \text{ mm:}$$

$$V \approx 1.77 \text{ μL}$$

Each endothelial cell has an approximate volume of:

$$V\text{cell} = (4/3\pi \times (d\_\text{cell}/2)^3$$

For a 15 μm cell:

$$V\text{cell} \approx 1.77 \times 10^{-6} \text{ mm}^3$$

Hence, maximum cell count:

$$\text{Max Cells} \approx 1.77 \text{ μL}/1.77 \times 10^{-6} \text{ mm}^3 \text{ 1,000,000 cells}$$

However, to avoid crowding and aggregation, safe doses are significantly lower, typically:

$1 \times 10^5$ to $1 \times 10^7$ cells/mL

Total dose preferably $\leq 1 \times 10^6$ cells per eye

Canal Volume Estimation for Endothelial Delivery

To ensure safe and effective delivery of endothelial cells into Schlemm's canal 104, it is necessary to understand the canal's physical capacity. Mathematical modeling provides a useful framework to estimate the total volume of Schlemm's canal 104 and to calculate the maximum number of cells that can be delivered without impairing the canal's ability to conduct aqueous humor.

Anatomically, Schlemm's canal 104 resembles a narrow cylindrical tube, allowing it to be approximated as such for modeling purposes. Assuming an average canal diameter of 250 micrometers (μm) and a circumferential length of approximately 37.7 millimeters (mm), the total volume of the canal can be estimated using the formula for the volume of a cylinder:

$$V_{canal} = \pi \times r^2 \times h$$

where r is the radius (125 μm) and h is the length (37,700 μm). This yields a canal volume of approximately $1.85 \times 10^9$ μm³, or about 1.85 microliters (μL), indicating that the entire Schlemm's canal holds less than 2 μL when treated over 360 degrees.

To estimate how many cells this volume can support, we consider the average volume of a single endothelial cell. A cell with a 15 μm diameter has a calculated volume of approximately 1,767 μm³, assuming a spherical shape. Dividing the total canal volume by the volume of a single cell results in a theoretical maximum capacity of about $1.05 \times 10^6$ cells (i.e., approximately one million cells) if the canal were to be completely filled with cells alone.

It is important to note that this figure represents an absolute maximum and does not account for the presence of hydrogel matrices, carrier fluids, or extracellular spacing, all of which are essential for physiological compatibility. Therefore, practical dosing strategies would deliver a substantially lower number of cells to avoid canal obstruction and to maintain normal outflow dynamics.

While this figure represents the upper physical limit, clinically it would be unsafe and biologically impractical to fill the canal entirely with cells. Doing so would obstruct fluid dynamics essential for intraocular pressure regulation and likely lead to iatrogenic complications. Accordingly, only a fraction of this total, typically around 10%, would be considered a safe, functional loading threshold for therapeutic applications.

Physiologically Safe Endothelial Cell Load

Assuming that no more than 10% of Schlemm's canal 104 volume should be occupied by delivered endothelial cells to maintain safe aqueous outflow, the estimated safe number of cells is approximately 104,700. This value is derived from the previously calculated maximum canal capacity and cell volume. The assumption that only a small fraction of Schlemm's canal 104 should be occupied to maintain fluid patency is medically and surgically reasonable.

To contextualize this within the canal's surface area, the total internal area of Schlemm's canal 104 is estimated at about 29.6 mm$^2$. When the safe cell load of 104,700 cells is distributed evenly across this area, the resulting cell density is approximately 3,537 cells per mm$^2$.

This calculated density closely mirrors physiologic endothelial cell densities observed in native ocular tissues and aligns with established targets in corneal transplant protocols, which typically aim for densities between 2,500 and 3,500 cells/mm$^2$. As such, this modeling supports the safety and biological plausibility of the proposed cell dosing strategy for regenerative therapy within Schlemm's canal 104. The volume of hydrogel needed to carry these cells can be calculated from the hydrogel's carrying capacity.

densities observed in ocular tissues and corneal transplant practices. This model serves as a rational foundation for dosing decisions in regenerative canal-based therapies.

Hydrogel Volume Calculations for Endothelial Cell Delivery

One step in preparing endothelial cell delivery systems is determining the precise volume of hydrogel required to carry the desired number of cells at the targeted cell concentration. This calculation ensures that the hydrogel-cell mixture remains within the anatomical and physiological limits of Schlemm's canal 104 while delivering an effective therapeutic dose.

The required hydrogel volume can be calculated as follows:

Hydrogel Volume Required (in microliters)=Total Cell Count divided by Cell Concentration (in cells per microliter).

Expressed Mathematically:

$$\text{Hydrogel Volume Required } (\mu L) = \frac{\text{Total Cell Count}}{\text{Cell Concentration (cells}/\mu L)}$$

Example Calculation: Suppose the surgical plan requires delivery of a total of 50,000 endothelial cells, and the hydrogel suspension is prepared to contain 5,000 cells per microliter. The hydrogel volume required is calculated as:

$$\text{Hydrogel Volume Required } (\mu L) = \frac{50,000}{5,000} = 10 \ \mu L$$

Thus, 10 microliters of hydrogel precursor solution would be prepared and loaded with the endothelial cells to achieve the intended dosing.

TABLE 20

| Canal Volume and Safe Cell Load Estimation | | |
|---|---|---|
| Parameter | Value | Notes |
| Canal Diameter | 250 μm | Typical average diameter of Schlemm's canal |
| Canal Circumference | 37.7 mm | Estimated for full 360° treatment |
| Canal Volume (V$_{canal}$) | ≈1.85 × 10$^9$ μm$^3$ (1.85 μL) | Approximated as a cylindrical structure |
| Single Cell Volume (V$_{cell}$) | ≈1,767 μm$^3$ | Based on 15 μm diameter cell |
| Max Cell Capacity (N$_{max}$) | ≈1.047 × 10$^6$ cells | Absolute maximum if packed without space |
| Safe Cell Load (10%) | ≈104,700 cells | Estimated for 10% canal occupancy |
| Canal Surface Area | ≈29.6 mm$^2$ | Internal surface area of Schlemm's canal |
| Safe Cell Density | ≈3,537 cells/mm$^2$ | Aligns with corneal endothelial density |

Table 20 provides a mathematical model to estimate the safe number of endothelial cells that may be delivered into Schlemm's canal 104 without risking luminal obstruction. Using a cylindrical approximation of the canal (250 μm diameter, 360° length≈37.7 mm), the total canal volume is estimated at approximately 1.85 μL. Based on the average volume of a m-diameter endothelial cell (~1,767 μm$^3$), the theoretical maximum cell capacity exceeds one million cells. However, to preserve aqueous humor outflow and avoid iatrogenic blockage, only about 10% of this volume is considered safe for cellular delivery. This yields a recommended safe load of approximately 104,700 cells, translating to a cell density of ~3,537 cells/mm$^2$ across the canal's inner surface, well aligned with physiological endothelial This calculation serves several important purposes: it ensures the volume injected does not exceed the physical capacity of Schlemm's canal 104, which ranges in diameter from approximately 190 μm to 370 μm. It also allows precise control over endothelial cell dosing, minimizing the risk of excessive cell density that could cause canal obstruction or elevated intraocular pressure. And it provides flexibility to adjust the hydrogel formulation intraoperatively based on patient-specific anatomy or surgeon preference.

Maintaining this balance between total cell count and hydrogel volume is a necessary element of safe and effective regenerative canaloplasty.

Hydrogel carriers typically load between 10,000 and 20,000 cells per microliter, so delivering 60,000 cells would require approximately 3 to 6 μL of hydrogel. This volume remains feasible within the canal's geometry for partial treatments and can be adjusted for segmental approaches.

7.6 Hydrogel Coatings

Hydrogel coatings 602 applied directly to the conduit surface are limited in thickness to avoid increasing conduit diameter beyond safe limits. Coatings are generally engineered at ≤20 micrometers per side, ensuring the conduit remains maneuverable within Schlemm's canal 104 lumen.

Target endothelial cell densities for coatings typically range from approximately 2,000 to 4,000 cells per square millimeter of hydrogel surface. This range balances the following factors: maintaining a thin, uniform coating that does not excessively enlarge conduit diameter; providing sufficient cell loading for regenerative purposes; and avoiding localized areas of excessive cell density that might clump during conduit navigation.

For example, a conduit with a bare diameter of 200 micrometers would become approximately 230 micrometers in diameter after adding two hydrogel layers of 15 micrometers each. This remains compatible with Schlemm's canal 104, which in many regions has a diameter of at least 250 micrometers.

7.7 Hydrogel Sleeves

Hydrogel sleeves 204 offer greater volumetric capacity than thin coatings, enabling higher cell loading without necessarily exceeding dimensional constraints. Typical target cell densities for sleeves range from 2,500 to 5,000 cells per square millimeter of sleeve surface area.

Sleeves also provide the ability to act as reservoirs, releasing endothelial cells 208 gradually for sustained integration, greater design flexibility, as wall thickness can be adjusted to balance cell loading capacity with lumen compatibility, and potential to minimize shear stress on cells during conduit movement, improving cell viability.

Hydrogel sleeves 204 must still adhere to swelling constraints. Hydrogel swelling beyond 5% to 10% of the nominal diameter can risk lumen occlusion. Thus, sleeves are designed with stable, crosslinked hydrogel matrices to control swelling kinetics.

7.8 Injectable Hydrogel Suspensions

Injectable hydrogels offer the greatest flexibility for cell delivery because both volume and cell concentration can be adjusted intraoperatively. Suspensions often target cell concentrations of approximately 10,000 to 20,000 cells per microliter.

Key considerations for injectable suspensions include tailoring the injected volume to match the specific patient's canal size, ensuring rapid gelation to prevent migration of hydrogel into unintended spaces, and maintaining hydrogel porosity and hydration to support cell viability.

Suspensions still observe the same density limits as coatings and sleeves. Overfilling the canal, even with injectable materials, risks lumen occlusion, collector channel obstruction, or increased IOP.

7.9 Techniques for Controlling Density of Endothelium in Schlemm's Canal

Achieving an optimal endothelial cell density within Schlemm's canal 104 is essential for successful regenerative canaloplasty. Whether endothelial cells 208 are delivered using hydrogel coatings 602, hydrogel sleeves 204, or injectable suspensions, the process demands precise control over both the quantity of cells introduced and their uniform distribution along the canal wall. Careful mathematical planning and engineering solutions enable this level of precision.

The process begins with the preparation of a cell suspension at a known concentration. The desired cell density, typically expressed in cells per square millimeter, determines how many total cells must be delivered for the segment of Schlemm's canal 104 being treated. For example, if the target is to deliver 3,000 cells per square millimeter over a canal segment with a surface area of 12 mm$^2$, the total number of endothelial cells required is calculated by multiplying the target density by the surface area. This yields:

$$\text{Total Cell Count} = \text{Target Density} \times \text{Canal Surface Area}$$
$$\text{Total Cell Count} = 3{,}000 \text{ cells/mm}^2 \times 12 \text{ mm}^2 = 36{,}000 \text{ cells}$$

Once the total cell requirement is determined, the precise volume of hydrogel precursor needed to carry these cells can be calculated based on the intended cell concentration of the injectable hydrogel. The required hydrogel volume is obtained by dividing the total number of cells by the cell concentration, as shown in the equation:

$$\text{Hydrogel Volume Required (μL)} = \text{Total Cell Count} \div \text{Cell Concentration (cells/μL)}$$

For instance, if the cell suspension is prepared at 4,000 cells per microliter, the hydrogel volume required would be:

$$\text{Hydrogel Volume Required} = 36{,}000 \text{ cells} \div 4{,}000 \text{ cells/μL} = 9 \text{ μL}$$

This ensures that only the necessary volume is introduced into the canal, minimizing the risk of overfilling and maintaining compatibility with Schlemm's canal 104 dimensions.

In the case of pre-formed hydrogel coatings 602, volumetric control is achieved by precisely regulating the thickness of the hydrogel layer. Hydrogel coatings 602 are typically engineered not to exceed 20 micrometers per side to ensure that the overall diameter of the coated conduit remains within safe limits compatible with the canal's dimensions. Coating techniques such as controlled dipping or spraying are used to deposit a uniform hydrogel layer around the conduit surface. Post-coating inspections, often performed via confocal microscopy or optical coherence tomography, confirm the uniformity of both the hydrogel thickness and the distribution of cells within the matrix.

For hydrogel sleeves 204, the manufacturing process similarly emphasizes tight dimensional control. Hydrogel sleeves 204 are fabricated using mandrels or molds that define their inner and outer diameters with precision. By adjusting wall thicknesses—typically kept between 20 and 30 micrometers per side unless anatomical allowances permit thicker structures—manufacturers can balance the sleeve's cell-carrying capacity with the need to maintain an overall conduit diameter that fits safely within Schlemm's canal 104. The advantage of sleeves lies in their potential for higher volumetric capacity than thin coatings, enabling greater cell loading while still preserving navigability through the canal.

Ensuring a uniform cell distribution within the hydrogel is necessary to prevent localized cell crowding, clumping, or mechanical obstruction. To achieve this, gentle mixing protocols are designed to disperse cells evenly while avoiding shear stress that could damage fragile cell membranes. In many cases, dual-barrel syringe systems are employed, where one barrel contains the hydrogel precursor and the other contains the concentrated cell suspension. These two components are mixed immediately before injection, ensuring that the cells remain viable and evenly distributed without prolonged exposure to the hydrogel's crosslinking agents. Micropipette techniques may also be used during the preparation phase to transfer small, precise volumes of cell suspension for lower-cell-load applications.

The flexibility of in situ hydrogel systems allows surgeons to make real-time adjustments during surgery. For example, if the surgeon observes that the canal diameter is narrower than anticipated, the injection volume can be reduced, or the cell concentration lowered, thereby minimizing the risk of excessive lumen filling or canal distension. Conversely, in areas with localized fibrosis or suspected endothelial damage, the surgeon may elect to increase cell density locally to enhance regenerative potential.

When delivering endothelial cells circumferentially, accurate estimation of Schlemm's canal 104 surface area becomes crucial. The inner surface area of the canal can be approximated by multiplying its circumference by the length of the treated segment. For instance, assuming a canal diameter of 250 micrometers (0.25 mm) and a treatment length of 30 mm, the circumferential surface area is calculated as follows:

$$\text{Surface Area (mm}^2) = \pi \times \text{Canal Diameter (mm)} \times \text{Canal Length (mm)} \quad \text{Surface Area} \approx 3.1416 \times 0.25 \text{ mm} \times 30 \text{ mm} \approx 23.6 \text{ mm}^2$$

If the target density is 4,000 cells per square millimeter, the total endothelial cells required for the segment would be:

$$\text{Total Cell Count} = 4,000 \text{ cells/mm}^2 \times 23.6 \text{ mm}^2 = 94,400 \text{ cells}$$

This calculated cell number can then be translated into the required hydrogel volume for injection or into the parameters for hydrogel coating thickness, ensuring that the desired cell density is achieved without exceeding the anatomical constraints of Schlemm's canal 104.

Throughout the manufacturing and surgical processes, rigorous quality control measures are applied to confirm that the cell density meets specifications. Automated cell counting systems verify the number of cells per microliter in suspensions, while viability assays, such as live/dead staining, ensure that a high percentage of cells remain viable at the point of delivery. Imaging techniques like confocal microscopy are used to examine the evenness of cell distribution within hydrogel matrices, confirming that no regions are overloaded or depleted.

These careful techniques—ranging from precise suspension preparation and volumetric calculations to uniform mixing and intraoperative adaptability—are essential to achieving reproducible, safe, and effective endothelial cell densities. By adhering to these principles, the techniques described herein enables the controlled regeneration of Schlemm's canal 104 endothelium.

7.10 Viability and Aggregation Issues in Endothelial Cell Delivery to Schlemm's Canal While precise control over cell density and hydrogel volumes is crucial for successful regenerative canaloplasty, equally important are the biological challenges that influence the viability, uniform distribution, and functional integration of endothelial cells delivered into Schlemm's canal 104.

A key factor affecting viability is the sensitivity of endothelial cells to shear stress. During manufacturing, handling, or surgical injection, high shear forces can physically damage cell membranes, leading to apoptosis or necrosis. To mitigate these risks, manufacturers employ gentle mixing techniques, controlled flow rates, and specially designed dual-barrel syringes that enable cells to be blended with hydrogel components immediately prior to injection.

This minimizes mechanical trauma and limits the cells' exposure to any reactive crosslinkers used during hydrogel polymerization.

Another significant consideration for cell survival is nutrient availability within the hydrogel matrix. Dense cellular environments can restrict the diffusion of oxygen and metabolic substrates, creating localized regions of hypoxia. This issue becomes more pronounced at higher cell densities, where the diffusion distances increase and metabolic demand is elevated. For these reasons, moderate cell densities, often between 1,000 and 4,000 cells per square millimeter in coatings and up to approximately 5,000 cells per square millimeter in sleeves, are generally favored. These densities strike a balance between delivering a therapeutically effective dose and maintaining sufficient nutrient diffusion to preserve cell viability.

The chemistry of the hydrogel itself also plays a pivotal role in ensuring cell health. Certain hydrogel formulations undergo exothermic reactions during polymerization or release chemical crosslinking agents that can be cytotoxic if not carefully managed. Therefore, hydrogel chemistries are selected not only for mechanical performance and biocompatibility but also for mild crosslinking conditions and rapid neutralization processes, which collectively help protect the delicate endothelial cells during and after encapsulation.

Equally important to the success of endothelial regeneration is the prevention of cell aggregation. Even when delivered at overall safe densities, endothelial cells tend to adhere to each other, forming clusters or clumps rather than remaining evenly dispersed. Such aggregation poses several significant risks within the narrow confines of Schlemm's canal 104. Large cell clusters can physically obstruct aqueous humor outflow, thereby elevating intraocular pressure and compromising canal function. Additionally, localized aggregates may create areas of partial stenosis, leading to uneven fluid dynamics and increased shear stress in adjacent canal segments. Beyond mechanical concerns, aggregation can hinder nutrient diffusion, causing cell death within the core of cell clusters and provoking inflammatory responses that undermine the regenerative goals of the procedure.

Mathematical modeling can help predict the likelihood of cell aggregation within hydrogel matrices. When endothelial cells are randomly distributed into small microdomains of the hydrogel, the probability of finding multiple cells in a single microdomain can be described by Poisson distribution principles. Let $\lambda$ (lambda) denote the expected number of cells in a microdomain, calculated as the cell concentration multiplied by the microdomain volume. The probability P(K) of encountering exactly kkk cells in one microdomain is determined by the formula:

$$P(k) = \frac{\lambda^k \times e^{-\lambda}}{k!}$$

As an illustrative example, suppose a hydrogel is loaded with a cell concentration of 4,000 cells per microliter and the microdomain volume is defined as 0.1 microliter. In this case, $\lambda$ equals 400 cells per microdomain. This large $\lambda$ value suggests a high probability that nearly every microdomain will contain multiple cells, significantly increasing the risk of cell clustering and aggregation. Therefore, lower cell concentrations are often preferred to reduce $\lambda$, thereby decreasing the likelihood of cell aggregates forming during or after hydrogel solidification.

Engineering and procedural solutions have been developed to mitigate these viability and aggregation challenges. One approach is to lower the overall cell concentration in the hydrogel suspension, which diminishes the probability of cell-to-cell contact and subsequent clumping. Rapid polymerization of the hydrogel matrix is another valuable strategy, as it immobilizes cells quickly and prevents them from migrating into clusters before the gel fully sets. In some formulations, small amounts of anti-adhesive agents such as dextran sulfate are introduced to reduce cellular adhesion without compromising cell viability.

Surgical technique also plays an important role in preventing localized cell accumulation. Instead of injecting large volumes of hydrogel into a single canal segment, surgeons may distribute injections in smaller aliquots along the canal's circumference. This strategy promotes a more even spatial distribution of cells, thereby lowering the chance of forming localized high-density regions that could impede fluid outflow. Postoperative monitoring using high-resolution imaging technologies such as optical coherence tomography (OCT) and OCT angiography (OCTA) provides additional safeguards. These imaging modalities can reveal abnormal reflectivity patterns or localized narrowing within Schlemm's canal 104, which may indicate the presence of cell aggregates. Early detection enables prompt clinical intervention to preserve canal function.

Ultimately, the goal of regenerative canaloplasty is not merely to deliver an adequate quantity of endothelial cells, but to ensure that these cells remain viable, evenly distributed, and capable of forming a functional monolayer along the canal's interior surface. Thorough consideration of both aggregation and viability issues, in conjunction with careful volumetric and dosing calculations, provides the scientific and engineering basis for the safe and effective deployment of endothelial cell therapies. The combined mechanical and biological precision described herein ensures that the techniques can restore both the structural and physiological function of Schlemm's canal 104, supporting lower intraocular pressure and long-term ocular health.

7.11 Time to Achieve Endothelial Cell Adhesion in Schlemm's Canal

Although the canaloplasty procedure typically requires only a short intraoperative time of approximately 15 to 30 minutes, effective endothelial cell delivery remains feasible. Endothelial cells possess inherent adhesive properties that allow rapid attachment to extracellular matrix components within Schlemm's canal 104. Moreover, the hydrogel matrix disclosed herein serves as a temporary cell reservoir, enabling continued cell release and transfer to the canal wall even after conduit removal. Accordingly, this document contemplates both immediate cell adherence during surgical manipulation and sustained delivery postoperatively, ensuring sufficient cell deposition to support endothelial regeneration.

In other embodiments, the hydrogel coating 602 may form in situ during the surgical procedure, wherein liquid hydrogel precursors are applied to the conduit surface and undergo polymerization or gelation within Schlemm's canal 104. This approach allows for a conformable and patient-specific coating that adapts to anatomical variations. Both pre-formed and in situ-formed hydrogel coating 602 fall within the scope of the present in In Situ-Forming Hydrogel Coating.

7.12 Comparison of Hydrogel Embodiments in Schlemm's Canal

TABLE 21

Comparison of Pre-Formed Hydrogel vs. In Situ Hydrogel for
Microcatheter Coating in Schlemm's Canal

| Feature | Pre-Formed Hydrogel Coating | In Situ Hydrogel Coating |
|---|---|---|
| Bare Conduit Diameter | 200 micrometers (µm) | 200 micrometers (µm) |
| Hydrogel Thickness Added | Adds 15 µm per side, resulting in a total outer diameter of 230 µm | Hydrogel is injected into the canal, filling gaps around the conduit; thickness varies depending on anatomy and injection volume. |
| Resulting Conduit Diameter | Precisely measured and controlled at 230 µm | May remain effectively at ~200 µm if hydrogel does not significantly accumulate around the conduit shaft. |
| Manufacturing Method | Applied and crosslinked ex vivo during manufacturing; results in a ready-to-use device. | Formed intraoperatively by injecting liquid hydrogel precursor, which gels in situ around the conduit. |
| Thickness Control | Precisely controlled during manufacturing for consistent device geometry. | Variable; surgeon can adjust volume and injection rate to tailor hydrogel deposition. |
| Adaptability | Fixed geometry; limited intraoperative customization. | Highly adaptable to patient-specific canal size, shape, or pathology (e.g., fibrosis). |
| Storage and Logistics | Requires sterile packaging and moisture control to prevent dehydration of hydrogel | Minimal preoperative storage needs; precursor solutions often stored as liquids and mixed intraoperatively. |
| Cell Loading Possibility | Can be preloaded with endothelial cells or therapeutic agents during manufacturing. | Endothelial cells can be mixed into hydrogel precursor immediately before injection. |
| Surgical Workflow Impact | Simplifies surgical workflow; no mixing required during procedure. | Requires additional intraoperative steps, but allows real-time adjustments for anatomy. |
| Advantages | Predictable dimensions, manufacturing quality, and cell dose consistency. | Superior anatomical conformity and tailored treatment for varied canal anatomies. |
| Challenges | Potential dehydration or mechanical fragility during shipping and handling. | Demands precise surgical technique and fast polymerization kinetics to avoid premature gelation. |

Table 21 compares pre-formed hydrogel coatings and in situ-forming hydrogel coatings for microcatheter use in Schlemm's canal 104, detailing catheter 202 dimensions, manufacturing methods, and key surgical considerations relevant to endothelial cell delivery and procedural safety.

The embodiments shown in Table 21 illustrate two distinct methods for integrating hydrogel technologies with conduits that include microcatheters designed for canaloplasty and endothelial cell delivery into Schlemm's canal 104.

In pre-formed hydrogel systems, a hydrogel layer approximately fifteen micrometers thick is applied to the conduit's surface during manufacturing. This controlled process ensures a consistent coating thickness and results in a final conduit diameter of about two hundred thirty microm-eters. Such precision allows manufacturers to pre-load thera-peutic agents, including endothelial cells 208 or growth factors, directly into the hydrogel ex vivo, creating a ready-to-use device that simplifies surgical workflows and ensures uniform therapeutic dosing.

Conversely, in situ hydrogel systems involve injecting a liquid hydrogel precursor into Schlemm's canal 104 while the conduit is in place. This precursor subsequently gels around the conduit surface, maintaining the conduit's base diameter at roughly two hundred micrometers while con-forming precisely to the patient's individual canal anatomy. The in situ approach offers significant intraoperative flex-ibility, allowing surgeons to accommodate variable canal diameters, curvatures, or localized pathological changes such as fibrosis. However, it demands meticulous surgical timing and rapid polymerization kinetics to avoid premature gelation or incomplete hydrogel formation.

Both methods enable localized delivery of endothelial cells 208. In pre-formed systems, cells may be integrated into the hydrogel during manufacturing, while in situ sys-tems permit immediate preoperative mixing of cells into the hydrogel precursor for customized delivery. Each technique, therefore, contributes to the regenerative potential of Schlemm's canal 104 procedures, ensuring that conduit dimensions remain safely compatible with the canal's lumen, which averages between one hundred ninety micrometers and three hundred seventy micrometers in diameter.

Together, these embodiments support robust enablement for clinical applications across diverse patient anatomies and surgical contexts, advancing the therapeutic integration of microcatheter technology and regenerative cell therapies.

7.13 In Vivo and Ex Vivo Approaches for Endothelial Cell Delivery

This document contemplates both in vivo and ex vivo strategies for endothelial cell delivery. In the in vivo method, cells are delivered directly into Schlemm's canal 104 during canaloplasty, leveraging the hydrogel as a carrier for rapid tissue contact and subsequent slow release. Although the surgical time is brief, the hydrogel's persistence within the canal allows for continued cell delivery after conduit removal.

In ex vivo strategies, such as pre-coating a stent or other implant with endothelial cells 208, cells can be seeded and allowed to adhere for hours in controlled laboratory condi-tions prior to implantation. In such scenarios, time con-straints imposed by surgical duration are effectively elimi-nated, offering another robust pathway for ensuring high-quality cell attachment and viability.

7.14 Rapid Endothelial Cell Seeding

During Descemet's Stripping Automated Endothelial Keratoplasty ("DSAEK"), corneal endothelial cells begin adhering to the host corneal tissue within minutes to hours, achieving secure attachment typically within 24 to 48 hours. Similarly, the endothelial cells 208 delivered via hydrogel matrices can establish initial tissue contact rapidly, with sustained hydrogel presence facilitating further cell integra-tion postoperatively. Effective endothelial therapy occurs within the brief duration of canaloplasty procedures.

Endothelial cell seeding onto polymer scaffolds achieves greater than 50% cell adherence within just 10 to 15 min-utes, highlighting how quickly these cells can establish meaningful attachment to biomaterial surfaces.

The disclosed hydrogel-based systems leverage both the biological properties of endothelial cells and advanced mate-rial science innovations to ensure effective cell delivery even within the short surgical duration of canaloplasty proce-dures. The document contemplates that endothelial cells can adhere rapidly to the canal wall during the procedure and continue to integrate afterward through sustained release from the hydrogel matrix.

7.15 Clinical Embodiments of Endothelial Cell Delivery in Schlemm's Canal

While glaucoma represents the primary target for regen-erative therapies in Schlemm's canal 104, the structural and functional principles underpinning endothelial cell delivery extend to a variety of other ocular disorders. The present document contemplates applications beyond glaucoma, addressing multiple conditions where endothelial cell loss, dysfunction, or structural abnormalities contribute to com-promised aqueous humor dynamics or canal integrity.

Post-Surgical Trauma or Scarring. Surgical interventions such as canaloplasty, trabeculectomy, or minimally invasive glaucoma surgeries (MIGS) can inadvertently damage the delicate endothelium lining Schlemm's canal 104. Scarring and fibrosis may subsequently reduce canal lumen patency, elevate outflow resistance, and predispose patients to per-sistent or recurrent intraocular pressure (IOP) elevation. Endothelial cell delivery via hydrogel coatings, sleeves, or injectable suspensions provides a means of repopulating denuded canal surfaces, promoting regeneration of the native endothelial layer, and reducing fibrotic remodeling. Such therapy could prove particularly valuable in revision surgeries where preserving residual canal function is critical.

Primary or Secondary Ocular Hypertension. Not all cases of elevated IOP fulfill the criteria for glaucoma diagnosis, as optic nerve damage and/or visual field changes may be absent. In patients with ocular hypertension-whether pri-mary or secondary-early intervention to preserve or restore canal endothelial health may prevent progression to glau-comatous damage. Hydrogel-based endothelial cell delivery offers a strategy for normalizing canal outflow resistance in these pre-glaucomatous states, potentially avoiding or delay-ing the need for more invasive surgical treatments.

Steroid-Induced Ocular Hypertension. Steroid therapy, commonly employed in managing uveitis or post-operative inflammation, is a well-documented cause of elevated IOP. This phenomenon is partly mediated by steroid-induced dysfunction of trabecular meshwork 106 and Schlemm's canal 104 endothelial cells, resulting in reduced aqueous humor outflow. Incorporating endothelial cell therapy into surgical interventions for steroid responders offers a regen-erative approach aimed at reversing steroid-induced endothelial changes, thus restoring normal canal physiology.

Congenital and Developmental Anomalies. Certain con-genital conditions feature underdeveloped or hypoplastic Schlemm's canal 104 structures, impairing aqueous outflow and leading to early-onset ocular hypertension. In pediatric or adolescent patients, traditional surgical options may be limited by anatomical variability and long-term scarring risk. Hydrogel-mediated endothelial cell delivery provides a method for introducing functional endothelial layers into a deficient canal architecture, potentially facilitating more physiological outflow mechanisms and delaying disease progression.

Post-Inflammatory Canal Damage. Inflammatory conditions such as anterior uveitis can damage canal endothelium through direct inflammatory insult or subsequent fibrotic remodeling. Loss of endothelial cells disrupts the semi-permeable barrier and regulatory functions essential for maintaining physiological outflow resistance. The system enables precise delivery of endothelial cells into the inflamed or post-inflammatory canal environment, aiding tissue repair and reducing the risk of chronic outflow obstruction.

Surgical or Traumatic Canal Wall Injury. Intraocular surgical maneuvers, including those involving microcatheters or viscodilation balloons, as well as ocular trauma, can mechanically disrupt Schlemm's canal 104 walls. These injuries may result in localized endothelial cell loss, focal stenosis, or scarring that elevates outflow resistance. Hydrogel coatings or sleeves carrying endothelial cells 208 can be employed intraoperatively to cover these defects, promoting organized tissue healing and reducing fibrotic closure of the canal lumen.

Idiopathic or Age-Related Endothelial Decline. Emerging evidence suggests that Schlemm's canal 104 endothelium undergoes age-related decline in cell density and function, contributing to higher IOP and increased glaucoma risk in older populations. Even in patients without clinically manifest glaucoma, early replacement of declining endothelial cells could maintain canal permeability, thus preserving normal intraocular pressure regulation. The disclosed hydrogel technologies can be adapted for such prophylactic or early-intervention scenarios.

Collector Channel and Adjacent Tissue Repair. The therapeutic potential of endothelial cell delivery extends beyond the canal lumen itself. Many pathologies affecting aqueous outflow originate at or near the collector channel ostia and the juxtacanalicular trabecular meshwork 106. Endothelial cell therapy delivered through hydrogel systems can contribute to tissue regeneration in these transition zones, enhancing the overall outflow network's functionality.

Enablement Considerations

This document contemplates delivery of endothelial cells through multiple configurations, including hydrogel coatings, hydrogel sleeves, and injectable in situ-forming hydrogels, tailored to the canal's geometry and pathology. Each of these modalities offers distinct advantages: hydrogel coatings 602 allow thin, uniform delivery directly from a conduit or conduit, minimizing lumen compromise; hydrogel sleeves 204 provide greater volumetric capacity and may act as temporary or biodegradable scaffolds; and injectable hydrogels offer flexibility in adjusting cell volume and density to patient-specific anatomy.

Moreover, the mathematical relationships detailed in earlier sections, linking canal surface area, hydrogel volume, and target cell densities, equip surgeons and manufacturers with precise frameworks to ensure safe and effective application across a spectrum of conditions.

By enabling controlled delivery of viable endothelial cells under strict dimensional and physiological constraints, this document provides a robust platform adaptable to both glaucomatous and non-glaucomatous pathologies. The diverse clinical indications reinforce the broad utility and enablement of the hydrogel-based endothelial cell delivery systems described herein.

7.16 Controlling Endothelial Cell Density During Regenerative Surgery

In certain embodiments, surgeons may prepare hydrogel coatings 602 or hydrogel sleeves 204 intraoperatively, enabling tailored endothelial cell delivery for each patient's unique anatomy. Whether the hydrogel is applied directly as a thin coating on the microcatheter or molded as a separate tubular sleeve, several practical techniques allow the surgical team to carefully control endothelial cell density.

Preparing a Defined Cell Suspension

The process begins with the surgeon preparing a precise suspension of endothelial cells in a measured volume of hydrogel precursor solution. The desired cell density is calculated based on a predetermined therapeutic target, often ranging from approximately 2,500 to 3,500 cells per square millimeter of Schlemm's canal 104 surface.

For example, to achieve a density of 3,000 cells/mm² over a full 3600 treatment of Schlemm's canal 104 (with an estimated canal surface area of ~30 mm²), the surgeon would mix approximately 90,000 endothelial cells into the hydrogel matrix destined for the coating or sleeve.

Volumetric Control

Volumetric control is necessary to maintain accurate dosing. Surgeons employ micropipettes or calibrated syringes to measure both the hydrogel precursor volume and the endothelial cell suspension precisely. This volumetric accuracy ensures a consistent cell-to-hydrogel ratio, preventing variability in cell density from one procedure to the next.

Mixing Techniques

During preparation, the cell suspension and hydrogel precursor must be combined gently to avoid introducing air bubbles or generating excessive shear stress that could damage delicate endothelial cells. In some instances, surgical systems may include dual-barrel syringes designed to simultaneously mix and dispense the hydrogel-cell blend directly onto the conduit or into a mold for sleeve formation.

Coating Thickness Control

Control of hydrogel thickness is another crucial factor influencing endothelial cell density. For conduit coatings, surgeons can vary the number of dips, speed of withdrawal, or duration of immersion to achieve the desired hydrogel layer thickness. In the case of hydrogel sleeves 204, the surgeon molds the hydrogel to the intended wall thickness and length. Thicker hydrogel layers inherently accommodate higher cell loads per unit length, thus allowing the surgeon to fine-tune cell density based on anatomical requirements.

Surgeon Calibration Charts

Manufacturers may support surgeons by providing pre-calculated calibration charts that correlate hydrogel volumes with specific cell loading and predicted cell densities. These tools enable highly accurate dosing even for surgical teams without specialized laboratory experience, ensuring consistent clinical outcomes across varied operating environments.

Intraoperative Dosing Example: Controlled Cell Delivery Over 180° canal Segment

In a typical intraoperative scenario, the surgeon may elect to perform a 180° canal-based treatment, which corresponds to approximately 15 mm of Schlemm's canal 104 length. Based on the canal's anatomical parameters, particularly its diameter, this semi-circumferential region encompasses a total internal surface area of approximately 11.8 mm².

To achieve a therapeutic target density of 3,000 endothelial cells per $mm^2$, the total number of cells required can be calculated as:

$$11.8\ mm^2 \times 3{,}000\ cells/mm^2 = 35{,}400\ cells$$

This calculation allows the surgeon to tailor the cell dose precisely to the treated segment.

If the hydrogel precursor volume prepared for delivery is 10 microliters (L), the cell suspension should contain 35,400 cells in 10 μL, yielding a final concentration of 3,540 cells/L.

By pre-determining both the surface area of the treated canal segment and the desired cell density, the surgeon can achieve accurate dosing. This approach minimizes the risk of canal overloading and ensures effective, physiologically safe endothelial delivery. The ability to perform such precise, real-time calculations during surgery underscores the practical utility and customizability of the disclosed endothelial cell therapy system.

7.17 Role of Imaging in Verifying Hydrogel Conformity and Cellular Integration

In certain embodiments, the hydrogel sleeve 204 or hydrogel coating 602 is formulated to exhibit limited swelling upon exposure to aqueous humor, thereby ensuring secure placement without exerting excessive radial force on Schlemm's canal 104 walls.

Hydrogels are hydrophilic polymer networks capable of absorbing fluid and expanding, a phenomenon known as swelling. While a certain degree of swelling can be beneficial for device stability and biological performance, uncontrolled or excessive swelling carries risks that necessitate careful design and clinical monitoring.

Excessive hydrogel swelling could potentially compress the canal lumen, impair aqueous outflow, and stress endothelial cells. Accordingly, this document contemplates the use of hydrogel materials with controlled crosslinking density, limited volumetric expansion, and tailored mechanical properties to balance effective endothelial cell delivery with the preservation of Schlemm's canal 104 patency and function.

Postoperative monitoring through high-resolution OCT and OCTA is essential not only for assessing cell survival and flow dynamics, but also for confirming that hydrogel swelling remains within acceptable anatomic limits. Hyper-reflective zones may indicate excessive accumulation or cellular debris, while canal narrowing can signal over-expansion. These signals, especially when interpreted through AI-enabled algorithms, assist clinicians in determining whether further intervention, dosing adjustment, or second-stage therapy is warranted. This imaging-guided oversight reinforces the safety and precision of the disclosed regenerative platform.

Mechanisms and Variables Influencing Hydrogel Swelling

The extent of hydrogel swelling is determined by multiple physicochemical factors, including the chemical composition of the hydrogel matrix, such as hyaluronic acid, polyethylene glycol, or alginate, each possessing distinct water absorption capacities and mechanical properties. The crosslinking density of the polymer network, which governs the mesh size and, consequently, the degree to which water molecules can infiltrate and expand the hydrogel structure, also impacts the hydrogel swelling. Hydrogel swelling is impacted by the ionic composition of the surrounding aqueous humor, where variations in osmolarity and ion concentration can significantly alter swelling kinetics. The hydration state of the hydrogel at the time of implantation impacts swelling, as partially dehydrated hydrogels may undergo more pronounced swelling upon exposure to the intraocular environment.

Potential Therapeutic Benefits of Controlled Swelling

When properly controlled, hydrogel swelling offers multiple therapeutic advantages: it can facilitate secure placement of the hydrogel within Schlemm's canal 104 via gentle radial expansion, effectively anchoring the coating or sleeve against the canal walls without the need for mechanical fixation; swelling increases the contact surface area between the hydrogel and the canal endothelium, enhancing opportunities for endothelial cell transfer and integration into native tissue; and a moderately swollen hydrogel may exert a mechanical tamponade effect on microvascular bleeding sites, potentially reducing intraoperative hemorrhage and maintaining a clearer surgical field.

Risks Associated with Excessive Hydrogel Swelling

Conversely, uncontrolled swelling can introduce significant risks, including compression of Schlemm's canal 104 lumen, which may impede the normal outflow of aqueous humor and precipitate a postoperative increase in intraocular pressure (IOP); mechanical stress applied to the canal walls, which could compromise the very endothelial cells the therapy seeks to regenerate; obstruction of collector channels, thereby impairing fluid drainage into the episcleral venous system and exacerbating glaucoma pathology; and ischemic stress on delicate canal tissues if radial forces exceed physiological tolerance, potentially leading to endothelial cell damage or local fibrosis.

For example, a hydrogel that swells by 30% radially transforms a 200 μm bare conduit into a device approximately 260 μm in diameter-still within the typical diameter range of Schlemm's canal 104. However, a hydrogel that swells by 100% would expand the same conduit to 400 μm, exceeding the canal's anatomical limits and risking complete occlusion.

Engineering Strategies to Mitigate Swelling Risks

This document, therefore, contemplates several engineering strategies to maintain hydrogel swelling within safe and therapeutic bounds, such as employing low-swelling hydrogel formulations designed for limited volumetric expansion (e.g., <10-20% increase), precisely controlling crosslinking density to balance flexibility, mechanical stability, and minimal expansion, designing hydrogel coatings and sleeves with thickness constraints (e.g., ≤30 μm for coatings) to ensure that the overall diameter of the conduit or sleeve remains comfortably within the anatomical confines of Schlemm's canal 104, and utilizing stimuli-responsive hydrogels that modulate their swelling behavior in response to environmental triggers such as ionic strength, pH, or temperature, allowing the hydrogel to remain stable under physiological conditions while avoiding sudden or excessive expansion.

Clinical Recognition and Management of Excessive Swelling

From a clinical perspective, recognizing signs of excessive hydrogel swelling is crucial to maintaining patient safety and ensuring therapeutic efficacy. Surgeons and postoperative clinicians may suspect excessive swelling if they observe unexpected elevation of intraocular pressure in the immediate postoperative period, reduced or absent aqueous outflow observed during gonioscopic examination, symptoms of ocular discomfort or pain, suggesting mechanical distension of Schlemm's canal 104, and gonioscopic signs of canal distortion, narrowing, or apparent blockage.

Management may include observation in mild cases where swelling may subside as the hydrogel equilibrates, and administration of topical or systemic IOP-lowering agents to mitigate pressure spikes.

7.18 Methods to Prevent Mechanical Loss of Endothelial Cells

The method contemplates various techniques to minimize mechanical loss of endothelial cells during passage through Schlemm's canal 104, such as the encapsulation of cells in robust hydrogel matrices, thermo-responsive gels that remain firm during manipulation and soften at body temperature, enzyme-sensitive hydrogels that release cells only upon exposure to specific proteases (e.g., MMP-2), controlled dwell times in specific canal segments, and surface micro-texturing of conduits to shelter cells during navigation.

These methods ensure cell survival and uniform deposition, reducing losses due to mechanical shear.

7.19 Feasibility of Effective Endothelial Cell Delivery During Short Surgical Procedures A frequent consideration in minimally invasive ophthalmic surgery is whether the relatively brief duration of canaloplasty procedures, typically ranging from 15 to 30 minutes, permits meaningful biological engagement, particularly when the therapeutic strategy involves the transfer or implantation of living cells. The concern is especially relevant when endothelial cells are to be seeded into Schlemm's canal 104/, as successful therapy hinges on the viability, adherence, and potential integration of these cells within a narrow anatomic space and compressed timeframe.

The present document addresses this challenge by integrating both biological insights and materials science solutions that support rapid and effective endothelial cell transfer during the course of a standard surgical procedure.

7.20 Biological Basis for Rapid Adherence and Integration

Endothelial cells possess intrinsic adhesive capabilities that enable them to attach quickly to the surrounding tissue. These cells express a variety of integrins and adhesion molecules, such as vascular endothelial (VE)-cadherin and platelet endothelial cell adhesion molecule-1 (PECAM-1), which rapidly bind to extracellular matrix (ECM) components, including collagen and laminin, both of which are abundant in the walls of Schlemm's canal 104.

Experimental observations in both vascular and ophthalmic tissue engineering demonstrate that initial cell attachment can occur within minutes. Although full cellular spreading and formation of mature cell junctions require longer periods—often several hours—the early binding of cells is often sufficient to "seed" the tissue surface effectively. Studies have shown that even 5-10 minutes of contact time can result in significant cell attachment, highlighting the practicality of achieving endothelial cell transfer during routine canaloplasty durations.

Numerous studies in vascular and corneal tissue engineering have demonstrated that endothelial cells can initiate adhesion to compatible substrates within minutes of exposure, especially when conditions support integrin-mediated binding. Human Schlemm's canal endothelial cells, which share many properties with vascular and lymphatic endothelial cells, are known to express adhesion molecules such as CD31, VE-cadherin, and integrins (e.g., $\alpha V \beta 3$, $\alpha 5 \beta 1$) that facilitate rapid interaction with extracellular matrix proteins like fibronectin, laminin, and collagen type IV. When introduced into a compatible microenvironment, these cells can begin anchoring to a substrate within 5-10 minutes, initiating signaling cascades that support survival, morphology retention, and junctional integrity.

Furthermore, canaloplasty offers a nearly ideal surgical environment for such interaction: Schlemm's canal 104 provides a confined luminal space that promotes surface-to-surface contact, stabilizes cellular positioning, and limits convective washout. This facilitates localized deposition and protects cells during the early phase of contact and attachment.

7.21 Hydrogel Engineering for Short-Duration Efficacy

The system further enhances feasibility through the use of engineered hydrogel sleeves 204 or hydrogel coatings 602 that are preloaded with endothelial cells 208 in a hydrated, bioactive matrix. These hydrogels are specifically formulated to maintain cell viability in situ, provide substrate-bound cues for adhesion, and release bioactive molecules that promote local integration. For example, polyethylene glycol (PEG)-based hydrogels can be functionalized with RGD peptides or other cell-adhesive ligands to improve initial cell attachment within the canal lumen. Additionally, the hydrogel's porosity and hydration state support nutrient diffusion and oxygenation, necessary for short-term viability and long-term engraftment.

Certain hydrogel formulations are designed to degrade or soften within 5 to 15 minutes, matching the surgical workflow and allowing for a controlled, sustained release of cells into the canal. Thermoresponsive or enzyme-responsive formulations allow the hydrogel to soften or dissolve once placed in the intraocular environment, ensuring that the cells are gently deposited and not retained in a compacted matrix that would limit their interaction with the native tissue.

Surgical Workflow Integration

From a surgical standpoint, the method of delivery also supports efficient cell transfer. As the conduit is advanced circumferentially through Schlemm's canal 104, cells embedded in or on the hydrogel sleeve 204 are deposited directly along the inner wall of the canal. This continuous deposition method ensures even cell distribution and circumferential coverage without requiring prolonged dwell times or multiple passes. Furthermore, the design minimizes cell loss by preventing reflux into the anterior chamber or collector channels.

Feasibility Demonstrated in Analogous Systems

The concept of cell delivery during short-duration procedures is well established in other domains, such as corneal endothelial cell injection for Fuchs' dystrophy and endothelial seeding of vascular grafts, where meaningful cell adhesion and viability can be achieved with exposure times of 10 minutes or less. These precedents reinforce the scientific validity of rapid endothelial delivery in Schlemm's canal 104.

The present document demonstrates that endothelial cell delivery into Schlemm's canal 104 is not only feasible within a short surgical timeframe but is in fact well-suited to the procedural flow and anatomy of canaloplasty. Through the use of cell-compatible hydrogel substrates, biofunctional additives, and efficient conduit-mediated deployment, the system promotes immediate cell-to-tissue interaction and sets the stage for long-term integration-all within the duration of a standard 15-30 minute ophthalmic surgery.

8.0 PREPARATION, CARE, AND STORAGE OF ENDOTHELIAL CELLS

The longevity of pre-formed hydrogel coatings 602 and hydrogel sleeves 204 seeded with endothelial cells 208 depends both on the hydrogel's physical stability and on the viability of the encapsulated cells during storage. Cryopreservation techniques may enable shelf lives of 12 to 24 months while maintaining endothelial cell viability, whereas hypothermic storage at 4° C. may preserve cells for up to 7 to 14 days. Alternatively, hydrogel-coated devices may be manufactured without preloaded cells, allowing endothelial cells 208 to be seeded immediately prior to surgical use. In all cases, this document contemplates packaging methods and hydrogel formulations designed to preserve both mechanical integrity and biological functionality during storage and handling.

8.1 Longevity of Endothelial Cells in Pre-Formed Coatings

Endothelial cells are inherently delicate and prone to degradation under standard storage conditions. At room temperature or under mild refrigeration, cell viability tends to decline significantly over days or weeks due to nutrient depletion, accumulation of metabolic waste products, and apoptosis arising from detachment-induced stress within the hydrogel matrix.

8.2 Longevity of the Hydrogel Structure

Independent of cell viability, the hydrogel material itself possesses a finite shelf life, which is determined by factors such as hydrogel chemistry, crosslinking methods, and moisture control during storage. For example, polyethylene glycol (PEG)-based hydrogels can remain stable for approxisolutions designed to slow cellular metabolism, similar to methods employed in corneal preservation. However, hypothermic storage is typically feasible only for shorter supply chains due to the progressive decline in cell viability beyond two weeks.

By contrast, dry storage techniques such as lyophilization are unsuitable for live cell preservation within hydrogel matrices. While lyophilization is effective for stabilizing pharmaceutical agents, the process generally leads to cell death, rendering it impractical when live endothelial cells are required.

Given these considerations, some manufacturers may choose to produce hydrogel-coated devices without preloaded cells, instead leaving the hydrogel matrix empty and loading endothelial cells 208 immediately before surgery. Although this approach sidesteps long-term cell viability concerns, it introduces additional intraoperative steps and complexity for the surgical team.

8.3 Longevity of Coatings Versus Sleeves

TABLE 22

| | Longevity of Pre-Formed Hydrogel Coatings Seeded with Endothelial Cells | |
| --- | --- | --- |
| Aspect | Hydrogel Coating | Hydrogel Sleeve |
| Thickness | ~10-50 μm | ~100-300 μm wall thickness |
| Mechanical Risk | Higher shear/fracture risk | Lower risk due to elastic bulk |
| Storage Limits | Moisture-sensitive; thinner films dry out faster | More stable if kept hydrated |
| Shelf Life (Cryo) | ~12-24 months possible | ~12-24 months possible |
| Shelf Life (Cold) | ~7-14 days | ~7-14 days |
| Cell Viability | Same principles apply | Same principles apply | mately one to two years if kept hydrated under sterile conditions. Conversely, hyaluronic acid-based hydrogels tend to be more susceptible to hydrolytic degradation over several months if not properly stored.

Effective packaging is therefore essential to maintain hydrogel integrity. Sterile, moisture-retaining packaging such as blister packs or foil pouches is crucial to prevent desiccation, which can cause hydrogel cracking, shrinkage, or loss of mechanical properties.

The hydrogel itself can remain stable for up to one to two years under proper storage conditions, whereas viable endothelial cells 208 require either cryopreservation for long-term storage or hypothermic conditions for shorter-term storage. Clinical and logistical considerations will ultimately dictate whether manufacturers pursue a preloaded hydrogel device, offering convenience at higher manufacturing complexity, or an empty hydrogel sleeve 204 intended for intraoperative cell loading.

To preserve cell viability over longer periods, one effective strategy is cryopreservation, wherein the hydrogel-coated devices are frozen—typically in liquid nitrogen—using cryoprotective agents such as dimethyl sulfoxide (DMSO). Cryopreservation can extend the shelf life of endothelial cell-laden hydrogel coatings to 12 to 24 months, enabling global manufacturing and distribution logistics. However, cryopreservation introduces its own challenges, including the risk of cellular injury during freezing and thawing, as well as the need for precise rehydration and handling protocols to restore cell viability and function post-thaw.

Alternatively, hypothermic storage at approximately 4° C. can preserve cell viability for shorter periods, generally ranging from 7 to 14 days. This approach uses specialized The longevity of a pre-formed hydrogel coating 602 or hydrogel sleeve 204 seeded with endothelial cells 208 is governed by two interrelated factors: the viability of the encapsulated endothelial cells during storage and handling, and the physical stability of the hydrogel material itself over time. Both considerations are important to ensure that the device retains its therapeutic potential and functional integrity until the moment of surgical use.

8.4 Manufacturing Quality Control

Hydrogel coatings 602, hydrogel sleeves 204, and injectable hydrogels described in the present document are manufacturable using established processes that support precise dimensional control and cell integration.

For hydrogel-coated conduits, manufacturing involves controlled application techniques such as dipping or spraying, followed by verification of coating thickness using microscopy or optical measurements. Typical hydrogel layers are kept at or below 20 micrometers per side to ensure compatibility with Schlemm's canal 104 dimensions and introducer sheaths.

Hydrogel sleeves 204 are produced using molds or mandrels that define inner and outer diameters with tight tolerances. Wall thickness is typically maintained between 20 and 30 micrometers per side unless specific anatomical allowances justify thicker designs. Hydrogel sleeves 204 are inspected for uniformity, concentricity, and mechanical integrity, including swelling behavior in physiological solutions.

Endothelial cells 208 incorporated into hydrogels are prepared under sterile conditions, counted with automated systems, and tested for viability. Mixing methods are designed to distribute cells uniformly while minimizing shear stress. For injectable hydrogels, dual-barrel syringes may be used to keep cells and hydrogel precursors separate until the point of delivery, reducing exposure to reactive chemicals.

Quality control includes sterility testing, viscosity measurements, gelation time verification, and simulated deployment trials to confirm navigability and consistent hydrogel behavior. Imaging methods such as optical coherence tomography and microscopy are used to confirm coating uniformity and cell distribution.

Manufacturing processes apply statistical process controls and maintain complete traceability of materials and methods. These controls enable the reproducible production of hydrogel devices designed to deliver endothelial cells 208 into Schlemm's canal 104 safely and effectively, supporting both regulatory compliance and practical clinical use.

8.5 Preparation and Deployment of Hydrogel Sleeve

The present document contemplates embodiments wherein the hydrogel layer intended for delivering endothelial cells 208 into Schlemm's canal 104 is provided in the form of a hydrogel sleeve 204. This hydrogel sleeve 204 may be either preloaded and assembled by the manufacturer or prepared and applied by the surgeon immediately prior to surgery. Both manufacturing processes and intraoperative techniques fall within the scope of this document and are designed to provide flexibility for diverse clinical workflows and supply chain realities.

8.6 Packaging and Storage Requirements

Hydrogel sleeves 204, especially those seeded with endothelial cells 208, require careful packaging and storage, using sterile, moisture-retaining packaging to prevent drying and cracking. Cryopreserved sleeves require liquid nitrogen storage and controlled thawing protocols, and acellular sleeves may be stored refrigerated for up to 1-2 years, simplifying logistics for facilities without cryopreservation capabilities.

8.7 Hydrogel Sleeves Prepared by Manufacturer

In certain embodiments, hydrogel sleeves 204 are fabricated by the manufacturer as pre-formed, sterile tubular structures specifically engineered to encase the external surface of a microcatheter. These hydrogel sleeves 204 are designed to support uniform delivery of endothelial cells 208 or therapeutic agents into Schlemm's canal 104, while also serving as a protective, lubricating interface between the device and delicate ocular tissues.

The manufacturing process begins with the preparation of a hydrogel precursor solution. Commonly used polymers include polyethylene glycol diacrylate (PEGDA), thiolated hyaluronic acid, or other biocompatible macromers known for their mild gelation conditions and tunable properties. For applications involving cell delivery, autologous or cultured Schlemm's canal endothelial cells may be suspended directly into the precursor under sterile, temperature- and pH-controlled conditions, ensuring cell viability and distribution prior to gelation.

The precursor is then applied to a cylindrical mandrel, typically fabricated from Teflon or stainless steel, with dimensions closely matching or slightly exceeding the outer diameter of the target conduit. Techniques such as dip-coating, spray-deposition, or extrusion molding are employed to deposit the hydrogel around the mandrel. Multiple layers can be added sequentially to achieve a desired wall thickness, generally ranging from 100 to 300 micrometers, depending on anatomical and procedural requirements.

Crosslinking of the hydrogel is achieved via chemical, thermal, or photoinitiated reactions. Photocrosslinkable PEG-based hydrogels, for example, can be rapidly polymerized under controlled UV exposure using biocompatible photoinitiators such as Irgacure® or LAP (Lithium phenyl-2,4,6-trimethylbenzoylphosphinate). This curing process transforms the liquid precursor into a stable, elastic structure that retains mechanical integrity and cellular content.

Once cured, the tubular hydrogel sleeve 204 is carefully removed from the mandrel using sterile, low-friction handling techniques to preserve dimensional integrity. The sleeve is trimmed to the desired length, typically 5 cm, 10 cm, or 15 cm, based on the intended degree of canal coverage (e.g., 180-degree or 360-degree treatment).

For cell-loaded embodiments, post-manufacture viability testing is necessary. Trypan blue exclusion assays, metabolic activity assessments (e.g., MTT or resazurin), and microscopy-based uniformity checks ensure that the delivered cell population remains viable and homogeneously distributed throughout the sleeve matrix.

Finished hydrogel sleeves 204 are packaged in sterile, moisture-retentive pouches or blister packs. Acellular hydrogel sleeves can typically be stored under refrigeration (2-8° C.) for extended periods (up to 24 months), while cell-laden sleeves may require cryopreservation at −196° C. in liquid nitrogen vapor phase until thawed for immediate surgical use.

From a practical standpoint, manufacturer-prepared hydrogel sleeves 204 offer high uniformity, validated sterility, and reproducible performance. However, they may be associated with increased costs and logistical challenges, particularly for devices that contain live cells and require cryogenic shipping. In contrast, surgeon-prepared hydrogel sleeves 204 offer procedural flexibility and eliminate shipping constraints, but demand greater intraoperative precision and resources. Both manufacturing routes fall squarely within the scope and can be tailored to ensure safe, consistent cell dosing, avoiding complications such as canal lumen obstruction or cellular aggregation.

By accommodating both centralized and point-of-care fabrication models, the system enhances adaptability across diverse clinical settings and health systems, reinforcing its practicality and scalability in modern ophthalmic practice.

TABLE 23

Comparison of key characteristics between hydrogel coatings applied directly to the microcatheter shaft and separately manufactured hydrogel sleeves

| Aspect | Hydrogel Coating | Hydrogel Sleeve |
|---|---|---|
| Application Method | Dipped or sprayed onto conduit shaft | Formed separately, then slid over conduit |
| Thickness Control | Microns-level precision during coating | Thickness defined by mold dimensions |
| Length Control | Uniform along conduit length | Can be trimmed to custom lengths |

TABLE 23-continued

Comparison of key characteristics between hydrogel coatings applied
directly to the microcatheter shaft and separately manufactured hydrogel sleeves

| Aspect | Hydrogel Coating | Hydrogel Sleeve |
|---|---|---|
| Cell Loading Uniformity | Potential for minor variability along shaft | Typically more uniform due to molding |
| Handling Robustness | Fragile thin films | Generally sturdier due to thicker walls |

Table 23 shows a comparison of key characteristics between hydrogel coatings 602 applied directly to the microcatheter shaft and separately manufactured hydrogel sleeves 204. This table highlights differences in application methods, manufacturing controls, mechanical properties, and clinical flexibility, enabling clinicians and manufacturers to determine the optimal format for endothelial cell delivery based on surgical and logistical considerations.

8.8 Endothelial Cell Preparation, Coating, and Sleeve Manufacturing

In alternative embodiments, hydrogel coatings 602 and hydrogel sleeves 204 are manufactured in advance and preloaded with endothelial cells 208 under stringent Good Manufacturing Practice (GMP) conditions. This industrial-scale approach enables precise and reproducible control over endothelial cell density and distribution, contributing to product consistency, therapeutic efficacy, and regulatory compliance.

The process begins with the preparation of a defined endothelial cell suspension. Cultured Schlemm's canal endothelial cells are expanded in sterile, controlled environments using validated protocols. Only healthy, viable cells, typically confirmed via fluorescence-based viability staining and quantified using automated counters, are selected for inclusion. This ensures that each hydrogel construct contains a predictable and therapeutically relevant cell population.

Once a viable suspension is prepared, manufacturers employ precision liquid handling and dispensing systems capable of microliter-scale accuracy. These systems uniformly distribute the endothelial cells 208 throughout the hydrogel precursor matrix, minimizing the risk of clumping or regional cell overload that could otherwise lead to lumen obstruction.

Hydrogel coatings 602 are typically applied to conduit shafts via dipping, spraying, or rotational immersion in the cell-laden hydrogel mixture. These procedures are executed under tightly controlled environmental conditions, including temperature, humidity, and air cleanliness, to maintain sterility and reproducibility. Withdrawal speeds and post-application air jets are precisely modulated to remove excess hydrogel and achieve uniform coating thickness, often on the order of 100 to 300 micrometers.

Alternatively, hydrogel sleeves 204 are produced by extruding the hydrogel-cell composite into cylindrical molds or by dip-coating stainless-steel mandrels. The mold or mandrel dimensions are calibrated to match the target conduit geometry, and the hydrogel wall thickness and sleeve length can be adjusted to accommodate varying anatomical requirements or procedural goals. Manufacturers carefully titrate the number of suspended endothelial cells per microliter of hydrogel, ensuring that the entire sleeve remains within the desired therapeutic window for cell delivery.

After formation, both hydrogel coatings 602 and hydrogel sleeves 204 undergo rigorous quality control testing to verify the uniformity of cell distribution. High-resolution imaging techniques, such as confocal microscopy, fluorescent histology, or flow cytometry, are used to assess spatial cell localization and overall viability. Product specifications often define strict thresholds, such as requiring that each 10 mm segment of hydrogel-coated conduit contain 10,000±500 viable endothelial cells.

To ensure patient safety and regulatory compliance, each production batch is subject to comprehensive GMP quality assurance protocols. These include sterility testing, endotoxin assessments, and the issuance of Certificates of Analysis detailing the validated cell density, viability, and hydrogel integrity. In cell-loaded products, post-manufacturing viability rates are typically required to exceed 90%.

While both hydrogel coatings 602 and hydrogel sleeves 204 share foundational principles, such as precise cell suspension preparation, controlled hydrogel volume, and robust quality control, they differ in technical execution and clinical application. Hydrogel coatings 602 tend to be more streamlined for integration with catheterized devices, whereas hydrogel sleeves 204 offer greater modularity and customization options, including variable degradation profiles and delivery lengths. Both strategies are fully encompassed herein and serve to optimize the regenerative potential of endothelial therapies within Schlemm's canal 104.

8.9 Hydrogel-Based Conduit Embodiments for Schlemm's Canal Procedures

In addition to hydrogel sleeves 204 or hydrogel coatings 602 applied to conventional conduits, the present document also contemplates the fabrication of conduits constructed entirely or predominantly from hydrogel-based materials. These hydrogel-based conduits offer novel advantages in anatomical compatibility, drug delivery, and biodegradability for use in Schlemm's canal-based procedures, including canaloplasty, stent deployment, and viscodilation.

The hydrogel conduit may comprise a cross-linked polymer matrix, such as polyethylene glycol diacrylate (PEGDA), gelatin methacrylate (GelMA), polyvinyl alcohol (PVA), or hybrid composites reinforced with nanofibers or mesh to enhance mechanical strength. The internal lumen, typically ranging from 80 to 150 microns in diameter, is engineered to remain patent under physiologic intraocular pressure while permitting controlled delivery of therapeutic agents or viscoelastic substances. The overall external diameter may range from 200 to 300 microns, consistent with the anatomical dimensions of Schlemm's canal 104.

The hydrogel conduit may be fabricated with tunable swelling behavior, designed to expand minimally (e.g., <10%) upon exposure to aqueous humor, thereby preserving canal patency. It may further include embedded nanopores or aligned channels to facilitate controlled drug diffusion, as well as surface ridges or patterning to support endothelial guidance and adhesion.

To maintain conduit integrity during introduction, the hydrogel conduit may be preloaded into a surgical introducer or encased in a dissolvable sheath. In some embodiments, the hydrogel conduit may be engineered to degrade safely over time, leaving no permanent implant behind while enabling regenerative action during its therapeutic window.

Preclinical validation of such conduits may include assessments of burst pressure, navigation resistance in simulated Schlemm's canal 104, swelling kinetics, lumen integrity post-swelling, and drug elution profiles. The document thus enables a new class of bioactive, anatomically conforming, and potentially resorbable conduits for targeted therapy within Schlemm's canal 104.

TABLE 24

Comparative Features of Hydrogel-based vs. Nylon-based Catheters for Canaloplasty

| Feature | Hydrogel-based Catheter | Nylon-based Catheter |
| --- | --- | --- |
| Material Composition | Crosslinked hydrogel polymers (e.g. PEG-based, gelatin-methacrylate) | Nylon (polyamide) or polypropylene |
| Flexibility | Highly flexible, mimics tissue compliance | Semi-rigid, higher mechanical stiffness |
| Biocompatibility | Excellent, bioinert or bioactive formulations possible | Moderate, may provoke a limited foreign body response |
| Drug/Cell Delivery Capability | Can encapsulate and release drugs or release cells | None (requires separate delivery system) |
| Degradability | Tunable; resorbable hydrogels allow bioresorption | Non-degradable; must be withdrawn |
| Surface Customization | Nanostructures or biochemical moieties for cell interaction | Limited surface modification |
| Diameter Control | Slightly larger diameter due to swelling; tunable via crosslinking | Fixed mechanical diameter (e.g. 205 μm tip) |
| Integration with Imaging | Compatible with OCT/OCTA due to transparency and refractive index | Opaque; no inherent imaging benefits |
| Surgical Handling | May require modified introducer systems | Compatible with current introducer platforms |
| Manufacturing Complexity | Higher, requires sterilization of hydrated structures | Established industrial processes |
| Shelf Life | Shorter (especially if hydrated); may require refrigeration) | Long, dry storage under standard conditions |
| Use Case Scenario | Ideal for regenerative, cell-based canaloplasty or drug-eluting applications | Suited for mechanical dilatation and viscoelastic delivery only |

Table 24 compares hydrogel-based and nylon-based catheters 202 as used in Schlemm's canal 104 interventions, highlighting functional, material, and clinical aspects. The hydrogel-based embodiment may replace the traditional catheter 202 shaft or function as a coating or sleeve.

9.0 EMBODIMENTS OF HYDROGEL COATINGS AND SLEEVES

The present system is configured for integration with a broad range of devices employed in Schlemm's canal 104 interventions. These devices include, but are not limited to, flexible microcatheters, suture-based conduit systems, trabeculotomy and goniotomy instruments, viscodilation balloon devices, and intracanalicular implants or scaffolds. Hydrogel coatings 602, hydrogel sleeves 204, and injectable hydrogel formulations disclosed herein can be tailored to each device type to enable the delivery of a viable endothelial cells while maintaining the structural integrity and physiological function of Schlemm's canal 104.

Specific device categories such as viscodilation balloons necessitate unique engineering adaptations to withstand mechanical inflation forces, preserve lumen patency, and ensure controlled hydrogel deployment. Detailed embodiments and technical considerations for such adaptations, including dimensional constraints, hydrogel elasticity, and endothelial cell viability, are described in the sections that follow.

US 12,653,714 B1

81                                                                        82

TABLE 25

Generic Device Types for Schlemm's Canal Surgery and Compatibility
with Hydrogel-Based Regenerative Approaches

| Device Type | Procedure/Function | Potential Compatibility with Hydrogel Endothelial Delivery |
|---|---|---|
| Microcatheters for Canaloplasty | Circumferential viscodilation of Schlemm's canal; may traverse entire canal length (360 degrees). | Highly compatible with hydrogel coatings or sleeves; ideal for delivering endothelial cells along the canal wall. |
| Handheld Canaloplasty Instruments | Simplified versions of microcatheters with integrated viscoelastic delivery. | Good candidates for hydrogel coatings or sleeves; user-friendly formats may ease surgical deployment of hydrogel-based devices. |
| Combined Canaloplasty and Trabeculotomy Devices | Devices capable of both viscodilation and incisional trabeculotomy in a single procedure. | Excellent compatibility; hydrogel coatings or sleeves can be integrated into the canaloplasty portion of the procedure. |
| Viscodilation Devices (Generic) | Microcatheters or needles used solely for injection of viscoelastic materials into Schlemm's canal. | Suitable for hydrogel-coated surfaces or injectable hydrogel suspensions containing endothelial cells. |
| Intracanalicular Scaffolds or Stents | Implants placed partially or fully within Schlemm's canal to maintain patency or scaffold tissue. | although typically cover a shorter canal Potential candidates for hydrogel coatings that carry endothelial cells, length (e.g. 90-120 degrees). |
| Trabecular Microbypass Implants | Small implants bypassing the trabecular meshwork to facilitate aqueous outflow. | Generally less compatible due to smaller size, but thin hydrogel coatings may still be feasible for localized cell delivery. |
| Goniotomy and Trabeculotomy Blades | Blades or devices used to excise portions of the trabecular meshwork. | Limited direct compatibility; hydrogel delivery would be adjunctive rather than integrated into the device. |
| Electrocautery Ablation Tools | Devices removing trabecular tissue using electrical energy. | Less directly compatible; hydrogel materials might be used afterward as adjunctive therapy. |
| Suture-Based Canaloplasty Techniques | Use of sutures to tension Schlemm's canal and improve aqueous outflow. | Very compatible for hydrogel sleeves or coatings applied to microcatheters or sutures introduced into the canal. |
| Laser-Based Canaloplasty Systems | canaloplasty or modify canal Emerging technologies using laser energy to perform tissues. | Future potential for hydrogel adjuncts post-laser application; direct integration into devices less established. |
| Suprachoroidal Implants | Devices placed in the suprachoroidal space rather than directly in Schlemm's canal. | Generally less relevant for hydrogel-based canal endothelial delivery, unless used in combination therapies. |
| Biodegradable Canal Expanders | Implants designed to temporarily enlarge Schlemm's canal and then degrade over time. | Promising candidates for hydrogel coatings or inclusion of endothelial cells for regenerative purposes. |
| Hydrogel-Based Conduits or Scaffolds | Hydrogel structures engineered to replace or support canal tissue. | These devices inherently integrate hydrogel and cell delivery technologies. |
| Custom Drug or Cell-Delivery Conduits | Next-generation conduits engineered specifically for local drug or cell deployment. | Highly synergistic with hydrogel endothelial cell delivery strategies. |

Table 25 summarizes key categories of surgical devices used in Schlemm's canal 104 procedures, detailing their functions and evaluating their compatibility with hydrogel-based coatings, sleeves, or injectable systems for delivering endothelial cells 208. The information underlines the broad applicability of the present techniques across various surgical techniques and device designs.

9.1 Viscodilation Balloon Delivery

The present document contemplates the integration of endothelial cell therapy with viscodilation balloon devices as a novel strategy for regenerative intervention in Schlemm's canal 104. This embodiment broadens the disclosed endothelial platform technology, offering a transformative approach that combines mechanical and biological therapies within the same surgical procedure. Whereas conventional viscodilation balloons achieve purely mechanical enlargement of Schlemm's canal 104, this document introduces the additional dimension of cellular regeneration to repair and restore the canal's endothelial lining.

9.2 Background on Viscodilation Balloons in Schlemm's Canal

Viscodilation balloon devices are an established tool in minimally invasive glaucoma surgeries (MIGS). These devices are designed to navigate Schlemm's canal 104 circumferentially and achieve mechanical expansion by inflating a small-diameter balloon. During canaloplasty procedures, the balloon is typically filled with a viscoelastic material such as sodium hyaluronate, exerting radial pressure that gently dilates the canal, disrupts synechiae, and stretches the trabecular meshwork 106 and inner Schlemm's canal 104 wall. This mechanical action enhances the outflow of aqueous humor, aiming to lower intraocular pressure (IOP).

However, despite these benefits, viscodilation balloons inherently lack any biological capacity to regenerate or replace the delicate endothelial lining of Schlemm's canal 104. Indeed, balloon dilation may inadvertently cause microtrauma, further damaging or stripping away endothelial cells required to maintain physiological outflow resistance. This document recognizes this gap and seeks to transform viscodilation balloons into a regenerative platform capable of simultaneously achieving mechanical dilation and cellular therapy.

9.3 Rationale for Combining Balloons with Endothelial Cell Therapy

The concept of combining endothelial cell therapy with viscodilation balloons is rooted in both anatomical opportunity and surgical practicality. The act of balloon inflation exposes fresh extracellular matrix (ECM) surfaces along the inner canal wall, potentially providing an ideal substrate for endothelial cell adhesion. Freshly exposed collagen, laminin, and other matrix proteins facilitate integrin-mediated binding, creating favorable conditions for endothelial cell seeding.

Moreover, endothelial cell loss or dysfunction has been increasingly implicated in the pathophysiology of glaucoma, contributing to impaired aqueous humor regulation and elevated IOP. Replenishing the endothelial cell population during the same surgical session as canaloplasty offers a unique therapeutic synergy, mechanical dilation restores anatomical patency, while biological cell delivery restores physiological function.

Thus, integrating endothelial cell therapy with balloon technology holds the promise of transforming a purely structural procedure into one with true regenerative capacity, directly addressing the underlying cellular deficit in glaucoma.

9.4 Preparation and Modification of Viscodilation Balloons for Endothelial Cell Delivery The present document envisions a significant advancement in minimally invasive glaucoma surgery by integrating endothelial cell therapy with viscodilation balloon devices. This approach is intended to elevate canaloplasty from a purely mechanical intervention to a regenerative therapy that not only enlarges Schlemm's canal 104 structurally but also restores its biological functionality through the targeted delivery of healthy endothelial cells.

Viscodilation balloon devices are well-established tools in the surgical management of glaucoma. These devices are designed to traverse Schlemm's canal 104 circumferentially and achieve controlled dilation by inflating a small-diameter balloon with a viscoelastic substance. The mechanical force exerted during inflation gently stretches the canal wall, disrupts synechiae, and opens the trabecular meshwork 106, thereby facilitating increased aqueous humor outflow and reducing intraocular pressure. However, despite their mechanical efficacy, these devices do not address the underlying biological deficits in glaucoma, namely the loss or dysfunction of Schlemm's canal endothelial cells, which are critical for maintaining physiological outflow resistance.

The concept of merging endothelial cell therapy with viscodilation balloons arises from both anatomical realities and the biological potential inherent in surgical manipulation. During balloon inflation, the mechanical expansion can denude the inner wall of Schlemm's canal 104, exposing underlying extracellular matrix components such as collagen and laminin. These freshly revealed surfaces provide a highly suitable substrate for endothelial cell adhesion, creating an opportune moment for therapeutic intervention. By introducing healthy endothelial cells into this prepared environment, it becomes possible to seed the canal wall with new cellular layers that can restore transcellular pore formation, regulate aqueous humor outflow, and potentially modulate postoperative healing and fibrosis.

9.5 Balloon Surface Coating with Hydrogel

To facilitate this novel integration, this document contemplates several specific embodiments of endothelial cell delivery using viscodilation balloon technology. One approach involves coating the external surface of the balloon with a hydrogel matrix that is preloaded with endothelial cells 208. In this configuration, the hydrogel adheres securely to the balloon as it is advanced through Schlemm's canal 104. When the balloon is inflated, the hydrogel layer is pressed firmly against the canal wall, promoting direct cell-to-tissue contact. Following deflation and withdrawal of the device, a portion of the endothelial cells 208 remains adhered to the inner wall of the canal. The hydrogels suitable for such coatings include polyethylene glycol diacrylate, hyaluronic acid derivatives, gelatin methacrylate, and PLGA-based materials, each chosen for their biocompatibility, tunable mechanical properties, and capacity to support cellular viability. However, this method imposes stringent engineering requirements because the hydrogel coating 602 must be extremely thin, often limited to 10 to 30 microns, to avoid increasing the balloon's outer diameter beyond the anatomical confines of Schlemm's canal 104. Moreover, the hydrogel must exhibit sufficient elasticity to withstand repetitive inflation and deflation without cracking, while maintaining controlled degradation characteristics to enable gradual cell release rather than premature detachment during device manipulation.

9.6 Endothelial Cell Integration with Balloons

Another contemplated method for combining endothelial cell therapy with balloon technology involves suspending endothelial cells directly in the viscoelastic medium used to inflate the balloon. In this scenario, the cells are dispersed uniformly within the viscoelastic solution, which is then injected to expand the balloon and exert radial pressure against the canal walls. The viscoelastic fluid, along with its cellular payload, contacts the exposed tissue surfaces during inflation. Upon deflation and conduit withdrawal, residual viscoelastic and a fraction of the delivered endothelial cells remain deposited along the canal's interior. This approach simplifies manufacturing by obviating the need for pre-coated devices and allows intraoperative customization of cell concentration.

Nevertheless, it introduces critical technical challenges, particularly in maintaining cell viability within the viscoelastic medium and preventing cellular damage from shear forces during injection and balloon expansion. The selected viscoelastic must be biocompatible, support cell survival, and exert minimal toxicity while still providing the mechanical properties necessary for effective canal dilation. Further, the surgeon must balance the cell density to achieve sufficient seeding of the canal wall without risking excessive aggregation, obstruction of collector channels, or postoperative elevation of intraocular pressure. In certain cases, irrigation or aspiration of residual viscoelastic may be necessary postoperatively to mitigate pressure spikes, a step that carries the potential drawback of washing away some of the delivered endothelial cells.

9.7 Deployable Hydrogel Sleeve Encasing Balloons

A third embodiment involves the deployment of a hydrogel sleeve 204 encasing the balloon. In this configuration, a thin, tubular hydrogel sleeve 204 preloaded with endothelial cells is fitted over the deflated balloon conduit prior to surgical insertion. As the balloon is inflated, the sleeve expands radially, pressing the endothelial cells into uniform contact with the canal wall over a defined arc, whether 180 or 360 degrees depending on surgical preference and anatomical considerations. Upon balloon deflation, the sleeve may be designed either to remain in situ as a biodegradable scaffold that continues releasing endothelial cells over time or to be withdrawn together with the balloon conduit if intended for single-use delivery.

This embodiment provides several advantages, including enhanced mechanical stability for the hydrogel structure, uniform circumferential contact between cells and the canal wall, and the potential for multilayer hydrogel constructions incorporating not only cells but also therapeutic agents such as anti-fibrotic compounds or growth factors. Nonetheless, this approach entails significant engineering challenges, particularly the need to manufacture hydrogel sleeves 204 thin enough to slide over the balloon without adding substantial bulk that might impede canal navigation. Additionally, excessive hydrogel swelling must be avoided to prevent canal lumen compression or obstruction of collector channels. Safe retrieval mechanisms must also be devised for sleeves intended for removal after the procedure.

9.8 Elasticity and Mechanical Stress of Balloons

Integrating endothelial cell therapy into viscodilation balloon devices demands careful attention to several unique technical considerations. The viscodilation process subjects devices to significant mechanical stress, requiring hydrogel materials to possess adequate elasticity and mechanical resilience to endure radial expansion and collapse without fragmentation or delamination. Hydrogels such as gelatin methacrylate and certain polyethylene glycol derivatives can be engineered to provide such elasticity, but precise formulation and crosslinking strategies are essential to balance mechanical durability with cellular compatibility.

9.9 Lubricity and Navigability of Balloons

Another critical consideration is the effect of hydrogel coatings on the frictional characteristics of the balloon surface. While hydrogels can increase surface friction and potentially cause traumatic tissue interaction during conduit advancement, certain formulations exhibit a lubricious or "greased" effect that may actually facilitate smoother navigation through Schlemm's canal 104. Identifying the appropriate balance between lubricity and adhesive stability is crucial to achieving both safe device insertion and effective endothelial cell delivery.

9.10 Balloon Size Constraints

Dimensional constraints further limit design options because Schlemm's canal 104 typically measures only 200 to 300 microns in diameter, while balloon devices are engineered to inflate to diameters ranging from approximately 200 to 400 microns. Any additional hydrogel layer or sleeve must remain within these strict anatomical boundaries to prevent complications such as canal rupture, compression of collector channels, or undesired postoperative increases in intraocular pressure. This necessity underscores the importance of meticulous hydrogel design, particularly in controlling both layer thickness and the hydrogel's swelling properties.

9.11 Sterility and Cell Viability of Balloons

Sterility and cell viability pose additional challenges for balloon-based delivery systems. Hydrogel coatings 602, hydrogel sleeves 204, and cell-suspended viscoelastic solutions must remain sterile throughout manufacturing, storage, and surgical use. Preservation techniques such as cryo-preservation or hypothermic storage are essential for maintaining high cell viability in preloaded devices, while intra-operative handling must be performed with care to avoid mechanical trauma to living cells.

Despite these challenges, the integration of endothelial cell therapy with viscodilation balloons offers numerous advantages. Such devices can achieve dual therapeutic action, simultaneously providing mechanical canal dilation and biological regeneration of the endothelium. Balloon inflation facilitates uniform, circumferential deposition of endothelial cells along the inner canal wall, which is a crucial factor in ensuring successful cell engraftment and physiological restoration. The workflow compatibility of balloon-based devices further increases their clinical appeal, as surgeons familiar with conventional canaloplasty can adopt endothelial cell therapy without significant changes to their established techniques. Additionally, healthy endothelial cells delivered via these devices may secrete factors that reduce postoperative fibrosis, thereby preserving surgical outcomes over the long term.

Given the complexity of these interventions, postoperative imaging using optical coherence tomography (OCT) and OCT angiography (OCTA) plays a pivotal role in monitoring the safety and efficacy of endothelial-cell-laden balloon procedures. Such imaging modalities can confirm the correct placement of hydrogel coatings 602 or hydrogel sleeves 204, assess canal patency, and detect signs of canal compression, aggregation of cells, or fibrosis. The integration of artificial intelligence algorithms into OCT and OCTA analysis offers further potential for rapidly identifying subtle abnormalities that might otherwise remain undetected, providing surgeons with timely insights and supporting real-time decision-making.

The combination of endothelial cell therapy with viscodilation balloon devices represents a highly promising advancement in the management of glaucoma. By bridging mechanical intervention and biological regeneration, these techniques redefine canaloplasty as a truly regenerative therapy. Through sophisticated hydrogel engineering, precise device mechanics, and advanced imaging support, this embodiment expands the therapeutic capabilities of endothelial cell technology, solidifying its role as a versatile platform for preserving and restoring ocular health.

10.0 APPLICATION OF ENDOTHELIAL CELL TECHNOLOGY TO TENSIONING SUTURES

The present document further contemplates the integration of endothelial cell therapy with tensioning sutures employed in minimally invasive glaucoma surgeries (MIGS). This embodiment represents another significant extension of the platform's nature, enabling the biological regeneration of Schlemm's canal 104 not only through stents, microcatheters, or balloons, but also via the mechanical interventions associated with canal tensioning techniques. By merging endothelial cell delivery with tensioning sutures, the platform seeks to transform canaloplasty into a hybrid mechanical-biological procedure, capable of simultaneously reshaping canal architecture and restoring its physiological endothelial lining.

Tensioning sutures are used as a means to maintain circumferential dilation of Schlemm's canal 104. In these procedures, a suture, typically made of a polypropylene monofilament, is circumferentially threaded through Schlemm's canal 104 and then gently tensioned. This process exerts an outward radial force on the canal walls, expanding its diameter and stretching the trabecular meshwork 106 to enhance aqueous humor outflow. The maintained tension reduces canal collapse and preserves the surgical result, contributing to a sustained lowering of intraocular pressure. However, despite these advantages, the use of tensioning sutures remains purely mechanical, offering no intrinsic means to regenerate or repair the endothelial cells lining the inner wall of Schlemm's canal 104.

10.1 Rationale for Integrating Endothelial Delivery with Tension Sutures

The rationale for integrating endothelial cell therapy into tensioning sutures stems from both mechanical and biological considerations. The mechanical passage of a suture through Schlemm's canal 104 inevitably imposes frictional forces against the canal walls, which can strip away or damage delicate endothelial cells. Moreover, the radial tension applied by the suture may exacerbate existing endothelial cell dysfunction or injury. Yet, this same surgical maneuver presents a unique therapeutic window, as the mechanical manipulation exposes fresh extracellular matrix surfaces, collagen, laminin, and fibronectin, that are highly conducive to cellular adhesion. Capitalizing on this exposed substrate, we seek to deliver endothelial cells along the suture's path, thereby promoting biological regeneration of the canal lining immediately following mechanical dilation.

10.2 Endothelial Coating of Tension Sutures

In one embodiment, endothelial cell delivery is achieved by coating the external surface of the suture with a hydrogel matrix preloaded with living endothelial cells 208. This hydrogel coating 602 is applied during the manufacturing process, utilizing techniques such as dip-coating, spray-coating, or extrusion to achieve a uniform layer surrounding the suture filament. Once coated, the hydrogel layer is crosslinked and cured ex vivo to establish the desired mechanical properties, structural integrity, and porosity necessary for both surgical handling and biological cell support. The choice of hydrogel materials may include polyethylene glycol diacrylate, hyaluronic acid derivatives, gelatin methacrylate, and PLGA-based hydrogels, which offer biocompatibility, customizable degradation rates, and the ability to maintain high levels of cell viability.

Designing a hydrogel coating 602 for sutures involves unique challenges. The hydrogel layer must be exceedingly thin, typically no more than 10 to 20 microns in thickness, to avoid significantly increasing the suture's diameter, which could impede threading through Schlemm's canal 104 narrow lumen. At the same time, the coating must exhibit sufficient elasticity and mechanical strength to withstand the physical stresses encountered during suture manipulation, tensioning, and knot tying. The hydrogel must also adhere reliably to the underlying suture material, resisting delamination or flaking under torsional or tensile loads. Furthermore, crosslinking density must be carefully optimized to balance the need for mechanical durability with controlled biodegradability and gradual cell release.

10.3 Hydrogel Sleeve for Tension Sutures

An alternative embodiment contemplates the use of a hydrogel sleeve 204 rather than a direct coating. In this approach, a slender tubular hydrogel sheath preloaded with endothelial cells 208 is fabricated to match the diameter of the tensioning suture. Prior to or during surgery, the hydrogel sleeve 204 is threaded onto the suture and advanced into Schlemm's canal 104 along with the suture itself. As the suture is tensioned and secured, the hydrogel sleeve 204 is compressed circumferentially against the canal wall, facilitating the transfer of endothelial cells 208 onto the exposed tissue surfaces. The sleeve may be engineered either to remain in place as a biodegradable scaffold or to be withdrawn after completing its cell delivery function.

This sleeve-based embodiment offers several potential advantages over direct hydrogel coatings 602. Hydrogel sleeves 204 can be manufactured separately from the suture, allowing for greater flexibility in adjusting wall thickness, cell loading density, and overall length to suit patient-specific anatomy or surgical preferences. Moreover, sleeves may provide mechanical protection for the endothelial cells 208 during the challenging manipulation and tensioning phases of canaloplasty. However, the use of hydrogel sleeves 204 also introduces unique engineering challenges, particularly the need to maintain tight tolerances on wall thickness to avoid obstructing Schlemm's canal 104. Excessive hydrogel swelling within the confined canal lumen must be carefully controlled, as it could cause compression of collector channels, compromise canal patency, or elevate intraocular pressure.

In either the hydrogel sleeve 204 or hydrogel coating 602 embodiments, preserving endothelial cell viability remains a critical concern. Cells loaded into hydrogels must remain alive and metabolically active throughout manufacturing, storage, and surgical deployment. Techniques such as cryo-preservation, hypothermic storage, and specialized moisture-retaining packaging can extend shelf life and maintain cell viability. However, mechanical stress during suture passage, tensioning, and knot tying can impose additional risks to cell survival, necessitating careful design of both hydrogel properties and surgical technique.

10.4 Integrating Endothelium in Tension Sutures

Integrating endothelial cell therapy into tensioning sutures also demands attention to surgical workflow. The introduction of a hydrogel-coated or hydrogel-sleeved suture should not substantially increase operative time or require complex new handling protocols. Manufacturers may address this by providing preloaded, ready-to-use devices that seamlessly integrate into existing canaloplasty techniques. Alternatively, surgeons may opt for intraoperative cell loading of hydrogel sleeves 204, offering maximum flexibility but imposing additional preparation time during surgery.

From a clinical standpoint, the benefits of combining endothelial cell therapy with tensioning sutures are considerable. The system provides a dual-action intervention that delivers both mechanical expansion and biological regeneration. The mechanical force exerted by the suture preserves canal patency and reduces the risk of postoperative canal collapse, while the delivered endothelial cells adhere to the canal wall, repopulate areas of cell loss, and restore physiological transcellular pore formation critical for regulated aqueous humor outflow. This regenerative effect may also reduce the likelihood of postoperative fibrosis, one of the key challenges undermining the long-term success of MIGS procedures.

TABLE 26

Comparison of Endothelial Cell Integration Strategies for Tensioning Sutures

| Feature | Hydrogel Coating on Suture | Hydrogel Sleeve over Suture |
|---|---|---|
| Cell Delivery Method | Endothelial cells embedded in a thin hydrogel layer directly bonded to suture surface. | Endothelial cells embedded in a separate tubular hydrogel sleeve threaded over the suture. |

TABLE 26-continued

Comparison of Endothelial Cell Integration Strategies for
Tensioning Sutures

| Feature | Hydrogel Coating on Suture | Hydrogel Sleeve over Suture |
|---|---|---|
| Hydrogel Application Technique | Dip-coating, spray-coating, or extrusion applied during manufacturing. | Sleeve molded separately (e.g. Extrusion, mandrel casting) the loaded onto the suture before or during surgery. |
| Thickness Control | Strictly controlled to ~10-20 µm to avoid increasing suture diameter and friction. | Wall thickness customizable; typically thicker than coatings but must fit Schlemm's canal lumen. |
| Mechanical Robustness | Must endure suture threading, tensioning, knot tying without cracking or delamination. | Sleeve must expand slightly to conform during tensioning yet resist tearing. More robust due to thicker geometry. |
| Cell Viability Concerns | Risk of shear damage during manipulation; requires gentle handling and durable hydrogel chemistry. | Potentially better mechanical protection for cells during surgery, as cells are embedded deeper in the sleeve matrix. |
| Customizability | Length and cell density predefined by manufacturer, less intraoperative flexibility. | Surgeons can trim sleeve length or adjust cell loaded immediately prior to surgery for patient-specific anatomy. |
| Storage & Shelf Life | Requires moisture-retentive packaging and possible cryopreservation for viable cells. | Similar requirements, but easier to package separately from the suture for flexible logistics. |
| Potential Swelling Issues | Minimal if coating is thin and tightly crosslinked; uncontrolled swelling could impair suture handling. | Higher swelling risk, excessive expansion may compress the canal lumen or obstruct the collector channels. |
| Surgical Workflow Impact | Pre-coated suture is ready to use, no added intraoperative steps. | Adds an intraoperative step if the surgeon loads the sleeve, but offers maximum flexibility. |
| Potential Regulatory Complexity | One integrated device requiring single regulatory approval for the combination product. | Sleeve could be regulated separately from suture, simplifying module approvals in some jurisdictions. |
| Advantages | Minimal change to existing surgical techniques. Uniform cell distribution. Seamless device integration. | Customizable length and cell load. Potentially better mechanical protection of cells. Flexibility for unique anatomy or complex cases. |
| Challenges | Strict control of hydrogel thickness. Maintaining adhesion during surgical manipulation. | Avoiding excessive sleeve thickness. Managing hydrogel swelling. Additional intraoperative steps if surgeon-loaded. |
| Clinical Use Case | Ideal for high-volume centers preferring turnkey, ready-to-use devices. | Suited for customized surgical plans or surgeons comfortable with intraoperative device preparation. |

Table 26 is a comparison of two primary strategies for integrating endothelial cell therapy with tensioning sutures in canaloplasty. Hydrogel coatings 602 offer minimal change to surgical workflow but demand precise manufacturing tolerances, while hydrogel sleeves 204 provide greater intraoperative flexibility at the cost of potential added complexity and anatomical constraints. Both approaches share the goal of delivering viable endothelial cells to restore Schlemm's canal function.

10.5 OCT, OCTA, and AI Integration for Postoperative Monitoring and Therapeutic Optimization The system leverages optical coherence tomography (OCT) and OCT angiography (OCTA) as integral components for both intraoperative guidance and postoperative monitoring in regenerative glaucoma surgery. These high-resolution imaging modalities offer non-invasive, cross-sectional, and vascular visualization of Schlemm's canal 104 and surrounding tissues, making them ideally suited to confirm device positioning, evaluate canal patency, and assess potential complications arising from hydrogel deployment, such as excessive swelling, endothelial cell aggregation, or unintended tissue compression.

Critically, OCT and OCTA can visualize the placement and tension of microstents or sutures, enabling clinicians to verify that the tensioning system is both mechanically effective and biologically compatible. When endothelial cell-seeded hydrogels or tensioning sutures are deployed, OCT-based imaging enables direct monitoring of their integration with the trabecular meshwork 106 and inner Schlemm's canal 104 wall-key to ensuring long-term patency and physiologic aqueous outflow.

This imaging-guided approach may be further enhanced by artificial intelligence (AI) systems integrated into the platform. These AI modules serve several functions, such as intraoperative imaging analysis. AI algorithms interpret live OCT/OCTA data to identify regions of Schlemm's canal 104 with suboptimal endothelial coverage. This enables real-time modulation of conduit dwell time and hydrogel delivery, ensuring more uniform therapeutic distribution.

The AI modules may also provide predictive modeling. By analyzing individual patient variables, including canal anatomy, surgical history, and demographics, AI can predict the likelihood of successful endothelial engraftment and guide procedural choices such as hydrogel composition or tensioning parameters.

The AI modules may provide automated postoperative surveillance. AI systems track postoperative imaging to detect subtle changes in canal architecture, such as early fibrotic response, loss of canal patency, or thinning of the endothelial layer. This provides an early-warning system that supports timely intervention and reduces the risk of surgical failure.

The integration of AI with OCT/OCTA not only augments the precision and adaptability of intraocular therapy but also positions the system as a next-generation platform for biologically intelligent glaucoma care. By uniting mechanical tensioning, regenerative cell therapy, advanced imaging, and real-time analytics, this embodiment supports a durable, individualized, and physiologically informed approach to restoring aqueous outflow and preserving vision.

11.0 DIRECT ENDOTHELIAL INJECTION OF HYDROGEL SUSPENSIONS INTO SCHLEMM'S CANAL

This document also contemplates the use of injectable suspensions as a method of delivering endothelial cells into Schlemm's canal 104. This embodiment represents a flexible and minimally invasive modality within the platform, offering an approach that complements both mechanical and biological strategies for glaucoma management. Unlike coatings, sleeves, or balloon-associated techniques, injectable suspensions provide a direct, free-flowing means of delivering therapeutic endothelial cells precisely where they are needed along the canal's circumference.

11.1 Preparation of Endothelial Suspension for Injection

Injectable suspensions of endothelial cells involve preparing a concentrated cell solution in a physiologically compatible carrier fluid. The carrier may consist of balanced salt solutions, buffered media, or low-viscosity biocompatible polymers such as hyaluronic acid. The cell density within this solution is meticulously controlled to deliver an adequate therapeutic dose while avoiding issues of aggregation or mechanical obstruction within the canal lumen. Depending on surgical strategy, suspensions may be injected circumferentially via microcatheters, targeted to specific Schlemm's canal 104 segments, or introduced in conjunction with viscodilation procedures.

One convenient advantage of injectable suspensions lies in their extreme adaptability to variable surgical circumstances. For instance, during canaloplasty, the surgeon may choose to inject endothelial cells following mechanical dilation, capitalizing on freshly exposed extracellular matrix surfaces that promote cell adhesion. Alternatively, cell suspensions can be delivered into discrete canal segments exhibiting damage or fibrosis, creating a targeted regenerative therapy tailored to individual patient anatomy.

However, the application of injectable endothelial cell suspensions also introduces unique technical and biological considerations. Chief among these is the need to balance cell concentration with the physical constraints of Schlemm's canal 104, which averages 200-300 microns in diameter. Suspensions that are too dilute may result in sub-therapeutic dosing, while excessively concentrated solutions increase the risk of cell clumping, which can obstruct outflow pathways, elevate intraocular pressure (IOP), and potentially cause ischemic damage to the delicate canal tissues.

To mitigate these risks, this document contemplates careful formulation of suspension viscosity and cell density. Carrier solutions may incorporate mild viscoelastic properties to reduce shear stress on endothelial cells during injection while maintaining flow characteristics that allow smooth passage through microcatheters. Such formulations are designed to prevent cellular sedimentation during intraoperative handling, thereby ensuring consistent cell distribution throughout the injection process.

11.2 Endothelial Cell Injection after Denudement with Imaging-Guided Targeting

The present disclosure contemplates a regenerative method directed toward restoring the specialized endothelial lining of Schlemm's canal 104. Conventional glaucoma therapies, including trabeculectomy, tube shunt implantation, and minimally invasive glaucoma surgeries, are designed to bypass or mechanically open the canal in order to improve aqueous humor outflow. While these procedures may transiently reduce intraocular pressure, they do not correct the underlying biological deficit that arises when the native endothelial lining of Schlemm's canal 104 becomes dysfunctional. The inner wall endothelium plays a central role in aqueous humor regulation, forming vacuoles and pores through which fluid traverses into collector channels. Dysfunction or loss of this cellular population results in sustained outflow resistance, even when the canal has been mechanically enlarged.

To directly address this deficiency, this document presents a method that combines the preparatory removal of non-functioning Schlemm's canal endothelial cells with the introduction of viable endothelial cells into the canal lumen. Denudement may be achieved through controlled viscoelastic shear forces, low-pressure suctioning, or microsurgical instruments adapted for confined luminal spaces. This preparatory step exposes a receptive substrate for adhesion by eliminating senescent or fibrotic tissues that would otherwise interfere with engraftment. Following denudement, a suspension of viable Schlemm's canal endothelial cells, endothelial progenitor cells, or stem-cell-derived endothelial-like cells is injected into Schlemm's canal 104 using a microcatheter or fine cannula. The transplanted cells adhere to the canal wall and, under physiologic shear conditions, form a functional monolayer capable of vacuole and pore formation.

While injection alone provides a means of reintroducing viable cells, this approach is constrained by the absence of structural or biochemical support. Cells delivered into the aqueous outflow pathway are subject to continuous shear stress and the risk of washout, resulting in inconsistent engraftment. In contrast, combining endothelial cell delivery with a stent, canaloplasty scaffold, or hydrogel substrate significantly enhances the likelihood of durable re-endothelialization. Such substrates maintain canal patency, present biomimetic surfaces coated with extracellular matrix proteins, and may incorporate bioactive signals such as nitric oxide-releasing polymers or RGD peptides. Together, these features stabilize transplanted cells, promote adhesion and survival, and support long-term physiologic function that cannot be reliably achieved by injection alone.

Corneal endothelial cell injection targets a broad posterior corneal surface to restore transparency, while Schlemm's canal 104 presents a narrow circumferential lumen that requires shear adaptation and dynamic pore formation. Similarly, reports of trabecular meshwork 106 transplantation or in vitro Schlemm's canal 104 models do not teach in vivo repopulation of the canal lumen following selective removal of dysfunctional endothelium. The present disclosure therefore introduces a novel therapeutic paradigm: the selective denudement of Schlemm's canal endothelium, followed by targeted delivery of viable endothelial cells, with or without a substrate-based scaffold, to restore physiologic outflow regulation.

In certain embodiments, imaging modalities are employed to plan, guide, and verify the procedure. Optical coherence tomography (OCT) provides micron-scale structural assessment of canal geometry, wall compliance, and focal collapse. Optical coherence tomography angiography (OCTA) supplies flow-based visualization, enabling identification of dysfunctional canal segments with impaired perfusion. Ultrasound, including high-frequency backscatter and Doppler, may be used to estimate shear stress and fluid-wall interactions. These modalities may be applied preoperatively to generate targeting maps for denudement, intraoperatively to guide catheter placement and confirm distribution of injected cells, and postoperatively to verify functional recovery. Integration of multimodal imaging, optionally with AI-based analysis, ensures precise localization of therapy, minimizes unnecessary manipulation, and documents re-endothelialization over time.

Schlemm's canal endothelial cells may be derived from donor tissue, expanded ex vivo, or differentiated from pluripotent stem cells. Delivery suspensions may include balanced salt solution, viscoelastic carriers, or hydrogel additives to enhance adhesion and reduce washout. Adjunctive biomolecules such as fibrinogen, hyaluronic acid, or RGD peptides further promote cell survival. When combined with structural stabilization provided by a stent or scaffold, these strategies enable a regenerative approach that restores the functional endothelium of Schlemm's canal 104.

Accordingly, the present disclosure provides both a method of direct endothelial cell injection after denudement and, more importantly, an improved strategy in which cell delivery is coupled with substrate-based devices to achieve superior outcomes.

11.3 Preservation of Endothelial Cell Viability in Suspensions

Preservation of cell viability is another consideration. Endothelial cells in suspension are highly sensitive to environmental stressors such as temperature fluctuations, osmotic shifts, and prolonged storage. As a result, suspensions intended for immediate surgical use may be prepared freshly under sterile conditions in the operating room, whereas pre-manufactured suspensions require stringent cryopreservation techniques to maintain cell integrity during storage and transport. Cryopreservation involves the use of cryoprotectants such as dimethyl sulfoxide (DMSO) and controlled cooling rates to avoid intracellular ice crystal formation, which can damage cell membranes and compromise therapeutic efficacy.

The logistics of delivering injectable suspensions into Schlemm's canal 104 also demand precise instrumentation and surgical skill. Surgeons must use microcatheters or fine cannulas with internal diameters sufficiently large to accommodate suspended cells without inducing shear stress that could damage cellular structures. Injection speed, pressure, and volume must be meticulously controlled to prevent reflux of cells into the anterior chamber or excessive distension of the canal.

11.4 OCT and OCTA Imaging in Endothelial Therapy Monitoring

The platform may employ Optical Coherence Tomography (OCT) and Optical Coherence Tomography Angiography (OCTA) as modalities for the postoperative evaluation of endothelial cell therapies delivered in hydrogel suspensions. These imaging techniques provide structural and functional insights for assessing treatment success, guiding follow-up interventions, and ensuring long-term patency of Schlemm's canal 104.

OCT enables high-resolution, cross-sectional visualization of Schlemm's canal 104 and adjacent tissues. Following hydrogel-based cell delivery, OCT imaging is used to assess the extent of canal expansion, the precise localization of the hydrogel matrix, and the interactions between the hydrogel and delicate structures such as the trabecular meshwork 106 and collector channel entrances. Importantly, OCT allows clinicians to evaluate distribution patterns of endothelial cells within the canal, identifying regions that are uniformly seeded, underpopulated, or excessively concentrated, each of which may carry implications for perfusion efficacy or fibrotic risk.

OCTA, which builds upon OCT by adding motion contrast imaging of red blood cell flow, provides functional data. In the postoperative setting, OCTA is used to assess aqueous outflow dynamics, detect perfusion asymmetries, and localize ischemic zones or early obstructions that may arise from hydrogel-induced swelling or cellular overaggregation. This modality also enables monitoring of vascular engagement at collector channels, offering a dynamic view of whether therapeutic intervention has successfully restored physiologic flow pathways.

Together, OCT and OCTA form a complementary imaging suite capable of identifying both structural integration and functional efficacy of the regenerative approach. When employed serially over time, these tools track the progression of cell engraftment, canal remodeling, and tissue healing, thereby informing clinical decisions regarding the need for retreatment or additional pharmacologic modulation.

11.5 Artificial Intelligence Analysis in Endothelial Cell Transfer and Conduit Monitoring The system may incorporate artificial intelligence (AI)-driven analytics to further enhance interpretive power. AI algorithms perform automated segmentation of Schlemm's canal 104, detecting changes in morphology, quantifying hydrogel volume, and identifying cellular patterns that may not be appreciable on visual inspection alone. AI can also interpret spectroscopic and reflectivity-based OCT signals to infer the viability of delivered endothelial cells and detect early fibrotic signatures through nuanced pattern recognition. In the context of OCTA, AI provides flow velocity mapping and temporal perfusion tracking, highlighting deviations from baseline that may signal impending complications.

These AI capabilities extend to intraoperative use, enabling real-time interpretation of OCT/OCTA data to optimize conduit dwell time, hydrogel release location, and cell dosing patterns. Predictive modeling based on patient-specific factors, such as age, canal curvature, and prior interventions, further enhances the likelihood of successful engraftment.

Postoperatively, AI systems continue to serve as intelligent monitors, flagging canal narrowing, quantifying endothelial coverage, and providing risk stratification for fibrosis or graft failure. These analytics, framed not as binary outputs but as probabilistic guidance tools, empower clinicians with enhanced precision while preserving surgical judgment.

Altogether, this integrated platform, combining hydrogel delivery of endothelial cells with OCT, OCTA, and AI, enables a science-driven, patient-specific approach to glaucoma therapy. It transforms traditional canaloplasty from a purely mechanical procedure into a regenerative, image-guided intervention, capable of restoring both the structure and function of the aqueous outflow system with novel control and insight.

TABLE 27

| | | Comparison of Endothelial Cell Delivery Modalities | |
| --- | --- | --- | --- |
| Feature | Injectable Suspension | Hydrogel Coating/Sleeve | Balloon-Based Delivery |
| Delivery Method | Direct injection of endothelial cells suspended in fluid carrier into Schlemm's canal. | Endothelial cells embedded in hydrogel matrix attached to devices (suture, catheter, sleeve). | Cells embedded in balloon coating, sleeve, or viscoelastic inflation medium. |

TABLE 27-continued

| | | | |
|---|---|---|---|
| Comparison of Endothelial Cell Delivery Modalities | | | |
| Feature | Injectable Suspension | Hydrogel Coating/Sleeve | Balloon-Based Delivery |
| Flexibility of Application | Highly flexible; can target entire canal or specific segments. | Predefined geometry; less intraoperative adaptability. | Limited by balloon size and inflation dynamics. |
| Control of Cell Dose | Surgeon can easily adjust cell number and injection volume. | manufacturer or Predetermined by intraoperative prep. | Predetermined by manufacturer or limited by balloon capacity. |
| Risk of Aggregation/Blockage | Higher if cell density too high or viscosity too low. | Lower risk due to solid matrix restraining cells. | Medium risk if hydrogel swells excessively or cell density is too high. |
| Mechanical Stability | No inherent structural scaffold; relies on tissue adhesion post-injection. | Hydrogel matrix provides physical stability and gradual cell release. | Balloon inflation ensures close tissue contact during delivery. |
| Manufacturing Complexity | Lower complexity; standard sterile cell preparation. | Higher complexity; precise hydrogel fabrication and coating techniques required. | High complexity; integrating hydrogel onto inflatable structures is challenging. |
| Shelf Life Considerations | Limited unless cryopreserved; fresh preparation often required. | Longer shelf life if cryopreserved; specialized packaging necessary. | Similar to hydrogel coatings; shelf life depends on cell viability preservation. |
| Surgical Workflow Impact | May add preparation and injection time; minimal impact overall. | Seamless if pre-manufactured; more steps if surgeon-prepared. | Integrated into device workflow; minimal added steps if preloaded. |
| Compatibility with Imaging (OCT/OCTA) | Requires careful postoperative imaging to confirm canal patency and cell placement. | Coatings/sleeves visible on OCT; predictable reflectivity helps localization. | Balloon and hydrogel reflectivity can aid intraoperative placement confirmation. |
| Potential Advantages | Highly customizable dosing. Simple logistics. Adaptable for focal treatments. Lower manufacturing costs. | Provides structural protection for cells. Controlled release over time. Uniform delivery along treated segment. | Combines mechanical dilation with biological therapy. Uniform circumferential contact during inflation. |
| Potential Challenges | Risk of reflux or leakage. Cell damage during injection. Shorter shelf life for living cells. | Requires precise hydrogel formulation. Mechanical fragility possible. Added manufacturing cost. | Device engineering constraints. Dimensional limits in narrow canals. Potential swelling risks. |

Table 27 shows a comparison of endothelial cell delivery modalities for Schlemm's canal 104 interventions. Each strategy offers unique advantages and challenges regarding mechanical support, cell dosing precision, surgical work-flow, and postoperative management. Injectable suspensions provide maximum flexibility, while hydrogel-based methods offer structural protection and controlled release. Balloon-based systems uniquely combine mechanical dilation with biological therapy but face distinct engineering constraints.

12.0 PHYSIOLOGICAL ROLE AND TARGET DENSITY RANGE

Schlemm's canal 104 is a narrow, delicate anatomical structure lined with specialized endothelial cells whose density under physiological conditions ranges between approximately 3,000 to 6,000 cells per square millimeter, a figure comparable to corneal endothelial density. These endothelial cells form a continuous monolayer along the canal wall, creating a semi-permeable barrier between the aqueous humor and the distal collector channels. They regulate aqueous humor outflow via the formation of tran-scellular pores and giant vacuoles, maintain low resistance to outflow, and preserve intraocular pressure (IOP) within physiological limits. Additionally, they serve as a biome-chanical interface adapting to pressure fluctuations and contributing to tissue homeostasis and local immune modu-lation.

Restoring or maintaining this endothelial layer at a suit-able density is necessary for the success of regenerative therapy targeting glaucomatous disease. Both insufficient and excessive endothelial cell densities carry risks that must be addressed through precise dosing and engineering con-trol.

12.1 Metrics of Hydrogel Swelling and Diameter

Swelling of the hydrogel sleeve 204 after deployment directly influences the effective device diameter and must be carefully engineered to remain within the anatomical limits of Schlemm's canal 104. For example, consider a conduit with a bare diameter of 200 μm and a hydrogel coating thickness of 15 μm. This yields an initial coated diameter of:

$$D_{coated} = 200 \text{ μm} + 2 \times 15 \text{ μm} = 230 \text{ μm}$$

If the hydrogel swells by 30%, the final swollen diameter becomes:

$$D_{coated}=230 \text{ } \mu m \times (1+0.30)=299 \text{ } \mu m$$

This remains within the generally accepted anatomical range of Schlemm's canal 104, typically 250-300 μm in diameter. However, the presence of cellular aggregates or uneven swelling may exceed this threshold, posing a risk of canal obstruction or mechanical stress on the trabecular meshwork 106. For this reason, the document provides design constraints and dose-limiting measures to avoid excess bulk from either hydrogel expansion or cell payload density.

12.2 Hydrogel Engineering and Biological Strategies for Safety

To ensure anatomical compatibility and therapeutic safety, the system incorporates advanced hydrogel engineering and biological control mechanisms that minimize the risk of canal obstruction, endothelial aggregation, and cell loss. Hydrogels used in this system are formulated with internal network architectures that foster uniform cell distribution while limiting undesired migration or clustering. These structural characteristics help maintain a controlled cell density along the length of the canal, reducing the potential for nodular accumulation or asymmetric seeding.

In addition, hydrogel composites may be engineered with tunable release kinetics, enabling gradual dispersion of endothelial cells 208 rather than abrupt deposition. This controlled-release behavior supports physiological integration by giving endothelial cells time to adhere and adapt to local canal wall surfaces before significant volumetric accumulation occurs.

Layer thickness is carefully calibrated during manufacturing to remain well within Schlemm's canal 104 dimensions, even after expected swelling. OCT and OCTA imaging further contribute to safety monitoring by enabling visualization of focal narrowing, hyperreflective zones indicative of aggregation, or signs of lumen compromise. These imaging modalities offer a noninvasive means of identifying complications in real-time and can guide immediate postoperative decisions or dosing adjustments.

Finally, the viability and functionality of endothelial cells are validated through pre-deployment assays that measure apoptotic markers, membrane integrity, and metabolic activity. This ensures that only high-quality, viable cells are delivered to the canal, optimizing both safety and therapeutic efficacy. These engineering and biologic safeguards collectively enable functioning as a precision-guided, anatomy-respecting platform for regenerative canal-based therapy.

13.0 CLINICAL CARE FOR PATIENTS WITH REGENERATIVE THERAPY

Clinicians should monitor for signs of endothelial cell aggregation or canal stenosis postoperatively, including elevated IOP, gonioscopic evidence of canal narrowing, or OCT findings of lumen compromise. Depending on severity, management may range from observation and topical hypotensive therapy to surgical revision or hydrogel removal.

13.1 Predicate Models of Regenerative Care

Experience from corneal endothelial transplantation and vascular graft engineering further underscores the importance of controlled cell seeding densities. In vascular grafts, excessive endothelial cell density can cause neointimal hyperplasia, while in corneal transplants, high densities increase risks of cell clustering, anterior chamber shedding, and postoperative inflammation. These lessons support the proposed safe ranges of approximately 2,500-3,500 cells/mm² for endothelial cell therapy in Schlemm's canal 104.

13.2 Conclusion

The system balances regenerative potential with anatomical and fluid dynamic constraints, ensuring that endothelial cell therapy for Schlemm's canal 104 remains safe, effective, and manufacturable. Through mathematical modeling, engineering innovation, and advanced imaging integration, the platform provides a rigorous pathway for delivering endothelial cells in controlled densities, thereby avoiding the risks of canal obstruction and postoperative complications.

14.0 EXTENDING THE METHODOLOGY TO OTHER EMBODIMENTS

The present system is designed not merely as a solution for today's minimally invasive glaucoma surgeries (MIGS), but as a versatile platform technology capable of adapting to future innovations in ophthalmic surgical devices and procedures. This forward-looking design ensures that the disclosed endothelial cell delivery methodologies remain relevant as surgical tools, imaging modalities, and regenerative therapies evolve.

In the field of glaucoma management, technological progress has been rapid and diverse, with novel device concepts emerging regularly. These include advanced microcatheters with integrated sensors, robotic-assisted surgical instruments, bioresorbable scaffolds, and injectable bioengineered matrices that combine therapeutic functions with structural support. Although many of these devices remain under development, they share a common need: the ability to interact safely and effectively with Schlemm's canal, while preserving or enhancing its physiological function.

This document anticipates such future devices by establishing a foundational principle: that endothelial cell therapy can be coupled with any method of canal access, mechanical dilation, or fluid modulation to promote biological regeneration of Schlemm's canal 104. Whether the approach involves physical expansion, fluid-based flushing, local drug delivery, or precise micro-manipulation, endothelial cell integration remains applicable.

For example, emerging microcatheter designs may incorporate integrated micro-sensors capable of real-time pressure monitoring, flow measurement, or tissue characterization. In such devices, endothelial cells may be delivered through microchannels engineered into the conduit walls or released from nanoparticle-loaded hydrogels responsive to specific canal conditions detected by these sensors. Similarly, robotic-assisted surgical systems may allow precise, segmental cell seeding under image guidance, enabling targeted regenerative therapy limited only to the diseased portions of Schlemm's canal 104.

Another avenue of potential integration lies in the development of bioresorbable scaffolds tailored to conform to the canal's anatomy. These scaffolds could be impregnated with endothelial cells and designed to gradually degrade, leaving behind a restored endothelial layer while maintaining canal patency during the critical healing phase. Such devices may be fabricated from advanced materials like polycaprolactone (PCL), polydioxanone (PDO), or newer hybrid composites optimized for controlled biodegradation and cell viability.

Furthermore, future devices may employ injectable bioengineered matrices or soft, shape-memory polymers that conform to complex canal geometries. Endothelial cells could be integrated directly into these injectable formulations, enabling localized regeneration with minimal physical disruption. The system remains applicable in these contexts because its core principles, cell viability, adhesion, uniform distribution, and compatibility with canal anatomy, transcend specific device architectures.

Ultimately, the system positions endothelial cell therapy as a biological augmentation strategy universally applicable to any technique that interacts with Schlemm's canal 104. This ensures that the system remains relevant and valuable across successive generations of glaucoma treatment technologies.

TABLE 28

Examples of Future Devices and Applicability of Endothelial Cell Therapy

| Future Device Concept | Description | Potential Integration with Endothelial Cell Therapy | Advantages of Integration | Challenges to Address |
|---|---|---|---|---|
| Sensor-Integrated Microcatheters | Microcatheters equipped with sensors for pressure, flow, or tissue analysis. | Endothelial cells delivered via microchannels; release triggered by sensor data. | Targeted cell delivery. Dynamic control based on real-time data. Personalized therapy. | Miniaturization limits hydrogel volume. Complex manufacturing. |
| Robotic-Assisted Surgical Systems | Robotic tools enabling ultra-precise manipulation inside Schlemm's canal. | endothelial cells Precise, segmental seeding of under image guidance. | Avoids overtreatment. Precise application only where needed. Reduced surgical trauma. | Requires advanced training. High device costs initially. |
| Bioresorbable Scaffolds | Biodegradable structures conforming to canal anatomy, maintaining patency. | Scaffolds impregnated with endothelial cells and therapeutic agents. | Sustained structural support. Gradual cell release. Avoids need for device removal. | Material compatibility. Controlling degradation timing. |
| Injectable Bioengineered Matrices | Soft hydrogels or shape-memory polymers injected into the canal. | Matrices preloaded with endothelial cells; conform to canal walls. | Minimal surgical disruption. Custom fit to canal anatomy. Simultaneous drug delivery possible. | Swelling control. Risk of canal obstruction if overly viscous. |
| AI-Guided Delivery Systems | AI analyzing OCT/OCTA to guide targeted cell placement. | Identifies precise zones of damage for cell deposition. | Optimizes therapeutic efficacy. Reduces cell waste. Personalized medicine. | Requires extensive training datasets. Regulatory acceptance of AI decisions. |

This document contemplates the use of artificial intelligence (AI) and advanced imaging to guide endothelial cell delivery. AI algorithms trained on OCT and OCTA data can identify regions of endothelial loss, fibrosis, or abnormal canal morphology, directing future devices to deposit cells precisely where needed. This approach not only enhances therapeutic efficacy but also minimizes unnecessary cell deployment, preserving valuable biological materials and reducing procedural risks.

From a regulatory and commercial standpoint, the platform nature offers significant strategic advantages. By defining endothelial cell therapy as a modular component that can be combined with various surgical tools, the system facilitates a flexible regulatory pathway. Future devices may be approved individually under device or combination-product pathways, while still leveraging the same endothelial cell technologies disclosed herein. This modular strategy enhances commercialization potential by allowing rapid adaptation to new market entrants without the need for entirely new regulatory submissions for each novel device.

Table 28 illustrates examples of potential future device innovations and their compatibility with the disclosed endothelial cell therapy. Integration of biological regeneration with emerging surgical and diagnostic technologies positions the system as a versatile platform for future glaucoma treatment paradigms. The disclosed system provides endothelial cell delivery in combination with any surgical device or system that enters, expands, manipulates, or analyzes Schlemm's canal 104.

14.1 Direct Intra-Schlemm Injection and Imaging-Guided Delivery

The present document contemplates that, alongside conduit-based systems, direct injection of therapeutic substances, such as endothelial cell suspensions or hydrogel formulations, into Schlemm's canal 104 may become a viable and precise treatment modality. While Schlemm's canal 104 presents a small anatomical target, technological advances now make it increasingly feasible to pursue intra-Schlemm injections, provided certain design and surgical parameters are implemented to ensure safety and efficacy.

14.2 Imaging and Anatomical Localization

Modern anterior segment optical coherence tomography (OCT) enables high-resolution imaging of Schlemm's canal 104 in real-time. Future clinical systems are anticipated to integrate swept-source OCT or adaptive optics, delivering precise three-dimensional maps of canal position, diameter, and depth relative to external scleral landmarks. The following enablement conditions can support successful direct injection: Anatomical Mapping: OCT images can be processed to create a "canal map," including coordinates for external scleral entry points. External Marking Systems: Correlating OCT images with external markings ensures accurate needle positioning over the canal, reducing reliance on tactile feedback alone. Intraoperative Guidance: Real-time OCT can confirm needle tip entry into the lumen, helping avoid misplacement.

These imaging tools, integrated with surgical planning software, will support the accurate, patient-specific targeting necessary for safe intra-Schlemm injections.

14.3 Microneedle and Delivery System Development

To achieve safe canal entry, needle size and delivery systems must align with Schlemm's canal 104 dimensions, which range from approximately 190 to 370 micrometers in diameter. Enablement conditions include ultrafine microneedles that use manufacturing processes such as laser micromachining and microfabrication to produce needles with outer diameters as small as 100-150 micrometers. These micro-needles could be engineered with short bevels to reduce penetration depth, flexible shafts for controlled deflection and reduced trauma, integrated pressure sensing such as small sensors that may be embedded into needle hubs to monitor injection pressure in real time, preventing over-pressurization, and depth-control mechanisms such as precision stops, sleeves, or robotic controls to regulate insertion depth, ensuring that the needle enters but does not perforate the canal.

14.4 Controlled Injection Parameters

Schlemm's canal 104 functions under low intraocular pressures. Any injection system must deliver therapeutic material gently to avoid canal damage or fluid misdirection. Enablement conditions include low-pressure delivery systems such as syringe pumps or microfluidic injectors that can maintain steady, low flow rates. For instance, the typical target pressures might be kept below 20-25 mmHg, the flow rates can be limited to single-digit microliters per second, the volume limits may be based on canal volume estimates, safe delivery volumes would likely be in the range of 5-15 microliters per treated segment, depending on the canal's dimensions. The hydrogel injectates can be formulated to remain low-viscosity during injection, and undergo rapid in situ gelation to secure cells without swelling excessively.

These controlled parameters ensure compatibility with Schlemm's canal 104 physiology and maintain safe intraocular pressures.

14.5 Potential Benefits of Direct Injection

If successfully developed, direct intra-Schlemm injection could reduce surgical time by eliminating conduit passage through the canal, enable focal therapy for segmental canal disease, lower barriers to treatment in resource-limited settings where sophisticated microcatheters may be unavailable, and allow repeatable treatments without cumulative device trauma to the canal wall.

Furthermore, a minimally invasive injection technique could expand the utility of endothelial cell therapy beyond glaucoma, making it suitable for other conditions associated with endothelial dysfunction, fibrosis, or localized canal injury.

14.6 Viability of Injected Cell Suspensions

Endothelial cells are delicate and prone to mechanical stress. Enablement strategies for cell delivery include shear-protective hydrogels with formulations containing biocompatible polymers (e.g., hyaluronic acid, PEG derivatives) can protect cells during injection, reducing mechanical shear stress, suspension homogeneity using gentle mixing protocols ensure even cell distribution and minimize aggregation, and optimized concentration for intra-Schlemm injection, cell concentrations might be maintained in the range of 10,000-20,000 cells per microliter, balancing therapeutic density with the risk of obstruction.

Viability assays, such as live/dead staining, and preclinical injection studies can verify that high cell survival rates are achievable under these conditions.

Conditions Towards Enablement

Based on the above considerations, direct intra-Schlemm injection is an achievable and logical extension of current surgical technology. The present document anticipates future clinical tools that will integrate OCT-based mapping and live needle guidance, employ ultrafine microneedles with depth controls, utilize biocompatible hydrogel carriers to stabilize cell delivery, and operate within safe pressure and volume parameters to protect canal integrity.

Ongoing research, combined with advances in microfabrication and imaging, positions intra-Schlemm injection as a realistic and highly innovative pathway for delivering regenerative endothelial therapies.

TABLE 29

Potential Non-Glaucomatous Applications of Endothelial Cell Delivery to Schlemm's Canal

| Condition/ Indication | Clinical Scenario | Rationale for Endothelial Cell Delivery |
| --- | --- | --- |
| Post-Surgical Trauma or Scarring | Revision canaloplasty, failed MIGS, trabeculectomy revisions | Replaces endothelial cells lost due to prior surgery, helps restore normal canal function, reduces scarring. |
| Primary or Secondary Ocular Hypertension (Non-Glaucomatous) | Elevated IOP without optic nerve damage | Early regenerative intervention could normalize outflow resistance before progression to glaucoma. |
| Steroid-Induced Ocular Hypertension | Chronic steroid therapy for uveitis, post-transplant care | Counteracts steroid-induced dysfunction of canal endothelium, helps restore normal outflow. |
| Congenital/ Developmental Anomalies | Childhood ocular hypertension, hypoplastic Schlemm's canal | Regenerates absent or defective endothelial lining, potentially normalizing canal physiology. |

TABLE 29-continued

Potential Non-Glaucomatous Applications of Endothelial Cell
Delivery to Schlemm's Canal

| Condition/ Indication | Clinical Scenario | Rationale for Endothelial Cell Delivery |
|---|---|---|
| Post-Inflammatory Canal Damage | After anterior uveitis or other inflammatory conditions | Repairs endothelial injury caused by inflammation, prevents chronic outflow resistance increases. |
| Surgical or Traumatic Canal Wall Injury | Canal trauma from ocular injuries or surgical instruments | Supports healing of injured canal tissue, reduces risk of fibrosis or stenosis. |
| Idiopathic or Age-Related Endothelial Decline | Elderly patients with borderline IOP or early dysfunction | Prevents further functional decline by replenishing endothelial cells, preserves natural outflow capacity. |
| Collector Channel or Adjacent Tissue Repair | Damage at collector channel ostia or trabecular meshwork transition zones | Provides regenerative support to structures adjacent to Schlemm's canal, potentially enhancing overall outflow. |

Table 29 described a non-glaucomatous ocular conditions in which endothelial cell delivery to Schlemm's canal 104 may provide therapeutic benefit. These indications reflect broader utility of the disclosed hydrogel-based delivery systems, addressing anatomical or functional deficits beyond traditional glaucoma treatment.

15.0 ADVANTAGES

Building upon the concept of hydrogel-coated microcatheters for endothelial cell delivery, this document diverges from existing canaloplasty technologies by introducing a biological regenerative component rather than relying solely on mechanical intervention. This system uses hydrogel sleeves 204 or hydrogel coatings 602 applied to the external surface of microcatheters. These hydrogel layers are engineered to deliver endothelial cells 208 circumferentially along the inner wall of Schlemm's canal 104, promoting uniform cell distribution and potential engraftment. They also provide mechanical protection for the delicate canal endothelium during conduit advancement, reducing trauma compared to bare-device manipulation, and may optionally release therapeutic agents or growth factors to enhance cellular viability and the regenerative process.

One benefit lies in its capacity for cellular repopulation. Delivered endothelial cells 208 can regenerate the native canal lining and restore physiological functions, including the formation of transcellular pores and vacuoles essential for maintaining aqueous humor outflow and intraocular pressure regulation. Unlike conventional canaloplasty devices that solely rely on structural dilation, the system facilitates a biologically driven restoration of function.

The system is adaptable to existing surgical approaches and may be used in combination with viscodilation and trabecular meshwork 106 modification for a hybrid biological-mechanical therapeutic effect. This is a platform technology compatible with current and future microcatheter geometries and surgical advancements, positioning it as a forward-compatible solution within the evolving field of minimally invasive glaucoma surgery.

In summary, the system offers several unique advantages: it achieves uniform circumferential delivery of endothelial cells, minimizes the risk of canal obstruction through safe dosing strategies, allows controlled release of therapeutic materials via hydrogels, enhances endothelial survival and integration, avoids the shortcomings of purely mechanical interventions, supports AI-driven precision guidance, and maintains broad compatibility with a range of devices and future innovations. These attributes collectively define a novel, intelligent, and regenerative system for restoring ocular outflow physiology.

16.0 APPENDIX

TABLE 30

Comparison of Pre-Coated Conduits vs. Hydrogel Sleeves

| Feature | Pre-Coated Conduit (Manufacturer-Applied) | Separate Hydrogel Sleeve (Manufacturer or Surgeon-Applied) |
|---|---|---|
| Coating Location | Hydrogel directly adhered to conduit shaft | Hydrogel forms a tubular sleeve that slides over conduit |
| Thickness Control | Precisely controlled factory coating | duringThickness adjustable during sleeve molding or surgeon prep |
| Customization of Length | Limited to manufacturer's standard lengths | Fully customizable intraoperatively |
| Cell Loading | Preloaded during manufacturing; consistent | Can be loaded during manufacturing or immediately before surgery |
| Shelf Life | Cryopreserved or refrigerated; 1-2 years max | Cryopreserved or refrigerated; 1-2 years (manufacturer sleeve) or immediate use only (surgeon-prepared) |
| Handling Robustness | More prone to shear damage during shipping | Thicker sleeves often more mechanically robust |
| Surgical Workflow | Ready-to-use out of packaging | Adds intraoperative preparation time if surgeon-prepared |
| Packaging Complexity | Higher for moisture-sensitive coatings | Moderate; sleeves easier to handle separately |
| Ideal For | High-volume centers wanting simplicity | Customized cases; complex anatomies; flexible supply chains |

Table 30 shows a comparison of key attributes between pre-coated catheters and separate hydrogel sleeves used for endothelial cell delivery into Schlemm's canal. This table highlights practical differences in manufacturing methods, handling, customization, storage requirements, and surgical workflow. It is intended to assist surgeons, surgical centers, and manufacturers in selecting the optimal hydrogel delivery format based on clinical preferences, logistical considerations, and patient-specific anatomy.

TABLE 31

Frictional and Dimensional Comparison of Microcatheters with Pre-Formed Hydrogel Coatings

| Conduit Material | Bare Coefficient of Friction ($\mu\_bare$) | Typical Bare Diameter (µm) | Hydrogel-Coated Coefficient of Friction ($\mu\_coated$) | Hydrogel Layer Thickness (µm per side) | Total Diameter with Hydrogel (µm) | Within Canal Lumen (190-370 µm)? |
|---|---|---|---|---|---|---|
| Polyimide | 0.35 | 200 | 0.09 | 15 | 230 | Yes |
| PTFE (Teflon) | 0.10 | 180 | 0.09 | 15 | 210 | Yes |
| PEEK | 0.20 | 250 | 0.09 | 20 | 290 | Yes |
| Silicone | 0.25 | 220 | 0.09 | 15 | 250 | Yes |

Table 31 shows the dimensional tables provided herein reflect hydrogel coatings that are pre-formed onto the conduit ex vivo, where coating thickness and overall conduit diameter can be precisely controlled and measured. In embodiments where the hydrogel forms in situ during surgery, coating thickness and diameter may vary depending on surgical technique, canal geometry, and hydrogel swelling properties. In situ-formed hydrogels are contemplated to conform to Schlemm's canal anatomy without necessarily forming a uniform radial layer around the conduit shaft. Accordingly, dimensional values in the tables may not directly apply to in situ hydrogel embodiments but are included to illustrate typical parameters for pre-formed coatings.

Note that the data in Table 31 applies to pre-formed hydrogel configurations manufactured ex vivo and may not directly reflect dimensional changes in in situ-formed hydrogel embodiments.

TABLE 32

Schlemm's Canal Volume Calculations

| Canal Diameter (µm) | Canal Length (mm) | Volume (µL) |
|---|---|---|
| 190 | 36 | ~1.02 |
| 250 | 36 | ~1.77 |
| 300 | 36 | ~2.55 |
| 350 | 36 | ~3.46 |

TABLE 33

Single Cell Volume Calculation

| Cell Diameter (µm) | Single Cell Volume (mm³) |
|---|---|
| 10 | ~0.00052 |
| 15 | ~0.00177 |
| 20 | ~0.00419 |

TABLE 34

Safe Cell Dosing Examples

| Hydrogel Volume (µL) | Cell Density (cells/mL) | Total Cells Delivered |
|---|---|---|
| 2 | $1 \times 10^6$ | 2,000 |
| 5 | $1 \times 10^6$ | 5,000 |
| 10 | $5 \times 10^5$ | 5,000 |
| 10 | $1 \times 10^7$ | 100,000 |

TABLE 35

Hydrogel Materials and Properties

| Hydrogel Type | Crosslinking Method | Key Features |
|---|---|---|
| PEG-Diacrylate | UV light | Tunable degradation, biocompatibility |
| Hyaluronic Acid | Enzymatic | Naturally occurring, cell adhesion |
| PLGA Hydrogels | Hydrolysis | Slow degradation, drug co-delivery |
| GelMA | UV light | ECM motifs, cell compatibility |

TABLE 36

Co-Delivered Pharmaceutical Agents

| Drug/Compound | Function |
|---|---|
| Nitric Oxide Donors | Enhance pore formation |
| Anti-fibrotic Agents | Reduce canal fibrosis |
| Growth Factors | Promote endothelial proliferation |
| ECM Proteins | Improve cell adhesion |

TABLE 37

AI-Integrated Features

| AI Application Area | Example Functions |
|---|---|
| Intraoperative Guidance | OCT analysis, canal morphology mapping |
| Dosing Optimization | Predictive cell volume recommendations |
| Postoperative Monitoring | Detect early fibrosis, canal narrowing |

While the above description focuses on human embodiments, the system and techniques could be applied to veterinary implementations in the eyes of various animals.

Those skilled in the art will appreciate that the exemplary embodiments and descriptions thereof are merely illustrative of the inventions as a whole. Any dimensions used herein are for example, and any dimension may be modified without changing the scope of the claims. While the principles of the inventions have been made clear in the exemplary embodiments, it will be obvious to those skilled in the art that modifications of the structure that modifications of the structure, arrangement, proportions, elements, and materials may be utilized in the practice of the inventions, which are particularly adapted to specific environments and operative requirements without departing from the principles of the inventions.

LISTING OF DRAWING ELEMENTS 102 eye
104 Schlemm's canal
106 trabecular meshwork
108 zonules
110 lens
112 cornea
114 iris
116 ciliary body
202 catheter
204 hydrogel sleeve
206 viscoelastic
208 endothelial cells
302 microcatheter
304 curved path
306 therapeutic agents
402 advance device
404 position device
406 initiate hydrogel degradation
408 release endothelial cells
410 viscodilation
412 tensioning suture
414 withdraw device
416 monitor endothelial coverage
502 surface preparation
504 hydrogel preconditioning
506 preparation of endothelial cell suspension
508 dipping process
510 static incubation
512 rinsing and stabilization
514 optional crosslinking
516 storage or immediate use
602 hydrogel coating
702 nanoscale ridges
704 nanoscale patterns
706 nanopores
708 bioactive sleeve
802 preoperative planning
804 hydrogel preparation
806 device assembly
808 intraoperative imaging
810 catheter insertion 812 hydrogel deployment
814 postoperative monitoring
816 AI integration

The invention claimed is:

1. A device comprising:
a catheter, configured for insertion into an incision providing access to Schlemm's canal of an eye; and
a tubular hydrogel sleeve positioned around a distal shaft of the catheter, the tubular hydrogel sleeve comprising Schlemm's canal endothelial cells.

2. The device of claim 1, wherein the incision is in a cornea.

3. The device of claim 1, wherein the tubular hydrogel sleeve comprises polyethylene glycol (PEG).

4. The device of claim 1, wherein the tubular hydrogel sleeve comprises collagen.

5. The device of claim 1, wherein the tubular hydrogel sleeve comprises glucose.

6. The device of claim 1, wherein the tubular hydrogel sleeve comprises nitinol.

7. The device of claim 1, wherein the tubular hydrogel sleeve comprises nanopores.

8. The device of claim 1, further comprising a lumen configured to deliver a viscoelastic through the catheter.

9. A device comprising:
a catheter, configured for insertion into an incision providing access to Schlemm's canal of an eye; and
a hydrogel coating bonded to a surface of a distal shaft of the catheter, the hydrogel coating comprising Schlemm's canal endothelial cells.

10. The device of claim 9, wherein the incision is in a sclera.

11. The device of claim 9, wherein the hydrogel coating comprises hyaluronic acid.

12. The device of claim 9, wherein the hydrogel coating comprises alginate.

13. The device of claim 9, further comprising a lumen configured to deliver a viscoelastic through the catheter.

14. The device of claim 1, wherein the tubular hydrogel sleeve includes hyaluronic acid.

15. The device of claim 9, wherein the hydrogel coating comprises polyethylene glycol (PEG).

* * * * *